US011925334B2

(12) United States Patent
Grace et al.

(10) Patent No.: US 11,925,334 B2
(45) Date of Patent: Mar. 12, 2024

(54) SURGICAL INSTRUMENT FOR REMOVING AN IMPLANTED OBJECT

(71) Applicant: SPECTRANETICS LLC, Colorado Springs (CO)

(72) Inventors: Kenneth P. Grace, Woodland Park, CO (US); Bruce A. Hoo, Colorado Springs, CO (US)

(73) Assignee: SPECTRANETICS LLC, Colorado Springs, CO (US)

( * ) Notice: Subject to any disclaimer, the term of this patent is extended or adjusted under 35 U.S.C. 154(b) by 650 days.

(21) Appl. No.: 17/107,194

(22) Filed: Nov. 30, 2020

(65) Prior Publication Data

US 2021/0128130 A1 May 6, 2021

Related U.S. Application Data

(63) Continuation of application No. 15/890,151, filed on Feb. 6, 2018, now Pat. No. 10,849,603, which is a
(Continued)

(51) Int. Cl.
*A61B 17/00* (2006.01)
*A61B 17/32* (2006.01)
(Continued)

(52) U.S. Cl.
CPC .................. *A61B 17/00234* (2013.01); *A61B 17/320016* (2013.01); *A61B 17/32053* (2013.01);
(Continued)

(58) Field of Classification Search
CPC ...... A61B 17/00234; A61B 17/320016; A61B 17/32053; A61B 2017/2903;
(Continued)

(56) References Cited

U.S. PATENT DOCUMENTS 1,663,761 A 3/1928 Johnson
2,708,437 A 5/1955 Hutchins
(Continued)

FOREIGN PATENT DOCUMENTS

JP H05506382 A 9/1993
WO 1991017711 A1 11/1991
(Continued)

OTHER PUBLICATIONS

U.S. Appl. No. 14/635,742 entitled Multiple Configuration Surgical Cutting Device filed Mar. 2, 2015.
(Continued)

*Primary Examiner* — Julian W Woo

(57) ABSTRACT

Methods and devices for separating an implanted object, such as a pacemaker lead, from tissue surrounding such object in a patient's vasculature system. Specifically, the tissue separating device includes a handle, an elongate sheath and a circular cutting blade that may extend from the distal end of the sheath upon actuating the handle. The elongate sheath, particularly its distal end, includes a non-uniform wall thickness having one or more thicker portions in the outer sheath, particularly the outer cam member, and/or one or more thicker portions in an inner member disposed radially inward of the blade.

18 Claims, 37 Drawing Sheets

Related U.S. Application Data continuation of application No. 14/771,775, filed as application No. PCT/US2014/026496 on Mar. 13, 2014, now Pat. No. 9,925,366.

(60) Provisional application No. 61/793,597, filed on Mar. 15, 2013.

(51) Int. Cl.
| | | |
|---|---|---|
| *A61B 17/3205* | (2006.01) | |
| *A61B 17/34* | (2006.01) | |
| *A61B 17/29* | (2006.01) | |
| *A61B 90/00* | (2016.01) | |
| *A61N 1/05* | (2006.01) | |

(52) U.S. Cl.
CPC .............. *A61B 17/3468* (2013.01); *A61B 2017/00455* (2013.01); *A61B 2017/2903* (2013.01); *A61B 2017/2924* (2013.01); *A61B 2017/32004* (2013.01); *A61B 2090/08021* (2016.02); *A61B 2090/0811* (2016.02); *A61N 1/056* (2013.01)

(58) Field of Classification Search
CPC .. A61B 2017/2924; A61B 2017/32004; A61B 2090/08021
See application file for complete search history.

(56) References Cited

U.S. PATENT DOCUMENTS

| | | |
|---|---|---|
| 3,400,708 A | 9/1968 | Scheidt |
| 3,614,953 A | 10/1971 | Moss |
| 3,756,242 A | 9/1973 | Coss |
| 4,051,596 A | 10/1977 | Hofmann |
| 4,203,444 A | 5/1980 | Bonnell et al. |
| 4,246,902 A | 1/1981 | Martinez |
| 4,274,414 A | 6/1981 | Johnson et al. |
| D267,145 S | 12/1982 | Kaneko |
| 4,471,777 A | 9/1984 | Mccorkle, Jr. |
| 4,517,977 A | 5/1985 | Frost |
| 4,582,056 A | 4/1986 | McCorkle et al. |
| 4,598,710 A | 7/1986 | Kleinberg et al. |
| 4,601,290 A | 7/1986 | Effron et al. |
| 4,646,738 A | 3/1987 | Trott |
| 4,662,869 A | 5/1987 | Wright |
| 4,674,502 A | 6/1987 | Imonti |
| 4,729,763 A | 3/1988 | Henrie |
| 4,754,755 A | 7/1988 | Husted |
| 4,767,403 A | 8/1988 | Hodge |
| 4,785,826 A | 11/1988 | Ward |
| D309,350 S | 7/1990 | Sutherland et al. |
| 4,943,289 A | 7/1990 | Goode et al. |
| 4,950,277 A | 8/1990 | Farr |
| 4,988,347 A | 1/1991 | Goode et al. |
| 5,011,482 A | 4/1991 | Goode et al. |
| 5,013,310 A | 5/1991 | Goode et al. |
| 5,031,634 A | 7/1991 | Simon |
| 5,152,744 A | 10/1992 | Krause et al. |
| 5,201,316 A | 4/1993 | Pomeranz et al. |
| 5,207,683 A | 5/1993 | Goode et al. |
| 5,217,454 A | 6/1993 | Khoury |
| 5,261,877 A | 11/1993 | Fine et al. |
| 5,263,928 A | 11/1993 | Trauthen et al. |
| 5,275,609 A | 1/1994 | Pingleton et al. |
| 5,281,220 A | 1/1994 | Blake et al. |
| 5,290,275 A | 3/1994 | Kittrell et al. |
| 5,290,303 A | 3/1994 | Pingleton et al. |
| 5,383,199 A | 1/1995 | Laudenslager et al. |
| 5,395,328 A | 3/1995 | Ockuly et al. |
| 5,411,513 A | 5/1995 | Ireland et al. |
| 5,423,330 A | 6/1995 | Lee |
| 5,423,806 A | 6/1995 | Dale et al. |
| 5,456,680 A | 10/1995 | Taylor et al. |
| 5,484,433 A | 1/1996 | Taylor et al. |
| 5,507,751 A | 4/1996 | Goode et al. |
| 5,562,694 A | 10/1996 | Sauer et al. |
| 5,569,284 A | 10/1996 | Young et al. |
| 5,575,797 A | 11/1996 | Neubauer et al. |
| 5,595,186 A | 1/1997 | Rubinstein et al. |
| 5,620,451 A | 4/1997 | Rosborough |
| 5,632,749 A | 5/1997 | Goode et al. |
| 5,651,781 A | 7/1997 | Grace |
| 5,697,936 A | 12/1997 | Shipko et al. |
| 5,718,237 A | 2/1998 | Haaga |
| 5,725,523 A | 3/1998 | Mueller |
| 5,766,164 A | 6/1998 | Mueller et al. |
| 5,782,823 A | 7/1998 | Mueller |
| 5,792,151 A | 8/1998 | Heck et al. |
| 5,807,399 A | 9/1998 | Laske et al. |
| 5,814,044 A | 9/1998 | Hooven |
| 5,823,971 A | 10/1998 | Robinson et al. |
| 5,824,026 A | 10/1998 | Diaz |
| 5,863,294 A | 1/1999 | Alden |
| 5,873,886 A | 2/1999 | Larsen et al. |
| 5,879,365 A | 3/1999 | Whitfield et al. |
| 5,893,862 A | 4/1999 | Pratt et al. |
| 5,899,915 A | 5/1999 | Saadat |
| 5,910,150 A | 6/1999 | Saadat |
| 5,916,210 A | 6/1999 | Winston |
| 5,931,848 A | 8/1999 | Saadat |
| 5,941,893 A | 8/1999 | Saadat |
| 5,951,581 A | 9/1999 | Saadat et al. |
| 5,972,012 A | 10/1999 | Ream et al. |
| 5,980,515 A | 11/1999 | Tu |
| 5,980,545 A | 11/1999 | Pacala et al. |
| 6,007,512 A | 12/1999 | Hooven |
| 6,010,476 A | 1/2000 | Saadat |
| 6,019,756 A | 2/2000 | Mueller et al. |
| 6,022,336 A | 2/2000 | Zadno-Azizi et al. |
| 6,027,497 A | 2/2000 | Daniel et al. |
| 6,033,402 A | 3/2000 | Tu et al. |
| 6,036,685 A | 3/2000 | Mueller |
| 6,039,748 A | 3/2000 | Savage et al. |
| 6,051,008 A | 4/2000 | Saadat et al. |
| 6,063,037 A | 5/2000 | Mittermeier et al. |
| 6,066,131 A | 5/2000 | Mueller et al. |
| 6,080,175 A | 6/2000 | Hogendijk |
| 6,083,237 A | 7/2000 | Huitema et al. |
| 6,099,537 A | 8/2000 | Sugai et al. |
| 6,102,926 A | 8/2000 | Tartaglia et al. |
| D430,781 S | 9/2000 | Hillegonds |
| 6,117,149 A | 9/2000 | Sorensen et al. |
| 6,120,520 A | 9/2000 | Saadat et al. |
| 6,126,654 A | 10/2000 | Giba et al. |
| 6,136,005 A | 10/2000 | Goode et al. |
| 6,139,543 A | 10/2000 | Esch et al. |
| 6,152,909 A | 11/2000 | Bagaoisan et al. |
| 6,152,918 A | 11/2000 | Padilla et al. |
| 6,156,049 A | 12/2000 | Lovato et al. |
| 6,159,203 A | 12/2000 | Sinofsky |
| 6,159,225 A | 12/2000 | Makower |
| 6,162,214 A | 12/2000 | Mueller et al. |
| 6,165,188 A | 12/2000 | Saadat et al. |
| 6,167,315 A | 12/2000 | Coe et al. |
| 6,174,307 B1 | 1/2001 | Daniel et al. |
| 6,190,352 B1 | 2/2001 | Haarala et al. |
| 6,190,353 B1 | 2/2001 | Makower et al. |
| 6,203,537 B1 | 3/2001 | Adrian |
| 6,210,400 B1 | 4/2001 | Hebert et al. |
| 6,228,076 B1 | 5/2001 | Winston et al. |
| 6,235,044 B1 | 5/2001 | Root et al. |
| 6,241,692 B1 | 6/2001 | Tu et al. |
| 6,245,011 B1 | 6/2001 | Dudda et al. |
| 6,251,121 B1 | 6/2001 | Saadat |
| 6,258,083 B1 | 7/2001 | Daniel et al. |
| 6,290,668 B1 | 9/2001 | Gregory et al. |
| 6,315,774 B1 | 11/2001 | Daniel et al. |
| 6,324,434 B2 | 11/2001 | Coe et al. |
| 6,379,351 B1 | 4/2002 | Thapliyal et al. |
| 6,395,002 B1 | 5/2002 | Ellman et al. |
| 6,398,773 B1 | 6/2002 | Bagaoisan et al. |
| 6,402,771 B1 | 6/2002 | Palmer et al. |
| 6,402,781 B1 | 6/2002 | Langberg et al. |
| 6,419,674 B1 | 7/2002 | Bowser et al. |

(56) References Cited

U.S. PATENT DOCUMENTS

| | | |
|---|---|---|
| 6,419,684 B1 | 7/2002 | Heisler et al. |
| 6,423,051 B1 | 7/2002 | Kaplan et al. |
| 6,428,539 B1 | 8/2002 | Baxter et al. |
| 6,428,556 B1 | 8/2002 | Chin |
| 6,432,119 B1 | 8/2002 | Saadat |
| 6,436,054 B1 | 8/2002 | Viola et al. |
| 6,436,114 B1 | 8/2002 | Novak et al. |
| 6,454,741 B1 | 9/2002 | Muni et al. |
| 6,454,758 B1 | 9/2002 | Thompson et al. |
| 6,461,349 B1 | 10/2002 | Elbrecht et al. |
| 6,478,777 B1 | 11/2002 | Honeck et al. |
| 6,488,636 B2 | 12/2002 | Bryan et al. |
| 6,500,182 B2 | 12/2002 | Foster |
| 6,512,959 B1 | 1/2003 | Gomperz et al. |
| 6,527,752 B1 | 3/2003 | Bosley et al. |
| 6,537,314 B2 | 3/2003 | Langberg et al. |
| 6,540,865 B2 | 4/2003 | Miekka et al. |
| 6,554,779 B2 | 4/2003 | Viola et al. |
| 6,558,382 B2 | 5/2003 | Jahns et al. |
| 6,565,588 B1 | 5/2003 | Clement et al. |
| 6,569,082 B1 | 5/2003 | Chin |
| 6,575,997 B1 | 6/2003 | Palmer et al. |
| 6,592,607 B1 | 7/2003 | Palmer et al. |
| 6,595,982 B2 | 7/2003 | Sekino et al. |
| 6,599,296 B1 | 7/2003 | Gillick et al. |
| 6,602,241 B2 | 8/2003 | Makower et al. |
| 6,607,547 B1 | 8/2003 | Chin |
| 6,610,046 B1 | 8/2003 | Usami et al. |
| 6,613,013 B2 | 9/2003 | Haarala et al. |
| 6,620,153 B2 | 9/2003 | Mueller et al. |
| 6,620,160 B2 | 9/2003 | Lewis et al. |
| 6,620,180 B1 | 9/2003 | Bays et al. |
| 6,641,590 B1 | 11/2003 | Palmer et al. |
| 6,652,480 B1 | 11/2003 | Imran et al. |
| 6,652,548 B2 | 11/2003 | Evans et al. |
| 6,660,021 B1 | 12/2003 | Palmer et al. |
| 6,663,626 B2 | 12/2003 | Truckai et al. |
| 6,669,685 B1 | 12/2003 | Rizoiu et al. |
| 6,673,090 B2 | 1/2004 | Root et al. |
| 6,687,548 B2 | 2/2004 | Goode |
| 6,702,813 B1 | 3/2004 | Baxter et al. |
| 6,706,018 B2 | 3/2004 | Westlund et al. |
| 6,706,052 B1 | 3/2004 | Chin |
| 6,706,065 B2 | 3/2004 | Langberg et al. |
| 6,709,456 B2 | 3/2004 | Langberg et al. |
| 6,712,773 B1 | 3/2004 | Viola |
| 6,712,826 B2 | 3/2004 | Lui |
| 6,772,014 B2 | 8/2004 | Coe et al. |
| 6,802,838 B2 | 10/2004 | Loeb et al. |
| 6,805,692 B2 | 10/2004 | Muni et al. |
| 6,810,882 B2 | 11/2004 | Langberg et al. |
| 6,818,001 B2 | 11/2004 | Wulfman et al. |
| 6,860,860 B2 | 3/2005 | Viola |
| 6,871,085 B2 | 3/2005 | Sommer |
| 6,884,240 B1 | 4/2005 | Dykes |
| 6,887,238 B2 | 5/2005 | Jahns et al. |
| 6,893,450 B2 | 5/2005 | Foster |
| 6,913,612 B2 | 7/2005 | Palmer et al. |
| 6,962,585 B2 | 11/2005 | Poleo et al. |
| 6,979,290 B2 | 12/2005 | Mourlas et al. |
| 6,979,319 B2 | 12/2005 | Manning et al. |
| 6,989,028 B2 | 1/2006 | Lashinski et al. |
| 6,999,809 B2 | 2/2006 | Currier et al. |
| 7,004,956 B2 | 2/2006 | Palmer et al. |
| 7,011,682 B2 | 3/2006 | Lashinski et al. |
| 7,014,614 B2 | 3/2006 | Casula |
| 7,022,133 B2 | 4/2006 | Yee et al. |
| 7,033,324 B2 | 4/2006 | Giusti et al. |
| 7,033,335 B2 | 4/2006 | Haarala et al. |
| 7,033,344 B2 | 4/2006 | Imran |
| 7,033,357 B2 | 4/2006 | Baxter et al. |
| 7,060,061 B2 | 6/2006 | Altshuler et al. |
| 7,063,693 B2 | 6/2006 | Guenst |
| 7,077,856 B2 | 7/2006 | Whitman |
| 7,092,765 B2 | 8/2006 | Geske et al. |
| 7,104,983 B2 | 9/2006 | Grasso et al. |
| 7,114,642 B2 | 10/2006 | Whitman |
| 7,117,039 B2 | 10/2006 | Manning et al. |
| 7,149,587 B2 | 12/2006 | Wardle et al. |
| 7,151,965 B2 | 12/2006 | Osypka |
| 7,189,207 B2 | 3/2007 | Viola |
| 7,191,015 B2 | 3/2007 | Lamson et al. |
| 7,192,430 B2 | 3/2007 | Truckai et al. |
| 7,204,824 B2 | 4/2007 | Moulis |
| 7,214,180 B2 | 5/2007 | Chin |
| 7,226,459 B2 | 6/2007 | Cesarini et al. |
| 7,238,179 B2 | 7/2007 | Brucker et al. |
| 7,238,180 B2 | 7/2007 | Mester et al. |
| 7,252,641 B2 | 8/2007 | Thompson et al. |
| 7,264,587 B2 | 9/2007 | Chin |
| 7,273,478 B2 | 9/2007 | Appling et al. |
| 7,276,052 B2 | 10/2007 | Kobayashi et al. |
| 7,288,096 B2 | 10/2007 | Chin |
| 7,296,577 B2 | 11/2007 | Lashinski et al. |
| 7,306,588 B2 | 12/2007 | Loeb et al. |
| 7,326,226 B2 | 2/2008 | Root et al. |
| 7,328,071 B1 | 2/2008 | Stehr et al. |
| 7,344,546 B2 | 3/2008 | Wulfman et al. |
| 7,357,794 B2 | 4/2008 | Makower et al. |
| 7,359,756 B2 | 4/2008 | Goode |
| 7,369,901 B1 | 5/2008 | Morgan et al. |
| 7,396,354 B2 | 7/2008 | Rychnovsky et al. |
| 7,398,781 B1 | 7/2008 | Chin |
| 7,449,010 B1 | 11/2008 | Hayase et al. |
| 7,462,167 B2 | 12/2008 | Kratz et al. |
| 7,485,127 B2 | 2/2009 | Nistal |
| 7,494,484 B2 | 2/2009 | Beck et al. |
| 7,507,252 B2 | 3/2009 | Lashinski et al. |
| 7,509,169 B2 | 3/2009 | Eigler et al. |
| 7,510,576 B2 | 3/2009 | Langberg et al. |
| 7,513,877 B2 | 4/2009 | Viola |
| 7,513,892 B1 | 4/2009 | Haarala et al. |
| 7,526,342 B2 | 4/2009 | Chin et al. |
| 7,537,602 B2 | 5/2009 | Whitman |
| D594,983 S | 6/2009 | Price et al. |
| 7,540,865 B2 | 6/2009 | Griffin et al. |
| 7,544,197 B2 | 6/2009 | Kelsch et al. |
| 7,559,941 B2 | 7/2009 | Zannis et al. |
| D600,792 S | 9/2009 | Eubanks et al. |
| 7,591,790 B2 | 9/2009 | Pflueger |
| 7,597,698 B2 | 10/2009 | Chin |
| 7,606,615 B2 | 10/2009 | Makower et al. |
| 7,611,474 B2 | 11/2009 | Hibner et al. |
| 7,637,904 B2 | 12/2009 | Wingler et al. |
| 7,645,286 B2 | 1/2010 | Catanese et al. |
| 7,648,466 B2 | 1/2010 | Stephens et al. |
| 7,651,503 B1 | 1/2010 | Coe et al. |
| 7,651,504 B2 | 1/2010 | Goode et al. |
| D610,259 S | 2/2010 | Way et al. |
| D611,146 S | 3/2010 | Way et al. |
| 7,674,272 B2 | 3/2010 | Torrance et al. |
| 7,695,485 B2 | 4/2010 | Whitman et al. |
| 7,695,512 B2 | 4/2010 | Lashinski et al. |
| 7,697,996 B2 | 4/2010 | Manning et al. |
| 7,713,231 B2 | 5/2010 | Wulfman et al. |
| 7,713,235 B2 | 5/2010 | Torrance et al. |
| 7,713,281 B2 | 5/2010 | Leeflang et al. |
| 7,722,549 B2 | 5/2010 | Nakao |
| 7,740,626 B2 | 6/2010 | Takayama et al. |
| 7,743,960 B2 | 6/2010 | Whitman et al. |
| D619,252 S | 7/2010 | Way et al. |
| D619,253 S | 7/2010 | Way et al. |
| 7,758,594 B2 | 7/2010 | Lamson et al. |
| 7,758,613 B2 | 7/2010 | Whitman |
| D621,939 S | 8/2010 | Way et al. |
| 7,766,923 B2 | 8/2010 | Catanese et al. |
| 7,780,682 B2 | 8/2010 | Catanese et al. |
| 7,780,694 B2 | 8/2010 | Palmer et al. |
| 7,794,411 B2 | 9/2010 | Ritchart et al. |
| 7,798,813 B1 | 9/2010 | Harrel |
| 7,803,151 B2 | 9/2010 | Whitman |
| 7,806,835 B2 | 10/2010 | Hibner et al. |
| 7,811,281 B1 | 10/2010 | Rentrop |
| 7,815,655 B2 | 10/2010 | Catanese et al. |

(56) References Cited

U.S. PATENT DOCUMENTS

| | | |
|---|---|---|
| 7,842,009 B2 | 11/2010 | Torrance et al. |
| 7,845,538 B2 | 12/2010 | Whitman |
| 7,858,038 B2 | 12/2010 | Andreyko et al. |
| D631,155 S | 1/2011 | Peine et al. |
| 7,875,018 B2 | 1/2011 | Tockman et al. |
| 7,875,049 B2 | 1/2011 | Eversull et al. |
| D631,965 S | 2/2011 | Price et al. |
| 7,890,186 B2 | 2/2011 | Wardle et al. |
| 7,890,192 B1 | 2/2011 | Kelsch et al. |
| 7,896,879 B2 | 3/2011 | Solsberg et al. |
| 7,896,891 B2 | 3/2011 | Catanese et al. |
| 7,905,889 B2 | 3/2011 | Catanese et al. |
| 7,909,836 B2 | 3/2011 | McLean et al. |
| 7,914,464 B2 | 3/2011 | Burdorff et al. |
| 7,914,542 B2 | 3/2011 | Lamson et al. |
| D635,671 S | 4/2011 | Way et al. |
| 7,918,230 B2 | 4/2011 | Whitman et al. |
| 7,918,803 B2 | 4/2011 | Ritchart et al. |
| 7,930,040 B1 | 4/2011 | Kelsch et al. |
| D638,935 S | 5/2011 | Gilmore et al. |
| 7,935,146 B2 | 5/2011 | Langberg et al. |
| 7,938,786 B2 | 5/2011 | Ritchie et al. |
| 7,942,830 B2 | 5/2011 | Solsberg et al. |
| 7,951,071 B2 | 5/2011 | Whitman et al. |
| 7,951,158 B2 | 5/2011 | Catanese et al. |
| 7,963,040 B2 | 6/2011 | Shan et al. |
| 7,963,433 B2 | 6/2011 | Whitman et al. |
| 7,974,710 B2 | 7/2011 | Seifert |
| 7,981,049 B2 | 7/2011 | Ritchie et al. |
| 7,981,050 B2 | 7/2011 | Ritchart et al. |
| 7,981,128 B2 | 7/2011 | To et al. |
| 7,988,726 B2 | 8/2011 | Langberg et al. |
| 7,991,258 B2 | 8/2011 | Temelkuran et al. |
| 7,992,758 B2 | 8/2011 | Whitman et al. |
| 7,993,350 B2 | 8/2011 | Ventura et al. |
| 7,993,351 B2 | 8/2011 | Worley et al. |
| 7,993,359 B1 | 8/2011 | Atwell et al. |
| 8,007,469 B2 | 8/2011 | Duffy |
| 8,007,488 B2 | 8/2011 | Ravenscroft |
| 8,007,503 B2 | 8/2011 | Catanese et al. |
| 8,007,506 B2 | 8/2011 | To et al. |
| 8,016,748 B2 | 9/2011 | Mourlas et al. |
| 8,016,844 B2 | 9/2011 | Privitera et al. |
| 8,016,855 B2 | 9/2011 | Whitman et al. |
| 8,016,858 B2 | 9/2011 | Whitman |
| 8,021,373 B2 | 9/2011 | Whitman et al. |
| 8,025,199 B2 | 9/2011 | Whitman et al. |
| 8,043,309 B2 | 10/2011 | Catanese et al. |
| RE42,959 E | 11/2011 | Saadat et al. |
| 8,052,616 B2 | 11/2011 | Andrisek et al. |
| 8,052,659 B2 | 11/2011 | Ravenscroft et al. |
| 8,056,786 B2 | 11/2011 | Whitman et al. |
| 8,056,791 B2 | 11/2011 | Whitman |
| D650,074 S | 12/2011 | Hunt et al. |
| 8,070,762 B2 | 12/2011 | Escudero et al. |
| 8,090,430 B2 | 1/2012 | Makower et al. |
| 8,097,012 B2 | 1/2012 | Kagarise |
| 8,100,920 B2 | 1/2012 | Gambale et al. |
| 8,118,208 B2 | 2/2012 | Whitman |
| 8,126,570 B2 | 2/2012 | Manning et al. |
| 8,128,577 B2 | 3/2012 | Viola |
| 8,128,636 B2 | 3/2012 | Lui et al. |
| 8,133,214 B2 | 3/2012 | Hayase et al. |
| 8,137,377 B2 | 3/2012 | Palmer et al. |
| 8,142,442 B2 | 3/2012 | Palmer et al. |
| 8,142,446 B2 | 3/2012 | Shan |
| RE43,300 E | 4/2012 | Saadat et al. |
| 8,157,815 B2 | 4/2012 | Catanese et al. |
| 8,186,559 B1 | 5/2012 | Whitman |
| 8,187,204 B2 | 5/2012 | Miller et al. |
| 8,192,430 B2 | 6/2012 | Goode et al. |
| 8,202,229 B2 | 6/2012 | Miller et al. |
| 8,206,409 B2 | 6/2012 | Privitera et al. |
| 8,211,118 B2 | 7/2012 | Catanese et al. |
| 8,216,254 B2 | 7/2012 | McLean et al. |
| 8,235,916 B2 | 8/2012 | Whiting et al. |
| 8,236,016 B2 | 8/2012 | To et al. |
| 8,239,039 B2 | 8/2012 | Zarembo et al. |
| 8,241,272 B2 | 8/2012 | Arnold et al. |
| 8,251,916 B2 | 8/2012 | Speeg et al. |
| 8,252,015 B2 | 8/2012 | Leeflang et al. |
| 8,257,312 B2 | 9/2012 | Duffy |
| 8,272,554 B2 | 9/2012 | Whitman et al. |
| 8,273,078 B2 | 9/2012 | Muenker |
| 8,295,947 B2 | 10/2012 | Lamson et al. |
| 8,303,511 B2 | 11/2012 | Eigler et al. |
| 8,303,570 B2 | 11/2012 | Gregorich et al. |
| 8,323,240 B2 | 12/2012 | Wulfman et al. |
| 8,326,437 B2 | 12/2012 | Cully et al. |
| 8,333,740 B2 | 12/2012 | Shippert |
| 8,333,776 B2 | 12/2012 | Cheng et al. |
| 8,337,516 B2 | 12/2012 | Escudero et al. |
| 8,343,167 B2 | 1/2013 | Henson |
| 8,343,187 B2 | 1/2013 | Lamson et al. |
| 8,353,899 B1 | 1/2013 | Wells et al. |
| 8,361,094 B2 | 1/2013 | To et al. |
| 8,364,280 B2 | 1/2013 | Marnfeldt et al. |
| 8,372,098 B2 | 2/2013 | Tran |
| D679,010 S | 3/2013 | Kitayama et al. |
| 8,394,110 B2 | 3/2013 | Catanese, Iii et al. |
| 8,394,113 B2 | 3/2013 | Wei et al. |
| 8,424,535 B2 | 4/2013 | Hessler et al. |
| 8,425,535 B2 | 4/2013 | McLean et al. |
| D687,549 S | 8/2013 | Johnson et al. |
| D697,618 S | 1/2014 | Gonzales et al. |
| 8,622,275 B2 | 1/2014 | Baxter et al. |
| D706,928 S | 6/2014 | Harrison et al. |
| D708,742 S | 7/2014 | Dallemagne et al. |
| 8,961,551 B2 | 2/2015 | Taylor |
| 9,028,520 B2 | 5/2015 | Taylor et al. |
| 9,232,945 B2 | 1/2016 | Zingman |
| 9,283,040 B2 | 3/2016 | Hendrick et al. |
| 9,289,226 B2 | 3/2016 | Taylor |
| D765,243 S | 8/2016 | Halbert |
| D786,430 S | 5/2017 | Davies et al. |
| 2001/0005789 A1 | 6/2001 | Root et al. |
| 2001/0016717 A1 | 8/2001 | Haarala et al. |
| 2001/0025174 A1 | 9/2001 | Daniel et al. |
| 2001/0031981 A1 | 10/2001 | Evans et al. |
| 2001/0039427 A1 | 11/2001 | Dinger et al. |
| 2001/0041899 A1 | 11/2001 | Foster |
| 2001/0044568 A1 | 11/2001 | Langberg et al. |
| 2002/0002372 A1 | 1/2002 | Jahns et al. |
| 2002/0007204 A1 | 1/2002 | Goode |
| 2002/0010475 A1 | 1/2002 | Lui |
| 2002/0010487 A1 | 1/2002 | Evans et al. |
| 2002/0016628 A1 | 2/2002 | Langberg et al. |
| 2002/0045811 A1 | 4/2002 | Kittrell et al. |
| 2002/0065543 A1 | 5/2002 | Gomperz et al. |
| 2002/0068954 A1 | 6/2002 | Foster |
| 2002/0087151 A1 | 7/2002 | Mody et al. |
| 2002/0103459 A1 | 8/2002 | Sparks et al. |
| 2002/0103477 A1 | 8/2002 | Grasso et al. |
| 2002/0103532 A1 | 8/2002 | Langberg et al. |
| 2002/0103533 A1 | 8/2002 | Langberg et al. |
| 2002/0123785 A1 | 9/2002 | Zhang et al. |
| 2002/0151961 A1 | 10/2002 | Lashinski et al. |
| 2002/0165425 A1 | 11/2002 | Yoon et al. |
| 2002/0183735 A1 | 12/2002 | Edwards et al. |
| 2002/0188278 A1 | 12/2002 | Tockman et al. |
| 2003/0009146 A1 | 1/2003 | Muni et al. |
| 2003/0036788 A1 | 2/2003 | Coe et al. |
| 2003/0050630 A1 | 3/2003 | Mody et al. |
| 2003/0050631 A1 | 3/2003 | Mody et al. |
| 2003/0055444 A1 | 3/2003 | Evans et al. |
| 2003/0055445 A1 | 3/2003 | Evans et al. |
| 2003/0069575 A1 | 4/2003 | Chin et al. |
| 2003/0073985 A1 | 4/2003 | Mueller et al. |
| 2003/0078562 A1 | 4/2003 | Makower et al. |
| 2003/0105451 A1 | 6/2003 | Westlund et al. |
| 2003/0125619 A1 | 7/2003 | Manning et al. |
| 2003/0167056 A1 | 9/2003 | Jahns et al. |
| 2003/0187460 A1 | 10/2003 | Chin et al. |
| 2003/0187461 A1 | 10/2003 | Chin |

(56) References Cited

U.S. PATENT DOCUMENTS

| | | |
|---|---|---|
| 2003/0199916 A1 | 10/2003 | Yee et al. |
| 2003/0199921 A1 | 10/2003 | Palmer et al. |
| 2003/0204202 A1 | 10/2003 | Palmer et al. |
| 2003/0208209 A1 | 11/2003 | Gambale et al. |
| 2003/0229323 A1 | 12/2003 | Haarala et al. |
| 2003/0229353 A1 | 12/2003 | Cragg |
| 2004/0006358 A1 | 1/2004 | Wulfman et al. |
| 2004/0010248 A1 | 1/2004 | Appling et al. |
| 2004/0015193 A1 | 1/2004 | Lamson et al. |
| 2004/0019359 A1 | 1/2004 | Worley et al. |
| 2004/0049208 A1 | 3/2004 | Hill et al. |
| 2004/0054368 A1 | 3/2004 | Truckai et al. |
| 2004/0054388 A1 | 3/2004 | Osypka |
| 2004/0059348 A1 | 3/2004 | Geske et al. |
| 2004/0064024 A1 | 4/2004 | Sommer |
| 2004/0068256 A1 | 4/2004 | Rizoiu et al. |
| 2004/0068288 A1 | 4/2004 | Palmer et al. |
| 2004/0093016 A1 | 5/2004 | Root et al. |
| 2004/0102804 A1 | 5/2004 | Chin |
| 2004/0102841 A1 | 5/2004 | Langberg et al. |
| 2004/0111101 A1 | 6/2004 | Chin |
| 2004/0116939 A1 | 6/2004 | Goode |
| 2004/0133220 A1 | 7/2004 | Lashinski et al. |
| 2004/0138562 A1 | 7/2004 | Makower et al. |
| 2004/0138744 A1 | 7/2004 | Lashinski et al. |
| 2004/0143284 A1 | 7/2004 | Chin |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0153096 A1 | 8/2004 | Goode et al. |
| 2004/0153098 A1 | 8/2004 | Chin et al. |
| 2004/0172116 A1 | 9/2004 | Seifert et al. |
| 2004/0176840 A1 | 9/2004 | Langberg et al. |
| 2004/0181249 A1 | 9/2004 | Torrance et al. |
| 2004/0216748 A1 | 11/2004 | Chin |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0235611 A1 | 11/2004 | Nistal |
| 2004/0236312 A1 | 11/2004 | Nistal et al. |
| 2004/0236397 A1 | 11/2004 | Coe et al. |
| 2004/0243123 A1 | 12/2004 | Grasso et al. |
| 2004/0243162 A1 | 12/2004 | Wulfman et al. |
| 2004/0254534 A1 | 12/2004 | Bjorkman et al. |
| 2004/0260322 A1 | 12/2004 | Rudko et al. |
| 2004/0267276 A1 | 12/2004 | Camino et al. |
| 2004/0267304 A1 | 12/2004 | Zannis et al. |
| 2005/0004644 A1 | 1/2005 | Kelsch et al. |
| 2005/0025798 A1 | 2/2005 | Moulis |
| 2005/0027337 A1 | 2/2005 | Rudko et al. |
| 2005/0038419 A9 | 2/2005 | Arnold et al. |
| 2005/0054948 A1 | 3/2005 | Goldenberg |
| 2005/0060030 A1 | 3/2005 | Lashinski et al. |
| 2005/0065561 A1 | 3/2005 | Manning et al. |
| 2005/0090748 A1 | 4/2005 | Makower et al. |
| 2005/0096740 A1 | 5/2005 | Langberg et al. |
| 2005/0131399 A1 | 6/2005 | Loeb et al. |
| 2005/0149104 A1 | 7/2005 | Leeflang et al. |
| 2005/0149105 A1 | 7/2005 | Leeflang et al. |
| 2005/0197623 A1 | 9/2005 | Leeflang et al. |
| 2005/0222607 A1 | 10/2005 | Palmer et al. |
| 2005/0228402 A1 | 10/2005 | Hofmann |
| 2005/0228452 A1 | 10/2005 | Mourlas et al. |
| 2005/0251116 A1 | 11/2005 | Steinke et al. |
| 2005/0259942 A1 | 11/2005 | Temelkuran et al. |
| 2005/0267557 A1 | 12/2005 | Flynn et al. |
| 2005/0273090 A1 | 12/2005 | Nieman et al. |
| 2005/0283143 A1 | 12/2005 | Rizoiu |
| 2005/0288596 A1 | 12/2005 | Eigler et al. |
| 2005/0288604 A1 | 12/2005 | Eigler et al. |
| 2005/0288654 A1 | 12/2005 | Nieman et al. |
| 2006/0041250 A1 | 2/2006 | Poleo |
| 2006/0052660 A1 | 3/2006 | Chin |
| 2006/0084839 A1 | 4/2006 | Mourlas et al. |
| 2006/0100663 A1 | 5/2006 | Palmer et al. |
| 2006/0100687 A1 | 5/2006 | Fahey et al. |
| 2006/0116746 A1 | 6/2006 | Chin |
| 2006/0116757 A1 | 6/2006 | Lashinski et al. |
| 2006/0167417 A1 | 7/2006 | Kratz et al. |
| 2006/0173440 A1 | 8/2006 | Lamson et al. |
| 2006/0217755 A1 | 9/2006 | Eversull et al. |
| 2006/0229490 A1 | 10/2006 | Chin |
| 2006/0235431 A1 | 10/2006 | Goode et al. |
| 2006/0247751 A1 | 11/2006 | Seifert |
| 2006/0253179 A1 | 11/2006 | Goode et al. |
| 2006/0265042 A1 | 11/2006 | Catanese et al. |
| 2006/0276871 A1 | 12/2006 | Lamson et al. |
| 2006/0287574 A1 | 12/2006 | Chin |
| 2007/0015964 A1 | 1/2007 | Eversull et al. |
| 2007/0016130 A1 | 1/2007 | Leeflang et al. |
| 2007/0021812 A1 | 1/2007 | Manning et al. |
| 2007/0049929 A1 | 3/2007 | Catanese et al. |
| 2007/0050003 A1 | 3/2007 | Zarembo et al. |
| 2007/0083217 A1 | 4/2007 | Eversull et al. |
| 2007/0100410 A1 | 5/2007 | Lamson et al. |
| 2007/0106328 A1 | 5/2007 | Wardle et al. |
| 2007/0123892 A1 | 5/2007 | Ries et al. |
| 2007/0129710 A1 | 6/2007 | Rudko et al. |
| 2007/0142846 A1 | 6/2007 | Catanese et al. |
| 2007/0197861 A1 | 8/2007 | Reiley et al. |
| 2007/0198020 A1 | 8/2007 | Reiley et al. |
| 2007/0232981 A1 | 10/2007 | Ravenscroft et al. |
| 2007/0276412 A1 | 11/2007 | Catanese et al. |
| 2007/0276419 A1 | 11/2007 | Rosenthal |
| 2007/0293853 A1 | 12/2007 | Truckai et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0015625 A1 | 1/2008 | Ventura et al. |
| 2008/0021484 A1 | 1/2008 | Catanese et al. |
| 2008/0021485 A1 | 1/2008 | Catanese et al. |
| 2008/0033232 A1 | 2/2008 | Catanese et al. |
| 2008/0033456 A1 | 2/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039876 A1 | 2/2008 | Catanese et al. |
| 2008/0039883 A1 | 2/2008 | Nohilly |
| 2008/0039884 A1 | 2/2008 | Nohilly et al. |
| 2008/0039889 A1 | 2/2008 | Lamson et al. |
| 2008/0039893 A1 | 2/2008 | McLean et al. |
| 2008/0039894 A1 | 2/2008 | Catanese et al. |
| 2008/0045986 A1 | 2/2008 | To et al. |
| 2008/0051756 A1 | 2/2008 | Makower et al. |
| 2008/0058759 A1 | 3/2008 | Makower et al. |
| 2008/0071341 A1 | 3/2008 | Goode et al. |
| 2008/0071342 A1 | 3/2008 | Goode et al. |
| 2008/0097398 A1 | 4/2008 | Mitelberg et al. |
| 2008/0097426 A1 | 4/2008 | Root et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0125748 A1 | 5/2008 | Patel |
| 2008/0147061 A1 | 6/2008 | Goode et al. |
| 2008/0154293 A1 | 6/2008 | Taylor |
| 2008/0154296 A1 | 6/2008 | Taylor et al. |
| 2008/0183163 A1 | 7/2008 | Lampropoulos et al. |
| 2008/0208105 A1 | 8/2008 | Zelickson et al. |
| 2008/0221560 A1 | 9/2008 | Arai et al. |
| 2008/0228208 A1 | 9/2008 | Wulfman et al. |
| 2008/0234602 A1 | 9/2008 | Oostman et al. |
| 2008/0234698 A1 | 9/2008 | Oostman et al. |
| 2008/0234716 A1 | 9/2008 | Kiester |
| 2008/0249516 A1 | 10/2008 | Muenker |
| 2008/0262516 A1 | 10/2008 | Gambale et al. |
| 2008/0275497 A1 | 11/2008 | Palmer et al. |
| 2008/0275498 A1 | 11/2008 | Palmer et al. |
| 2008/0277445 A1 | 11/2008 | Zergiebel et al. |
| 2008/0281308 A1 | 11/2008 | Neuberger et al. |

(56) References Cited

U.S. PATENT DOCUMENTS

| | | |
|---|---|---|
| 2008/0287888 A1 | 11/2008 | Ravenscroft |
| 2008/0306333 A1 | 12/2008 | Chin |
| 2009/0012510 A1 | 1/2009 | Bertolero et al. |
| 2009/0018523 A1 | 1/2009 | Lamson et al. |
| 2009/0018553 A1 | 1/2009 | McLean et al. |
| 2009/0034927 A1 | 2/2009 | Temelkuran et al. |
| 2009/0036871 A1 | 2/2009 | Hayase et al. |
| 2009/0054918 A1 | 2/2009 | Henson |
| 2009/0060977 A1 | 3/2009 | Lamson et al. |
| 2009/0071012 A1 | 3/2009 | Shan et al. |
| 2009/0076522 A1 | 3/2009 | Shan |
| 2009/0131907 A1 | 5/2009 | Chin et al. |
| 2009/0157045 A1 | 6/2009 | Haarala et al. |
| 2009/0192439 A1 | 7/2009 | Lamson et al. |
| 2009/0204128 A1 | 8/2009 | Lamson et al. |
| 2009/0221994 A1 | 9/2009 | Neuberger et al. |
| 2009/0222025 A1 | 9/2009 | Catanese et al. |
| 2009/0227999 A1 | 9/2009 | Willis et al. |
| 2009/0234378 A1 | 9/2009 | Escudero et al. |
| 2009/0270862 A1 | 10/2009 | Arcenio |
| 2009/0270898 A1 | 10/2009 | Chin et al. |
| 2010/0004606 A1 | 1/2010 | Hansen et al. |
| 2010/0030154 A1 | 2/2010 | Duffy |
| 2010/0030161 A1 | 2/2010 | Duffy |
| 2010/0030248 A1 | 2/2010 | Palmer et al. |
| 2010/0030262 A1 | 2/2010 | McLean et al. |
| 2010/0030263 A1 | 2/2010 | Cheng et al. |
| 2010/0049225 A1 | 2/2010 | To et al. |
| 2010/0063488 A1 | 3/2010 | Fischer et al. |
| 2010/0125253 A1 | 5/2010 | Olson et al. |
| 2010/0137873 A1 | 6/2010 | Grady et al. |
| 2010/0160952 A1 | 6/2010 | Leeflang et al. |
| 2010/0191165 A1 | 7/2010 | Appling et al. |
| 2010/0198194 A1 | 8/2010 | Manning et al. |
| 2010/0198229 A1 | 8/2010 | Olomutzki et al. |
| 2010/0217081 A1 | 8/2010 | Deppmeier et al. |
| 2010/0217277 A1 | 8/2010 | Truong |
| 2010/0222737 A1 | 9/2010 | Arnold et al. |
| 2010/0222787 A1 | 9/2010 | Goode et al. |
| 2010/0240951 A1 | 9/2010 | Catanese et al. |
| 2010/0256616 A1 | 10/2010 | Kaloh et al. |
| 2010/0280496 A1 | 11/2010 | Shippert |
| 2010/0305594 A1 | 12/2010 | Opie |
| 2010/0324472 A1 | 12/2010 | Wulfman |
| 2010/0331793 A1 | 12/2010 | Tulleken |
| 2011/0004238 A1 | 1/2011 | Palmer et al. |
| 2011/0009957 A1 | 1/2011 | Langberg et al. |
| 2011/0022057 A1 | 1/2011 | Eigler et al. |
| 2011/0028959 A1 | 2/2011 | Chasan |
| 2011/0034790 A1 | 2/2011 | Mourlas et al. |
| 2011/0040238 A1 | 2/2011 | Wulfman et al. |
| 2011/0040312 A1 | 2/2011 | Lamson et al. |
| 2011/0040315 A1 | 2/2011 | To et al. |
| 2011/0040326 A1 | 2/2011 | Wei et al. |
| 2011/0046648 A1 | 2/2011 | Johnston et al. |
| 2011/0054493 A1 | 3/2011 | McLean et al. |
| 2011/0060349 A1 | 3/2011 | Cheng et al. |
| 2011/0071440 A1 | 3/2011 | Torrance et al. |
| 2011/0105947 A1 | 5/2011 | Fritscher-Ravens et al. |
| 2011/0106004 A1 | 5/2011 | Eubanks et al. |
| 2011/0106099 A1 | 5/2011 | Duffy et al. |
| 2011/0112548 A1 | 5/2011 | Fifer et al. |
| 2011/0112562 A1 | 5/2011 | Torrance |
| 2011/0112563 A1 | 5/2011 | To et al. |
| 2011/0112564 A1 | 5/2011 | Wolf |
| 2011/0118660 A1 | 5/2011 | Torrance et al. |
| 2011/0144423 A1 | 6/2011 | Tong et al. |
| 2011/0144425 A1 | 6/2011 | Catanese et al. |
| 2011/0151463 A1 | 6/2011 | Wulfman |
| 2011/0152607 A1 | 6/2011 | Catanese et al. |
| 2011/0152906 A1 | 6/2011 | Escudero et al. |
| 2011/0152907 A1 | 6/2011 | Escudero et al. |
| 2011/0160747 A1 | 6/2011 | McLean et al. |
| 2011/0160748 A1 | 6/2011 | Catanese et al. |
| 2011/0166564 A1 | 7/2011 | Merrick et al. |
| 2011/0178543 A1 | 7/2011 | Chin et al. |
| 2011/0190758 A1 | 8/2011 | Lamson et al. |
| 2011/0196298 A1 | 8/2011 | Anderson et al. |
| 2011/0196355 A1 | 8/2011 | Mitchell et al. |
| 2011/0208207 A1 | 8/2011 | Bowe et al. |
| 2011/0213398 A1 | 9/2011 | Chin et al. |
| 2011/0218528 A1 | 9/2011 | Ogata et al. |
| 2011/0238078 A1 | 9/2011 | Goode et al. |
| 2011/0238102 A1 | 9/2011 | Gutlinger et al. |
| 2011/0245751 A1 | 10/2011 | Hofmann |
| 2011/0257592 A1 | 10/2011 | Ventura et al. |
| 2011/0270169 A1 | 11/2011 | Gardeski et al. |
| 2011/0270170 A1 | 11/2011 | Gardeski et al. |
| 2011/0270289 A1 | 11/2011 | To et al. |
| 2011/0300010 A1 | 12/2011 | Jarnagin et al. |
| 2011/0301417 A1 | 12/2011 | Mourlas et al. |
| 2011/0301626 A1 | 12/2011 | To et al. |
| 2012/0029278 A1 | 2/2012 | Sato et al. |
| 2012/0035590 A1 | 2/2012 | Whiting et al. |
| 2012/0041422 A1 | 2/2012 | Whiting et al. |
| 2012/0053564 A1 | 3/2012 | Ravenscroft |
| 2012/0065659 A1 | 3/2012 | To |
| 2012/0083810 A1 | 4/2012 | Escudero et al. |
| 2012/0083826 A1 | 4/2012 | Chao et al. |
| 2012/0095447 A1 | 4/2012 | Fojtik |
| 2012/0095479 A1 | 4/2012 | Bowe et al. |
| 2012/0097174 A1 | 4/2012 | Spotnitz et al. |
| 2012/0123411 A1 | 5/2012 | Ibrahim et al. |
| 2012/0136341 A1 | 5/2012 | Appling et al. |
| 2012/0165827 A1 | 6/2012 | Khairkhahan et al. |
| 2012/0165861 A1 | 6/2012 | Palmer et al. |
| 2012/0191015 A1 | 7/2012 | Zannis et al. |
| 2012/0209173 A1 | 8/2012 | Hayase et al. |
| 2012/0215305 A1 | 8/2012 | Le et al. |
| 2012/0239008 A1 | 9/2012 | Fojtik |
| 2012/0245600 A1 | 9/2012 | McLean et al. |
| 2012/0253229 A1 | 10/2012 | Cage |
| 2012/0265183 A1 | 10/2012 | Tulleken et al. |
| 2012/0323252 A1 | 12/2012 | Booker |
| 2012/0323253 A1 | 12/2012 | Garai et al. |
| 2012/0330292 A1 | 12/2012 | Shadduck et al. |
| 2013/0006167 A1 | 1/2013 | Alvarez et al. |
| 2013/0006228 A1 | 1/2013 | Johnson et al. |
| 2013/0035676 A1 | 2/2013 | Mitchell et al. |
| 2013/0096582 A1 | 4/2013 | Cheng et al. |
| 2013/0103047 A1 | 4/2013 | Steingisser et al. |
| 2013/0131548 A1 | 5/2013 | McGhie et al. |
| 2014/0277037 A1 | 9/2014 | Grace et al. |
| 2015/0105796 A1 | 4/2015 | Grace |
| 2015/0164530 A1 | 6/2015 | Carver et al. |
| 2015/0196297 A1 | 7/2015 | (Prommersberger) Stopek |
| 2015/0258333 A1 | 9/2015 | Carver et al. |
| 2015/0305744 A1 | 10/2015 | Moore et al. |
| 2015/0342680 A1 | 12/2015 | Schneider |
| 2016/0120562 A1 | 5/2016 | Taylor |
| 2016/0361080 A1 | 12/2016 | Grace et al. |

FOREIGN PATENT DOCUMENTS

| | | |
|---|---|---|
| WO | 1995033513 A1 | 12/1995 |
| WO | 1999007295 A1 | 2/1999 |
| WO | 1999049937 A1 | 10/1999 |
| WO | 1999058066 A1 | 11/1999 |
| WO | 2001076680 A1 | 10/2001 |
| WO | 2002049690 A9 | 5/2003 |
| WO | 2004049956 A2 | 6/2004 |
| WO | 2004516073 A | 6/2004 |
| WO | 2004080345 A2 | 9/2004 |
| WO | 2004080507 A2 | 9/2004 |
| WO | 2006007410 A2 | 1/2006 |
| WO | 2008005888 A2 | 1/2008 |
| WO | 2008005891 A2 | 1/2008 |
| WO | 2008042987 A2 | 4/2008 |
| WO | 2009005779 A1 | 1/2009 |
| WO | 2009054968 A1 | 4/2009 |
| WO | 2009065082 A1 | 5/2009 |
| WO | 2009126309 A2 | 10/2009 |
| WO | 2011003113 A1 | 1/2011 |
| WO | 2011084863 A2 | 7/2011 |

(56) References Cited

FOREIGN PATENT DOCUMENTS

| WO | 2011133941 A2 | 10/2011 |
|---|---|---|
| WO | 2011162595 A1 | 12/2011 |
| WO | 2012040239 A1 | 3/2012 |
| WO | 2012009697 A4 | 4/2012 |
| WO | 2012098335 A1 | 7/2012 |
| WO | 2012114333 A1 | 8/2012 |
| WO | 2012177117 A1 | 12/2012 |
| WO | 2013036588 A1 | 3/2013 |
| WO | 2014151814 A1 | 9/2014 |

OTHER PUBLICATIONS

U.S. Appl. No. 14/725,781 entitled Surgical Instrument for Removing an Implanted Object, filed May 29, 2015.
Design U.S. Appl. No. 29/519,239 entitled Medical Device Handle, filed Mar. 3, 2015.
Design U.S. Appl. No. 29/519,258 entitled Medical Device Handle, filed Mar. 3, 2015.
U.S. Appl. No. 15/442,006 entitled Medical Device for Removing an Implanted Object, filed Feb. 24, 2017.
U.S. Appl. No. 15/406,033 entitled Medical Device for Removing an Implanted Object, filed Jan. 13, 2017.
U.S. Appl. No. 15/462,357 entitled Medical Device for Removing an Implanted Object, filed Mar. 17, 2017.
U.S. Appl. No. 61/793,597 entitled Surgical Instrument for Removing an Implanted Object filed Mar. 15, 2013.
U.S. Appl. No. 61/987,993 entitled Dual Mode Mechanical Catheter Cutting System filed May 2, 2014.
U.S. Appl. No. 62/005,315 entitled Surgical Instrument for Removing an Implanted Object filed May 30, 2014.
U.S. Appl. No. 62/058,790 entitled Medical Device for Removing an Implanted Object filed Oct. 2, 2014.
U.S. Appl. No. 62/094,808 entitled Multiple Configuration Surgical Cutting Device filed Dec. 19, 2014.
U.S. Appl. No. 62/113,865 entitled Medical Device for Removing an Implanted Object filed Feb. 9, 2015.
U.S. Appl. No. 14/771,775, filed Aug. 31, 2015.
Decision to Grant for European Patent Application No. 07255018.9, dated Aug. 8, 2013, 2 pages.
Department of Health and Ageing in Australian Government, "Horizon Scanning Technology Prioritising: Laser Extraction Systems." 2010. 15 pages.
EP extended Search Report dated Oct. 21, 2009; Application No. 07255019.7, 8 pages.
European Search Report issued in EP Application No. 15757928.5, dated Sep. 14, 2017, 6 pages.
Extended European Search Report for European Application No. 07255018.9, dated Nov. 12, 2010, 7 pages.
Extended European Search Report issued in EP Application No. 14770860.6, dated Jan. 10, 2017, 14 pages.
Extended European Search Report issued in EP Application No. 15757744.6, dated Sep. 14, 2017, 5 pages.
Final Action for U.S. Appl. No. 11/615,005, dated Nov. 9, 2009, 10 pages.
Final Action for U.S. Appl. No. 11/615,005, dated Nov. 21, 2013, 20 pages.
Intent to Grant for European Patent Application No. 07255018.9, dated Nov. 29, 2012, 7 pages.
International Preliminary Report on Patentability issued in PCT/US2015/016899, dated Sep. 15, 2016, 7 pages.
International Preliminary Report on Patentability issued in PCT/US2015/018305, dated Sep. 15, 2016, 10 pages.
International Search Report and Written Opinion for International Patent Application No. PCT/US2013/059434, dated Dec. 13, 2013, 14 pages.
International Search Report and Written Opinion issued in PCT/US2014/021167 dated Jun. 26, 2014, 19 pages.
International Search Report and Written Opinion issued in PCT/US2014/026496 dated Jul. 30, 2014, 16 pages.
International Search Report and Written Opinion issued in PCT/US2015/016899, dated May 1, 2015, 14 pages.
International Search Report and Written Opinion issued in PCT/US2015/018305, dated May 28, 2015, 14 pages.
International Search Report and Written Opinion issued in PCT/US2015/058227, dated Feb. 3, 2016, 18 pages.
International Search Report and Written Opinion issued in PCT/US2016/049108, dated Dec. 5, 2016, 9 pages.
Notice of Allowance for European Patent Application No. 07255018.9, dated Jul. 26, 2012, 47 pages.
Notice of Allowance for Japan Patent Application No. 2007-333273, dated Jan. 16, 2014, 3 pages.
Official Action for European Patent Application No. 07255018.9, dated Jul. 19, 2011, 3 pages.
Official Action for U.S. Appl. No. 11/615,005, dated Apr. 16, 2009, 13 pages.
Official Action for U.S. Appl. No. 11/615,005, dated Feb. 11, 2011, 12 pages.
Official Action for U.S. Appl. No. 11/615,005, dated Jul. 21, 2010, 10 pages.
Official Action for U.S. Appl. No. 11/615,005, dated Mar. 14, 2013, 16 pages.
Official Action for U.S. Appl. No. 13/800,728, dated Jan. 16, 2014, 14 pages.
Official Action with English translation for Japan Patent Application No. 2007-333173, dated Apr. 30, 2013, 5 pages.
Official Action with English translation for Japan Patent Application No. 2007-333173, dated Aug. 13, 2012, 7 pages.
Official Action with English translation for Japan Patent Application No. 2007-333273, dated Jul. 30, 2012, 7 pages.
Official Action with English translation for Japan Patent Application No. 2007-333273, dated Jun. 6, 2013, 10 pages.
PCT Application No. PCT/US2015/016899 entitled Medical Device for Removing an Implanted Object filed Feb. 20, 2015.
PCT Application No. PCT/US2015/018305 entitled Multiple Configuration Surgical Cutting Device filed Mar. 2, 2015.
Supplemental European Search Report issued in EP Application 14770355 dated Sep. 15, 2016, 7 pages.
Supplemental Partial European Search Report issued in EP Application No. EP14770860 dated Sep. 15, 2016, 7 pages.
U.S. Appl. No. 13/800,651 entitled System and Method of Ablative Cutting and Pulsed Vacuum Aspiration, filed Mar. 13, 2013.
U.S. Appl. No. 13/800,675 entitled Laser Catheter With Helical Internal Lumen, filed Mar. 13, 2013.
U.S. Appl. No. 13/800,700 entitled Device and Method of Ablative Cutting With Helical Tip, filed Mar. 13, 2013.
U.S. Appl. No. 13/800,728 entitled Laser Ablation Catheter, filed Mar. 13, 2013.
U.S. Appl. No. 13/828,231 entitled Tissue Slitting Methods and Systems, filed Mar. 14, 2013.
U.S. Appl. No. 13/828,310 entitled Tissue Slitting Methods and Systems, filed Mar. 14, 2013.
U.S. Appl. No. 13/828,383 entitled Tissue Slitting Methods and Systems, filed Mar. 14, 2013.
U.S. Appl. No. 13/828,441 entitled Tissue Slitting Methods and Systems, filed Mar. 14, 2013.
U.S. Appl. No. 13/828,536 entitled Expandable Lead Jacket, filed Mar. 14, 2013.
U.S. Appl. No. 13/828,638 entitled Lead Removal Sleeve, filed Mar. 14, 2013.
U.S. Appl. No. 13/834,405 entitled Retractable Blade for Lead Removal Device, filed Mar. 15, 2013.
U.S. Appl. No. 14/577,976 entitled Surgical Instrument Including an Inwardly Deflecting Cutting Tip for Removing an Implanted Object filed Dec. 19, 2014.
U.S. Appl. No. 14/589,688 entitled Retractable Separating Systems and Methods filed Jan. 5, 2015.
U.S. Appl. No. 14/627,851 entitled Medical Device for Removing an Implanted Object filed Feb. 20, 2015.
U.S. Appl. No. 14/627,950 entitled Medical Device for Removing an Implanted Object filed Feb. 20, 2015.

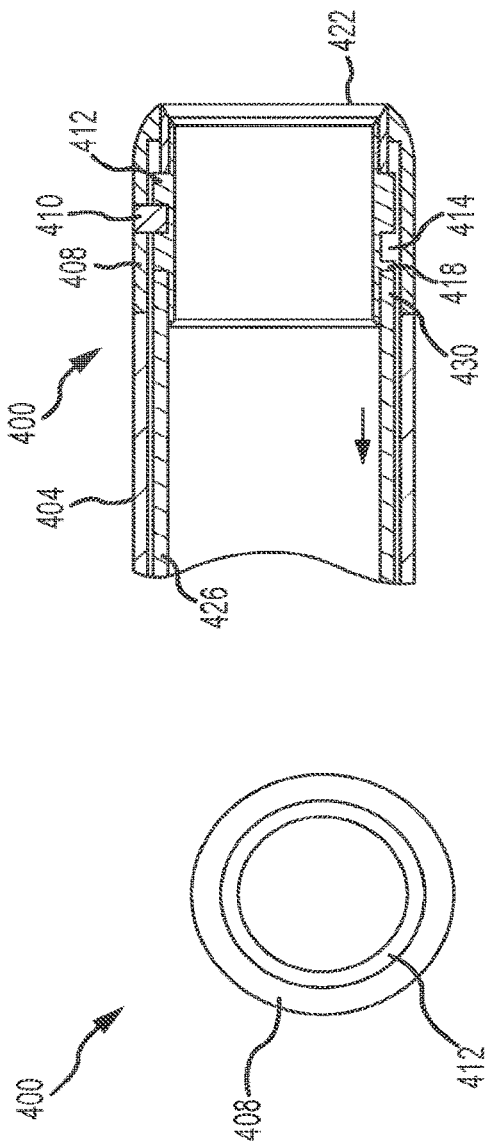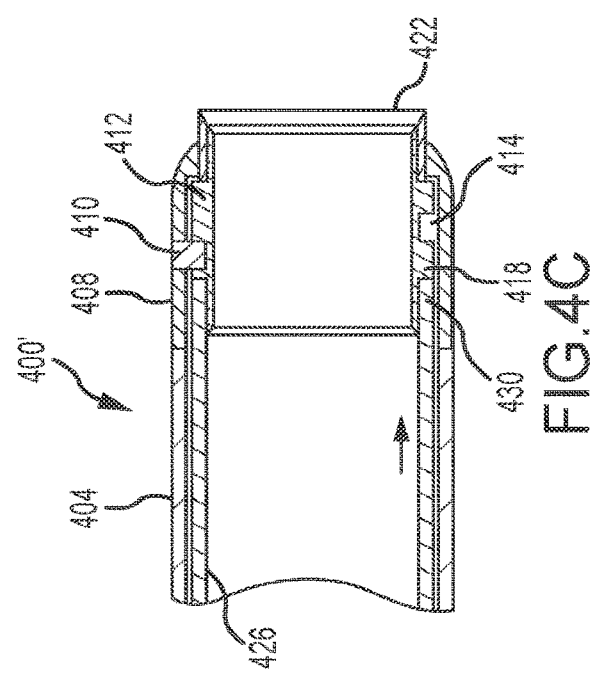
FIG. 4A
FIG. 4B
FIG. 4C

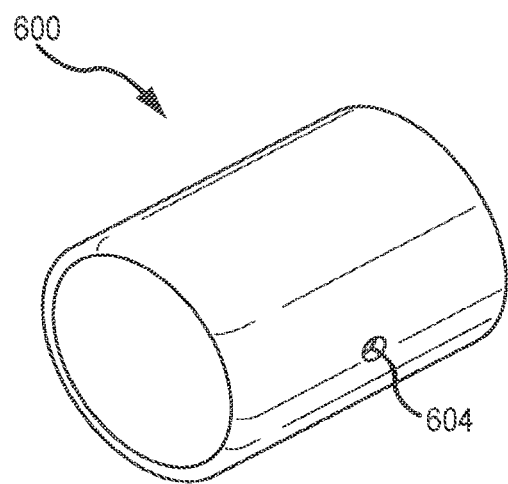
FIG.6A
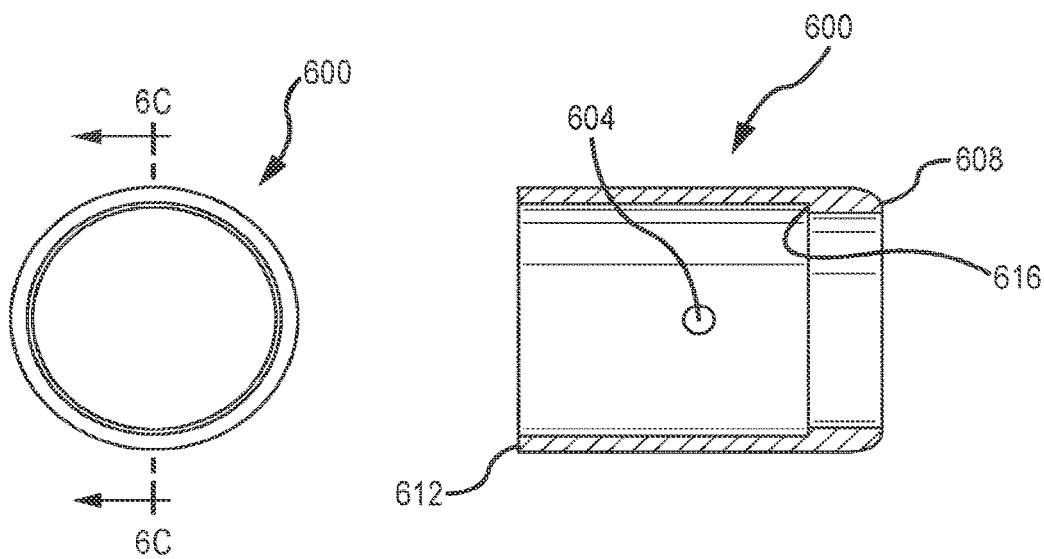
FIG.6B
FIG.6C

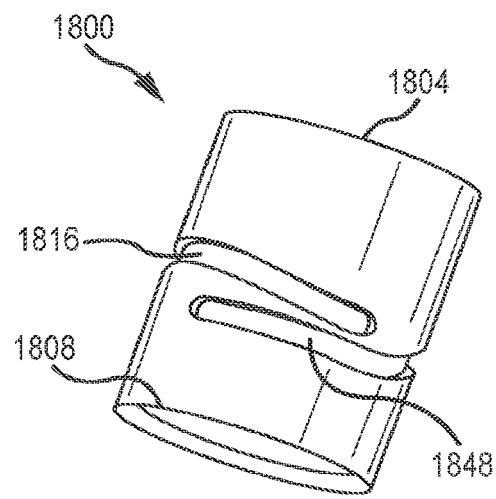
FIG.18
   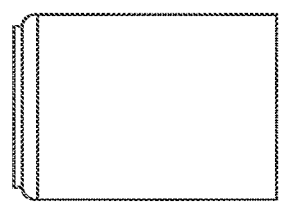   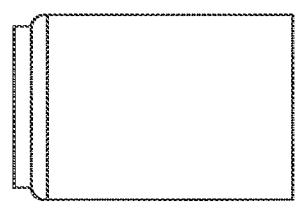
FIG.19A   FIG.19B   FIG.19C
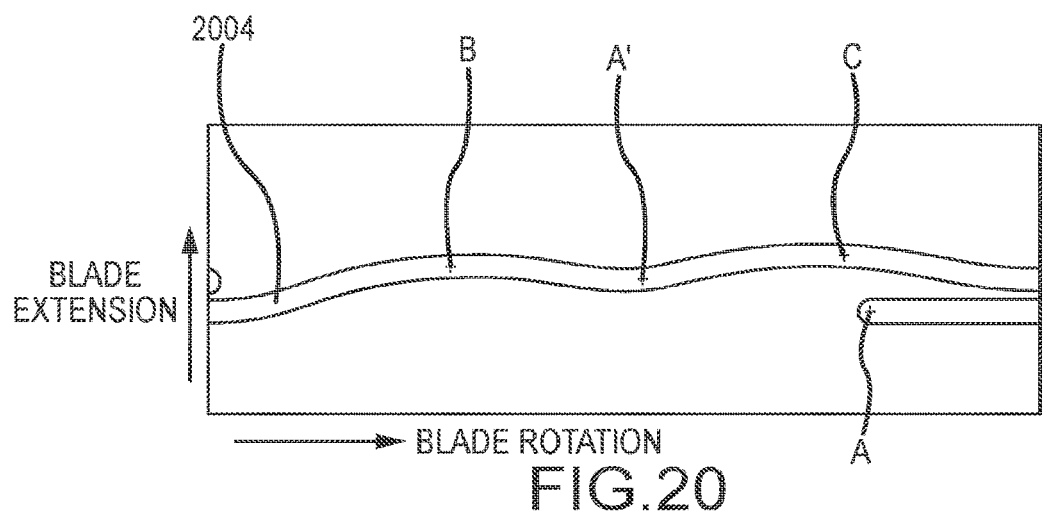
FIG.20

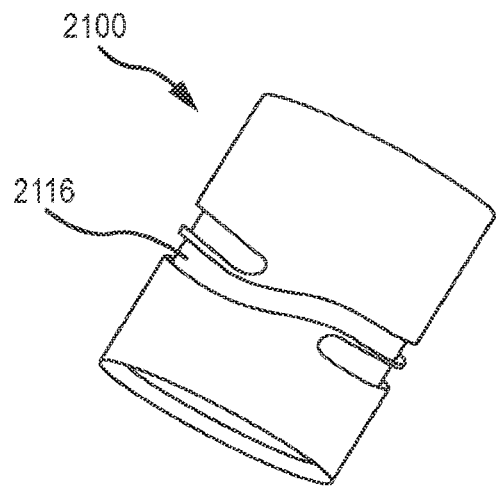
FIG.21
   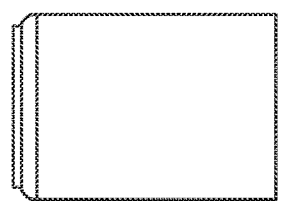   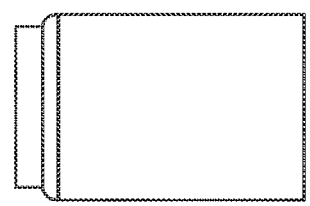
FIG.22A   FIG.22B   FIG.22C
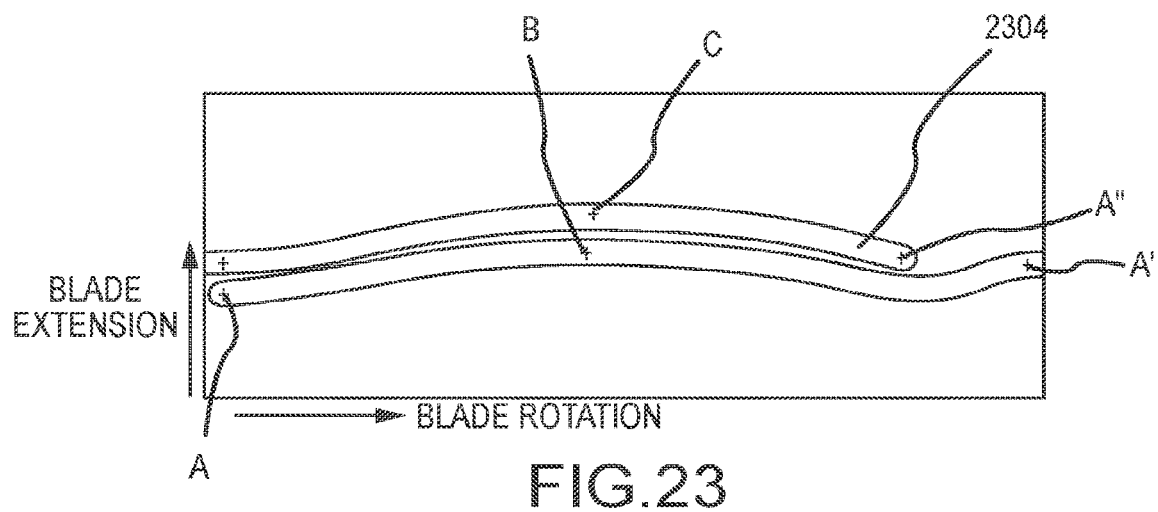
FIG.23

SURGICAL INSTRUMENT FOR REMOVING AN IMPLANTED OBJECT

CROSS REFERENCE TO RELATED APPLICATION

The present application is a continuation of U.S. application Ser. No. 15/890,151 filed Feb. 6, 2018, now U.S. Pat. No. 10,849,603, which is a continuation of U.S. application Ser. No. 14/771,775, filed Aug. 31, 2015 entitled "Surgical Instrument for Removing an Implanted Object", now U.S. Pat. No. 9,925,366, which is the United States National Phase of International Application No. PCT/US2014/026496 filed Mar. 13, 2014 and entitled "Surgical Instrument for Removing an Implanted Object", which claims the benefit of and priority, under 35 U.S.C. .sctn.119(e), to U.S. Provisional Application Ser. No. 61/793,597, filed Mar. 15, 2013, entitled "SURGICAL INSTRUMENT FOR REMOVING AN IMPLANTED OBJECT". Each of these applications is hereby incorporated herein by reference for all that it teaches and for all purposes.

FIELD OF THE DISCLOSURE

The present disclosure relates generally to devices, methods and systems for separating tissue in a patient, and more specifically, to devices for separating tissue attached to implanted objects, such as leads, in a patient and removing such objects.

BACKGROUND

Surgically implanted cardiac pacing systems, such as pacemakers and defibrillators, play an important role in the treatment of heart disease. In the 50 years since the first pacemaker was implanted, technology has improved dramatically, and these systems have saved or improved the quality of countless lives. Pacemakers treat slow heart rhythms by increasing the heart rate or by coordinating the heart's contraction for some heart failure patients. Implantable cardioverter-defibrillators stop dangerous rapid heart rhythms by delivering an electric shock.

Cardiac pacing systems typically include a timing device and a lead, which are placed inside the body of a patient. One part of the system is the pulse generator containing electric circuits and a battery, usually placed under the skin on the chest wall beneath the collarbone. To replace the battery, the pulse generator must be changed by a simple surgical procedure every 5 to 10 years. Another part of the system includes the wires, or leads, which run between the pulse generator and the heart. In a pacemaker, these leads allow the device to increase the heart rate by delivering small timed bursts of electric energy to make the heart beat faster. In a defibrillator, the lead has special coils to allow the device to deliver a high-energy shock and convert potentially dangerous rapid rhythms (ventricular tachycardia or fibrillation) back to a normal rhythm. Additionally, the leads may transmit information about the heart's electrical activity to the pacemaker.

For both of these functions, leads much be in contact with heart tissue. Most leads pass through a vein under the collarbone that connects to the right side of the heart (right atrium and right ventricle). In some cases, a lead is inserted through a vein and guided into a heart chamber where it is attached with the heart. In other instances, a lead is attached to the outside of the heart. To remain attached to the heart muscle, most leads have a fixation mechanism, such as a small screw and/or hooks at the end.

Within a relatively short time after a lead is implanted into the body, the body's natural healing process forms scar tissue along the lead and possibly at its tip, thereby fastening it even more securely in the patient's body. Leads usually last longer than device batteries, so leads are simply reconnected to each new pulse generator (battery) at the time of replacement. Although leads are designed to be implanted permanently in the body, occasionally these leads must be removed, or extracted. Leads may be removed from patients for numerous reasons, including but not limited to, infections, lead age, and lead malfunction.

Removal or extraction of the lead may be difficult. As mentioned above, the body's natural healing process forms scar tissue over and along the lead, and possibly at its tip, thereby encasing at least a portion of the lead and fastening it even more securely in the patient's body. In addition, the lead and/or tissue may become attached to the vasculature wall. Both results may, therefore, increase the difficulty of removing the leads from the patient's vasculature.

A variety of tools have been developed to make lead extraction safer and more successful. Current lead extraction techniques include mechanical traction, mechanical devices, and laser devices. Mechanical traction may be accomplished by inserting a locking stylet into the hollow portion of the lead and then pulling the lead to remove it. An example of such a lead locking device is described and illustrated in U.S. Pat. No. 6,167,315 to Coe el al., which is hereby incorporated herein by reference in its entirety for all that it teaches and for all purposes.

A mechanical device to extract leads includes a flexible tube called a sheath that passes over the lead and/or the surrounding tissue. The sheath typically may include a cutting blade, such that upon advancement, the cutting blade and sheath cooperate to separate the scar tissue from other scar tissue including the scar tissue surrounding the lead. In some cases, the cutting blade and sheath may also separate the tissue itself from the lead. Once the lead is separated from the surrounding tissue and/or the surrounding tissue is separated from the remaining scar tissue, the lead may be inserted into a hollow lumen of the sheath for removal and/or be removed from the patient's vasculature using some other mechanical devices, such as the mechanical traction device previously described in U.S. Pat. Publication No. 2008/0154293 to Taylor, which is hereby incorporated herein by reference in its entirety for all that it teaches and for all purposes.

Some lead extraction devices include mechanical sheaths that have trigger mechanisms for extending the blade from the distal end of the sheath. An example of such devices and method used to extract leads is described and illustrated in U.S. Pat. No. 5,651,781 to Grace, which is hereby incorporated herein by reference in its entirety for all that it teaches and for all purposes.

Controlling the extension of the blade with a patient's vasculature may be critical, particularly when the sheath and blade negotiate tortuous paths that exist in certain vascular or physiological environments. Furthermore, in certain cases, using such mechanical devices for lead removal may require more precise control, such as when the leads are located in, and/or attached to a structurally-weak portion of the vasculature. For instance, typical leads in a human may pass through the innominate vein, past the superior vena cava ("SVC"), and into the right atrium of the heart. Tissue growth occurring along the SVC and other locations along the innominate vein may increase the risk and difficulty in extracting the leads from such locations, particularly when the vein(s)' walls are thin. Tissue growth may also occur at other challenging locations within a patient's vasculature which requires the delicate and precise control of the devices used to extract leads from such locations.

SUMMARY

Accordingly, there is a need for a device, method and/or system such as a surgical device that has the capability to protect the vasculature from inadvertent contact from a blade during extension and rotation of the blade from a sheath. The present disclosure discusses a mechanism for protecting the vasculature from such inadvertent contact. The mechanism includes an outer sheath having a non-uniform wall thickness such that the distance between the blade and the exterior of the outer sheath is greater at one or more portions along the circumference and/or cross section of the outer sheath in comparison to the other portion(s) of the circumference and or cross section. Increasing the cross-sectional wall thickness for one or more portions of the outer sheath, particularly at the distal tip of the outer sheath, assists in shielding the vasculature from the blade during extension because the increased wall thickness creates a greater distance between the vasculature and the blade in comparison to the remainder of the outer sheath's cross section.

A device in accordance with this disclosure for removing an implanted object from a body vessel, may include a handle, an elongated sheath extending from the handle, the elongated sheath comprising having a proximal end, a distal end, and a lumen extending from the distal end toward the proximal end, wherein the lumen is configured to receive an implanted object, the elongated sheath further comprising a proximal portion and a distal portion, a tubular outer member attached to the distal portion of the elongated sheath, wherein at least one portion of the tubular outer member has a non-uniform circumferential wall thickness, a pin attached to the tubular outer member and extending inwardly thereof, and a tubular inner member located within the outer member, the tubular inner member comprising a proximal end, a distal end and an exterior surface therebetween, the distal end comprising a cutting surface, the exterior surface of the inner member comprising a cam slot for receipt of and cooperation with the pin such that upon actuation of the handle, the inner member rotates and the distal end of the inner member extends beyond the distal end of the elongated sheath.

The device may also include a non-uniform circumferential wall thickness having a first segment and a second segment, wherein the first segment has a thickness greater than the second segment. The configuration of the device may be such that the first segment is disposed adjacent or opposite the second segment along a cross section of a circumference of the tubular outer member. The device may alternatively or additionally be configured such that the first segment transitions to the second segment without interruption along the outer surface of the exterior sheath, thereby creating a smooth and unpronounced transition between a thicker wall portion and thinner wall portion.

The increased wall thickness of the outer sheath between the blade and the exterior of the outer sheath may be particularly helpful to clinicians when navigating the device through curved regions of the vasculature. For example, the clinician may wish to rotate the outer sheath to a position so that the increased wall thickness is adjacent the exterior of a curved vasculature, thereby creating a greater distance between the blade and the vasculature. It may, therefore, be helpful for the clinician to know, by looking at the exterior of the device and/or an imaging device, where the rotational position of the outer sheath comprising the increased cross-sectional wall thickness is located. Accordingly, the device may include an external indicator on the sheath or the handle and/or radiopaque marker on the sheath to indicate to the clinician the position of the portion(s) of the outer sheath that has the increased wall thickness. Accordingly, the present disclosure also discusses incorporating a second hollow inner member within the inner sheath, particularly the distal end of the inner sheath, including the inner cam member and the outer cam member.

There is also a need for a device, method and/or system such as a surgical device that has the capability to protect the lead as it enters into lumen of the sheath while the sheath passes over the lead and/or the surrounding tissue. Accordingly, another device in accordance with this disclosure for removing an implanted object from a body vessel may include a handle, an elongated sheath extending from the handle, the elongated sheath comprising a proximal end, a distal end, and a lumen extending from the distal end toward the proximal end, wherein the lumen is configured to receive an implanted object, the elongated sheath further comprising a proximal portion and a distal portion, a tubular outer member attached to the distal portion of the elongated sheath, a pin attached to the tubular outer member and extending inwardly thereof, a first tubular inner member located within the outer member, the first tubular inner member comprising a proximal end, a distal end and an exterior surface therebetween, the distal end comprising a cutting surface, the exterior surface of the first inner member comprising a cam slot for receipt of and cooperation with the pin such that upon actuation of the handle, the first inner member rotates and the distal end of the first inner member extends beyond the distal end of the elongated sheath, and a second tubular inner member, wherein at least one portion of the second tubular inner member has a non-uniform circumferential wall thickness.

The device may also include the second tubular inner member's non-uniform circumferential wall thickness having a first segment and a second segment, wherein the first segment has a thickness greater than the second segment.

The outer member, first inner member and a second inner member are described as tubular. The cross section of the exterior of outer member, first inner member and second inner member may have a variety of different shapes, such as circular, oval, elliptical, crescent, etc. depending upon whether the thickness of the wall for these members is uniform or non-uniform, as well as how the non-uniform shape is created. Similarly, the cross section of the lumen of first inner member and second inner member may have a variety of different shapes. And the cross section of the wall of the outer member, first inner member and second inner member may have a variety of different shapes.

There is a further need for a device, method and/or system such as a surgical device that has the capability to smoothly control the extension and rotation of a blade from a sheath. Accordingly, the present disclosure also discusses the incorporation of the linear slide that smoothly converts linear actuation of the trigger to rotational movement and extension of the cutting blade. A further device for removing an implanted object from a body vessel may comprise a handle comprising a trigger, an elongated sheath extending from the handle, the elongated sheath comprising a proximal end, a distal end, and a lumen extending from the distal end toward the proximal end, wherein the lumen is configured to receive an implanted object, the elongated sheath further comprising a proximal portion and a distal portion, a tubular outer member attached to the distal portion of the elongated sheath, a pin attached to the tubular outer member and extending inwardly thereof, a tubular inner member located within the outer member, the tubular inner member comprising a proximal end, a distal end and an exterior surface therebetween, the distal end comprising a cutting surface, the exterior surface of the inner member comprising a cam slot for receipt of and cooperation with the pin such that upon actuation of the handle, the inner member rotates and the distal end of the inner member extends beyond the distal end of the elongated sheath, and a rotary actuator disposed within the housing, the rotary actuator comprising a linear slide coupled to the trigger, the linear slide comprising a shaft, wherein the shaft is coupled to the tubular inner member, such that upon linear actuation of the trigger, the tubular inner member rotates.

The linear slide may also comprise a nut and leadscrew assembly, wherein the leadscrew comprises the shaft. Also, the shaft may comprise an exterior surface, wherein at least a portion of the exterior surface is threaded, and wherein the nut comprises a threaded portion and the threaded portion of the exterior of the shaft matingly engages with the threaded portion of the nut. Alternatively, the linear slide may comprise a rolling ring bearing and an unthreaded shaft.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X.sub.1-X.sub.n, Y.sub.1-Y.sub.m, and Z.sub.1-Z.sub.o, the phrase is intended to refer to a single element selected from X, Y, and Z, and a combination of elements selected from the same class (e.g., X.sub.1 and X.sub.2) as well as a combination of elements selected from two or more classes (e.g., Y.sub.1 and Z.sub.o).

The term "a" or "and" entity refers to one or more of that entity. As such, the terms "a" (or "an"), "one or more" and "at least one" may be used interchangeably herein. It is also to be noted that the terms "comprising", "including", and "having" may be used interchangeably.

A "lead" is a conductive structure, typically an electrically insulated coiled wire. The electrically conductive material may be any conductive material, with metals and intermetallic alloys common. The outer sheath of insulated material is biocompatible and bio stable (e.g., non-dissolving in the body) and generally includes organic materials such as polyurethane and polyimide. Lead types include, by way of non-limiting example, epicardial and endocardial leads. Leads are commonly implanted into a body percutaneously or and endocardial leads. Leads are commonly implanted into a body percutaneously or surgically.

The term "means" as used herein shall be given its broadest possible interpretation in accordance with 35 U.S.C. Section 112(f). Accordingly, a claim incorporating the terms "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

A "serration" or "serrated edge" or "serrated blade" or other variations, as used herein, shall mean the configuration of a cutting surface having a notched edge or saw-like teeth. The notched edges create a plurality of smaller points that contact (and therefore less contact area with) the material being cut in comparison to an un-notched blade. Additionally, the pressure applied by each serrated point of contact is relatively greater and the points of contact are at a sharper angle to the material being cut. One example of a serrated blade may include one notch adjacent to and abutting another notch such that there is very little, if any, blade between such notches, thereby creating points of contact. There are multiple variations and/or features of serrations. For example, one type of serrated feature is referred to as a "crown." As used herein, a serrated blade, or other variation, in the shape of a "crown," shall mean a blade comprising a plurality of notches and adjacent un-notched areas such that the combination of notched and un-notched areas resembles a crown for a royal member (e.g., king, queen, etc.), particularly when the blade is circular. A further type of "crown" includes a "hook crown." As used herein, a serrated blade, or other variation, in the shape of a "hook crown," shall mean a blade comprising a plurality of notches and adjacent un-notched areas, wherein the length of un-notched areas of the blade are longer than the notched areas of the blade.

A "surgical implant" is a medical device manufactured to replace a missing biological structure, support, stimulate, or treat a damaged biological structure, or enhance, stimulate, or treat an existing biological structure. Medical implants are man made devices, in contrast to a transplant, which is a transplanted biomedical tissue. In some cases implants contain electronics, including, without limitation, artificial pacemaker, defibrillator, electrodes, and cochlear implants. Some implants are bioactive, including, without limitation, subcutaneous drug delivery devices in the form of implantable pills or drug-eluting stents.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one ore more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 4A is an end view of the distal portion of the cutting sheath assembly according to an embodiment of the disclosure;

FIG. 4B is a cross-sectional view of the distal portion of the cutting sheath assembly according to an embodiment of the disclosure, wherein an inner member is in a retracted position within the cutting sheath assembly;

FIG. 4C is a cross-sectional view of the distal portion of the cutting sheath assembly according to an embodiment of the disclosure, wherein an inner member is in an extended position within the cutting sheath assembly;

FIG. 6A is perspective view of an outer band member according to an embodiment of the disclosure;

FIG. 6B is an end view of the outer band member illustrated in FIG. 6A;

FIG. 6C is cross-sectional view of the outer band member illustrated in FIG. 6A taken along line 6C-6C of FIG. 6B;

FIG. 18 is a perspective view of an inner member having a cam slot with an extended stow region;

FIG. 19A is a side view of the outer member with the inner member of FIG. 18 positioned in a retracted position within the outer sheath;

FIG. 19B is a side view of the outer member with the inner member of FIG. 18 positioned in a partially extended portion within the outer sheath;

FIG. 19C is a side view of the outer member with the inner member of FIG. 18 positioned in a fully extended position within the outer sheath;

FIG. 20 is an illustration of the geometry of the cam slot of the inner member illustrated in FIG. 18 portrayed on a single plane;

FIG. 21 is a perspective view of an inner member having a duplex cam slot;

FIG. 22A is a side view of the outer member with the inner member of FIG. 21 positioned in a retracted position within the outer sheath;

FIG. 22B is a side view of the outer member with the inner member of FIG. 21 positioned in a partially extended position within the outer sheath.

FIG. 22C is a side view of the outer member with the inner member of FIG. 21 positioned in a fully extended position within the outer sheath;

FIG. 23 is an illustration of the geometry of the cam slot of the inner member illustrated in FIG. 21 portrayed on a single plane;

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
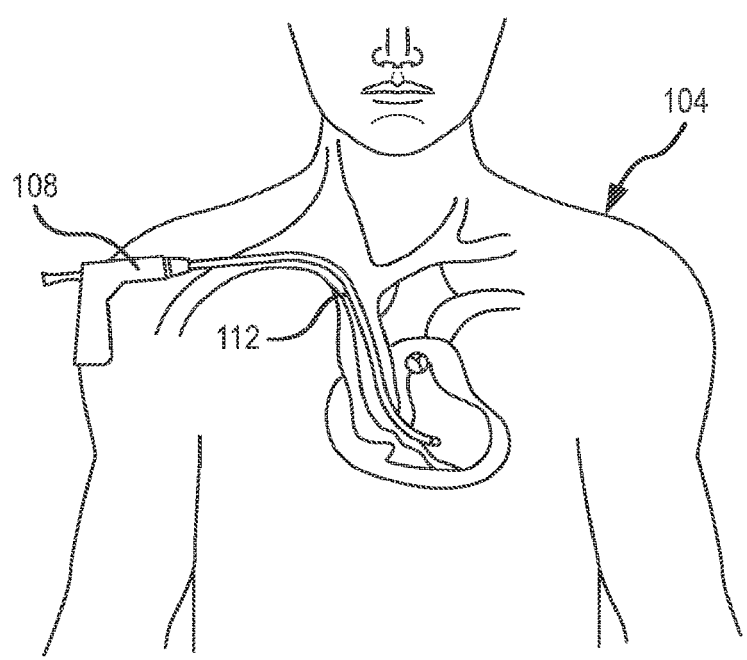
FIG. 1 is a perspective view of a human having a pacemaker lead located in the venous system and terminating electrode anchored to the ventricular heart chamber, with an embodiment of a surgical device being shown inserted into the body and partly advanced over the lead.

Embodiments according to this disclosure provide a surgical device that includes a sheath, which can be deployed safely within a vascular system of a patient and separate implanted objects, such as leads, from a patient's vasculature system. FIG. 1 depicts a surgical device 108 having a sheath 112 inserted within an exemplary patient 104. The sheath 112 surrounds an implanted lead (not shown) running along the left innominate vein past the SVC and connected into, or about, the right ventricle of the heart. Upon surrounding the lead with the sheath, the user of the surgical devise may actuate the handle, thereby extending a cutting blade (not shown) beyond the distal end of the sheath 112 to cut the tissue surrounding the lead within the patient's SVC. When the clinician releases the handle, the cutting blade returns within the sheath 112, thereby allowing the clinician to force and advance the distal portion of the sheath against additional uncut tissue. The clinician repeats the actuation step, thereby causing the cutting blade to re-appear and extend beyond the distal end of the sheath 112 to cut the adjacent tissue. Each time actuation occurs, the proximal portion of the implanted lead and/or surrounding tissue enters into a hollow passageway within the sheath 112. This process is again repeated until the implanted lead and/or surrounding tissue is completely or substantially separated from the tissue attached to the SVC. At that time, the implanted lead may safely be removed from the patient's SVC.

Figure 2A:
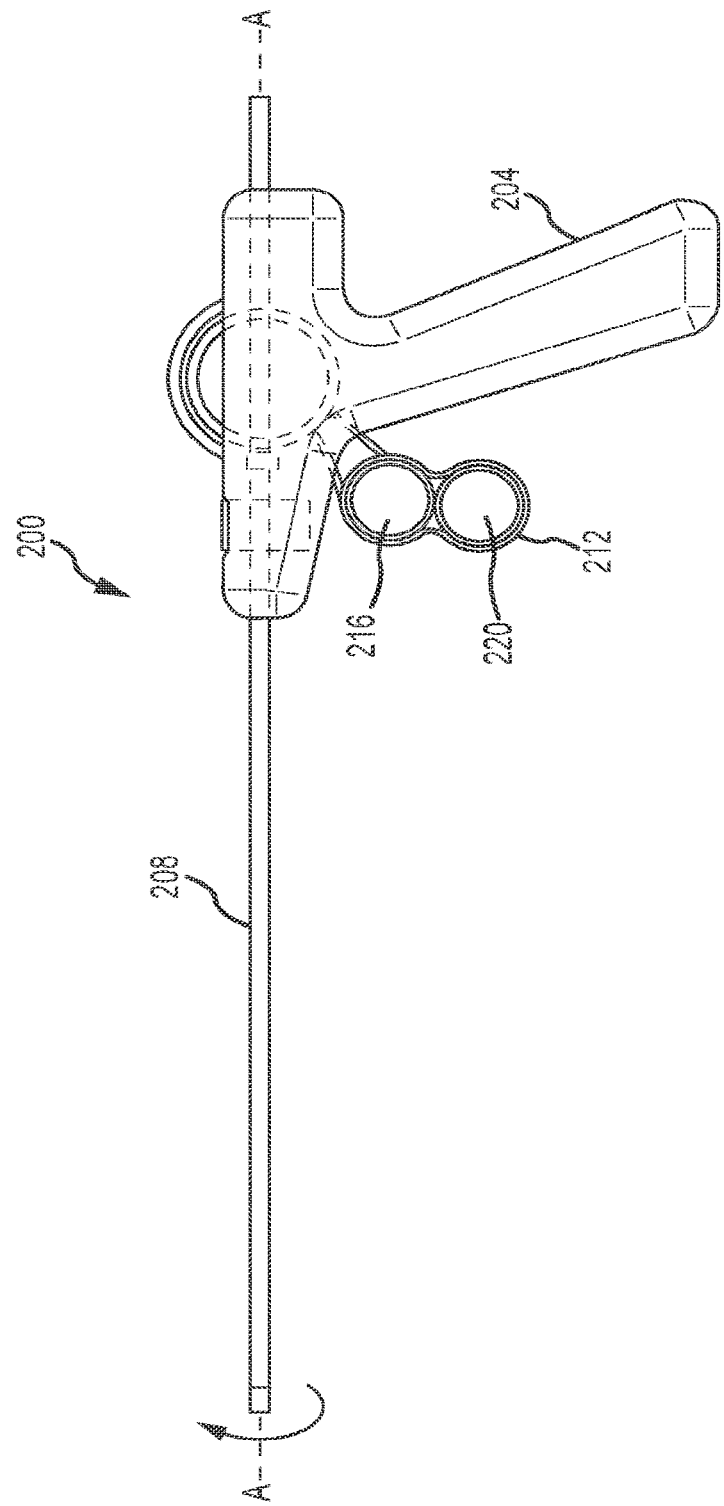
FIG. 2A is an elevation view of an embodiment of a surgical device.
Figure 2B:
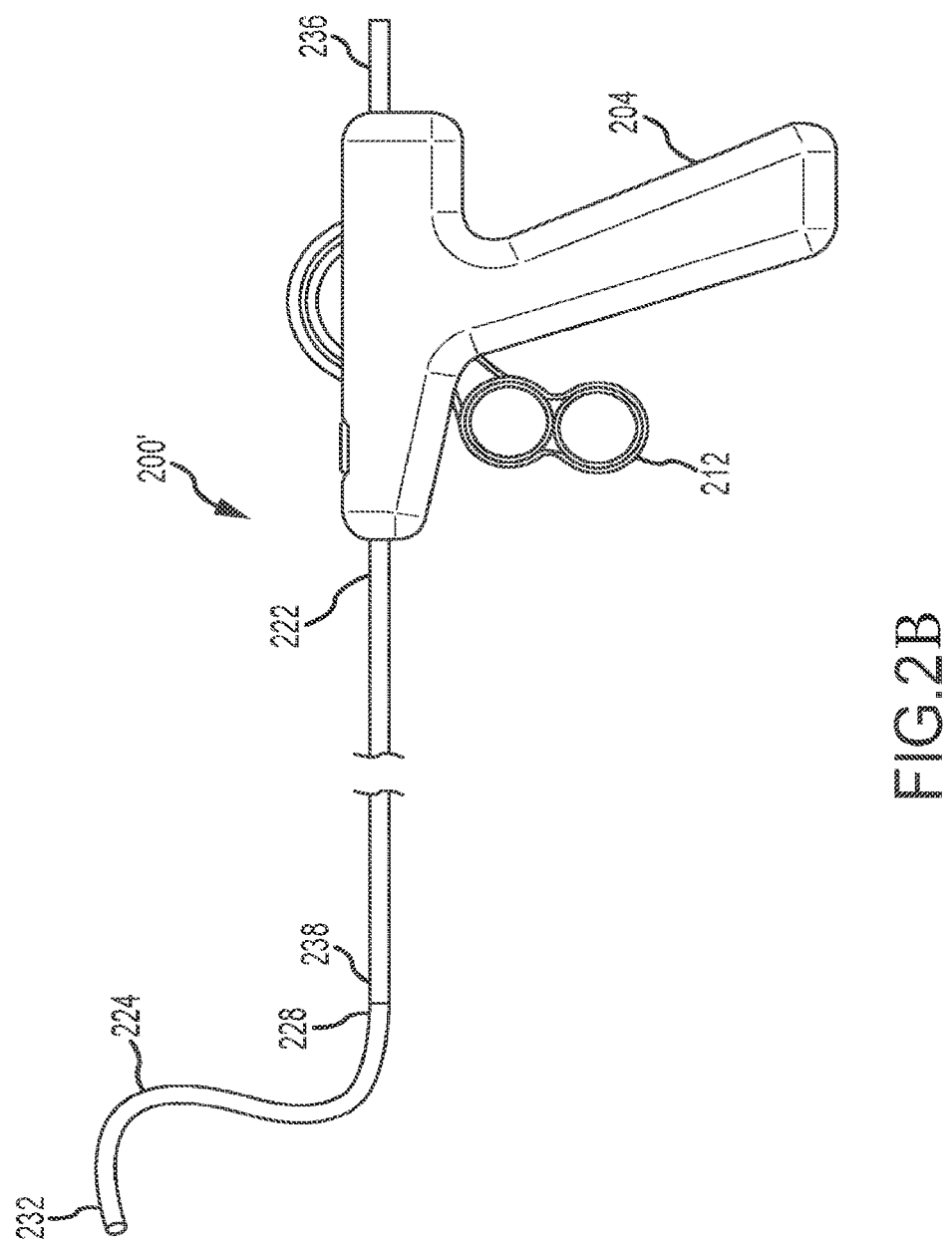
FIG. 2B is an elevation view of an alternative embodiment of a surgical device.

With reference to FIG. 2, an exemplary surgical device 200 is depicted. The surgical device 200 includes a handle 204 and an outer sheath 208. The surgical device also includes an inner sheath (not shown) located within the outer sheath 208. It may be preferable for the outer sheath 208 to remain stationary while the inner sheath is capable of moving (e.g., rotating and extending) with respect to the outer sheath 208. The inner sheath and outer sheath 208 can both be flexible, rigid or a combination thereof.

The handle 204 includes a trigger 212 which pivots about a pin (not shown) that attaches the trigger 212 to the handle 204. Attached to the portion of the trigger 212 within the handle 204 is a first gear (not shown). Also included within the handle 204 is second gear and a third gear (both of which are not shown). The first gear meshes with the second gear, which in turn meshes with the third gear. The third gear has an opening through its center, wherein the opening is sized and configured to allow the inner sheath to be inserted and affixed thereto. When a use (i.e., clinician) actuates the handle 204, it pivots about the pin, thereby causing the handle 204 and first gear to move in a counter clockwise direction. The first gear engages the second gear and causes the second gear to rotate. The second gear, in turn, engages the third gear initiating it and the inner sheath to rotate about the sheath's longitudinal axis A-A.

The handle may also include a spring (not shown) that is attached to the gears, sheath and/or some other member therein such that, upon the clinician's release of the handle, the spring facilitates rotation of the inner sheath in a direction opposite to that in which it rotated upon actuation of the handle 204. It may be preferable for the inner sheath to rotate in a clockwise direction about its longitudinal axis from the perspective of the proximal end of the surgical device 200. If so, the spring will facilitate the inner sheath rotation in a counter-clockwise direction upon the clinician's release of the trigger 212.

The trigger 212 and gears are one example of an actuation means for causing the inner sheath to rotate about its longitudinal axis. However, a variety of different triggers and gearing may cooperate to rotate the inner sheath. For example, the trigger 212 depicted in FIG. 1 includes two openings 216, 220. A trigger, however, may have less than or more than two openings. Additionally, a trigger may also be comprised of a straight or non-linear member without any openings. Furthermore, a trigger may be in the shape of a button capable of being depressed. As long as the trigger, either alone or in conjunction with the handle, is ergonomically correct and comfortable for the clinician, the trigger may have a variety of sizes and shapes.

The actuation means discussed above includes three gears. A lower or higher number of gears, however, may be used in lieu of three gears. Many different types of gears are available. Non-limiting examples of gears include, but are not limited to, spur gears, helical gears, double helical gears, bevel gears, spiral bevel gears, hypoid gears, crown gears, worm gears, non-circular gears, rack and pinion gears, epicyclic gears, sun and planet gears, harmonic drive gears, cage gears, and magnetic gears. Any one and/or combination of these types or other types of gears could be used.

The trigger 212 and gear(s) configuration discussed above is an example of a mechanical actuation means to rotate the inner sheath. In an alternate embodiment, the actuation means may comprise electromechanical components. For example, the actuation means may comprise an electric motor (not shown) having a driven shaft that is directly or indirectly coupled to the inner sheath. The motor's shaft may be indirectly coupled to the inner sheath by one or more gears discussed hereinbefore. The motor may be controlled by a switch, thereby causing the inner sheath to rotate in a clockwise and/or a counterclockwise direction upon actuating a switch that may also act as the trigger. The electric motor may be either a direct current (DC) motor or an alternating current (AC) motor. Accordingly, the motor may be powered by a DC source, such as a battery, or an AC source, such as a conventional power cord. Additionally, those skilled in the art will appreciate that there are numerous other ways in which a surgical device comprising a rotatable sheath may be actuated and driven.

It may be preferable for a portion of the outer sheath to be rigid and a portion of the outer sheath to be flexible. With reference to FIG. 2A, an exemplary surgical device 200' comprising an outer sheath having a rigid outer portion 222 and a flexible outer portion 224 is depicted. Both the rigid outer portion 222 and a flexible outer portion 224 are constructed of materials suitable for insertion into the human body. For example, the rigid outer portion 222 may be constructed of stainless steel, and the flexible outer portion 224 may be constructed of a flexible polymer such as polytetrafluoroethylene or thermoplastic elastomers.

The rigid outer portion 222 and flexible outer portion 224 form a unitary outer sheath. The rigid outer portion 222 has a proximal end 236 and a distal end 238. Similarly, the flexible outer portion 224 has a proximal end 228 and a distal end 232. The distal end 238 of the rigid outer portion 222 is connected to the proximal end 228 of the flexible outer portion 224, thereby forming a unitary outer sheath. The mechanism(s) to connect the distal end 238 of the rigid outer portion 222 and the proximal end 228 of the flexible outer portion 224 are not described herein and are conventional, and need not be further explained or illustrated to enable one skilled in the art to utilize the mechanism for the purposes described. For example, the configuration and/or shape of the proximal end 228 may be such that it may interlock with the distal end 238 for example via a barbed joint. Although the interlock mechanism described herein may be preferred, it is not intended to represent the only way that such a connection can be accomplished. All such techniques within the knowledge of one skilled in the art are considered within the scope of this disclosure.

Figure 39:
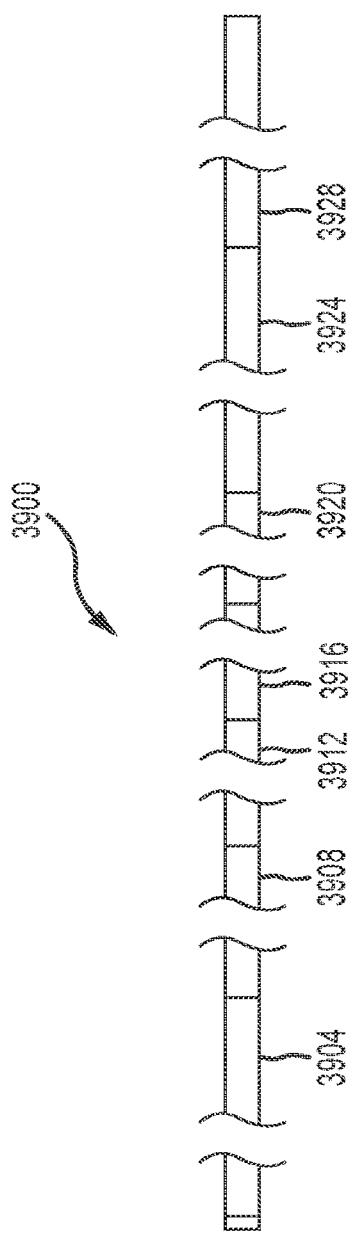
FIG. 39 is a side elevation view of an elongated shaft or sheath that is constructed by a series of interrupted cut hypotube segments.

Similar to the flexible outer sheath 224, the inner sheath is generally flexible in order to accept, accommodate and navigate the patient's vasculature system. In addition to being flexible, the inner and/or outer sheaths may also have a high degree of stiffness in order to receive the torque transferred from the actuation means and transfer sufficient torque to the cutting blades discussed in more detail below. The inner and/or outer sheaths may be formed of a polymer extrusion, braided reinforced polymer extrusion, coils, bi-coils, tri-coils, laser cut metal tubing and any combination of the above. Referring to FIG. 39, the inner and/or outer sheaths may be a unitary structure 3900, such as a hypotube, comprising multiple segments 3904, 3908, 3916, 3920, 3924, 3928. The hypotube may include segments having the same rigidity and/or flexibility, or the hypotube may include segments having a variety of different rigidity and flexibility characteristics to yield the overall desirable rigidity and flexibility for the hypotube. The segments may include radially patterned cuts that extend partially into and/or fully through the wall of the tube. The pattern of each and/or multiple segments may include altering the depth, width, pitch, circumferential length, etc. may to produce the desired flexibility and rigidity profile for the inner sheath (and/or outer sheath) when constructed from a hypotube. Additionally, if the inner and/or outer sheaths have multiple segments, those multiple segments may be attached in a manner similar to the manner in which the rigid outer sheath 222 and flexible outer sheath 224 are connected.

With reference to FIGS. 4A, 4B and 4C, an exemplary distal portion of the flexible inner and outer sheaths of a surgical device is depicted. The assembly 400 includes a flexible inner sheath 426 located within flexible outer sheath 404. Attached to the distal portion of the flexible outer sheath 404 is an outer cam member 408, which is discussed in more detail below. The distal end of the flexible outer sheath 404 is generally smooth and evenly rounded at its most distal point, thereby allowing it to act as a dilator when pressed and forced against tissue. And the distal end of the outer cam member 408 is also longitudinally aligned with the distal end of the flexible outer sheath 404. The distal end 430 of the flexible inner sheath 426 is connected to the proximal end 418 of inner cam member 412, which is discussed in more detail below. The distal end 422 of inner cam member 412 includes a cutting surface capable of cutting tissue.

The inner sheath 426 is coupled to the outer sheath 404 through the inner cam member 412 and the outer cam member 408 via pin 410. One end of the pin 410 is fixed within the outer cam member 412, and the other end of the pin 410 is located within the cam slot 414 of the inner cam member 412. As the inner sheath 426 extends, via the actuation means discussed above, the inner cam member 412 extends distally in the direction of the arrow (.fwdarw.) and rotates according to the profile of the cam slot 414. As the inner cam member 412 extends distally and rotates, the outer sheath 404, outer cam member 408 and pin 412 remain stationary. Thus, as the inner cam member 412 extends distally (and potentially proximally according to the cam slot profile) and rotates the cutting surface at the distal end 422 of the inner cam member 412 is able to perform a slicing action against the tissue and cut it.

FIG. 4B depicts the inner cam member 412 within a retracted (an un-actuated) position because the inner cam member 412 is in its most proximal position. Stated differently, the distal end 422 of the inner cam member 412 of FIG. 4B is located within the interior of the outer cam member 408 and does not extend beyond the distal end of the outer cam member 408. With reference to FIG. 4C, the inner cam member 412 is depicted in an extended (and actuated) position because the inner cam member 412 is in its most distal position extending beyond the distal end of the flexible outer sheath 404 and the outer cam member 408.

Figure 3:
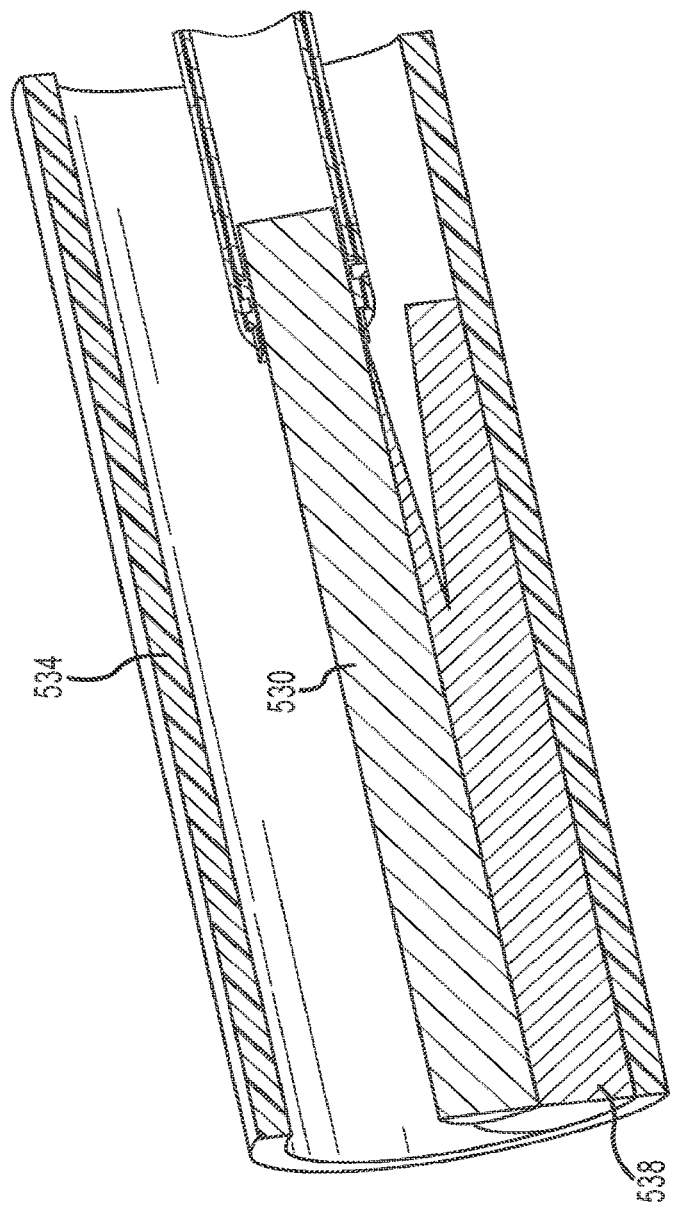
FIG. 3 is a cross-sectional view of a cutting sheath assembly within a blood vessel with an extendable and rotatable blade for removing a lead according to an embodiment of the disclosure.

FIG. 3 depicts the distal portion of the flexible outer sheath and flexible inner sheath of FIG. 4C surrounding a lead 530 within a patient's vein 534 with the inner cam member 412 in its extended position. The circumferential nature of the cutting blade at the distal end of the inner cam member causes the surgical device to act as a coring device, thereby cutting tissue 538 either partially (i.e., less than 360 degrees) or completely (i.e., 360 degrees) around the lead or implanted object being extracted. The amount of tissue that the blade cuts depends upon the size, shape and configuration of the lead, as well as the diameter and thickness of the circular cutting blade. For example, if the diameter of the circular blade is substantially greater than the diameter of the lead, then the blade will cut and core more tissue in comparison to a cutting blade having a smaller diameter. Once the desired cut has been made, the operator releases trigger and the inner cam member (including the blade) returns to its retracted position. Once the blade is in the retracted position, the distal tip 408 of the cam member 404 (and/or outer sheath) safely acts as a dilating device, thereby stretching tissue as the sheaths move over the lead or implanted object to be extracted.

Figure 5A:
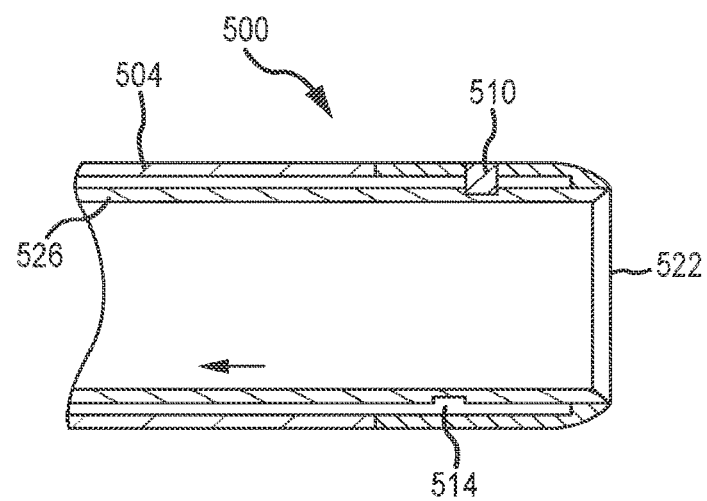
FIG. 5A is a cross-sectional view of the distal portion of the cutting sheath assembly according to an embodiment of the disclosure, wherein an inner sheath is in a retracted position.
Figure 5B:
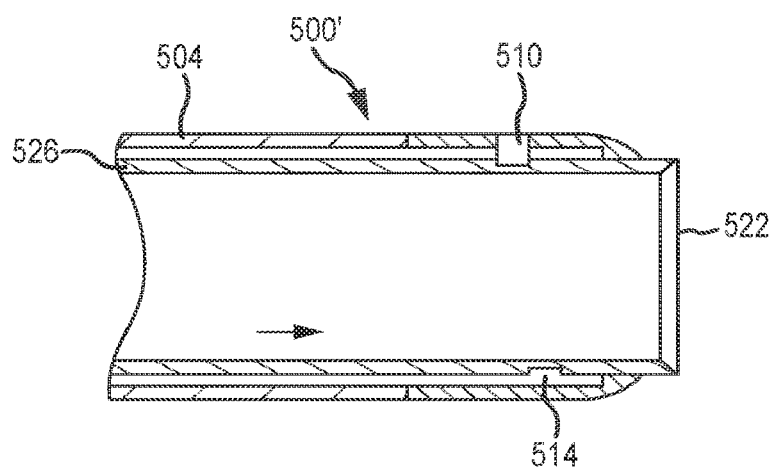
FIG. 5B is cross-sectional view of the distal portion of the cutting sheath assembly according to an alternate embodiment of the disclosure, wherein an inner sheath is in an extended position.
Figure 7A:
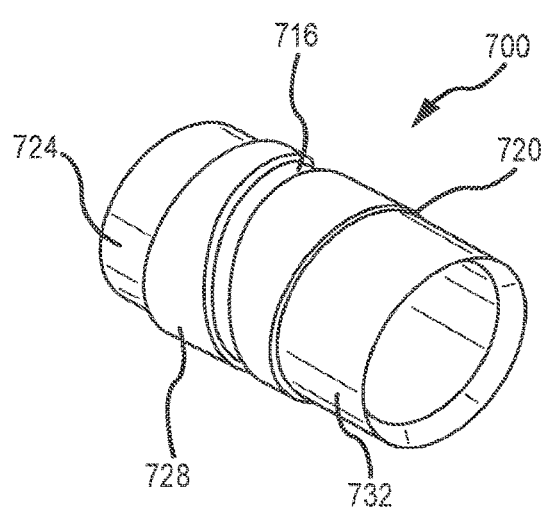
FIG. 7A is perspective view of an inner band member according to an embodiment of the disclosure.
Figure 7B:
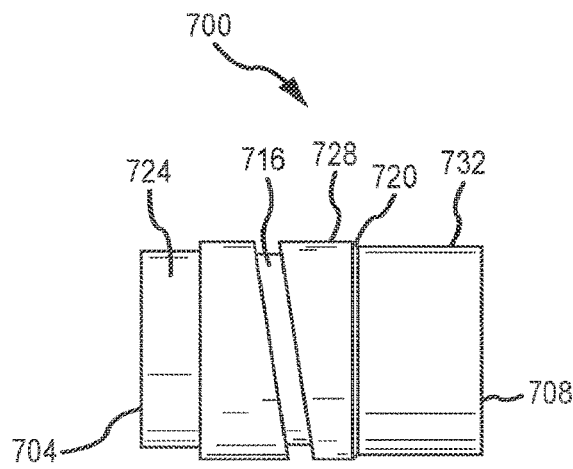
FIG. 7B is side view of the inner band member illustrated in FIG. 7A.
Figure 7C:
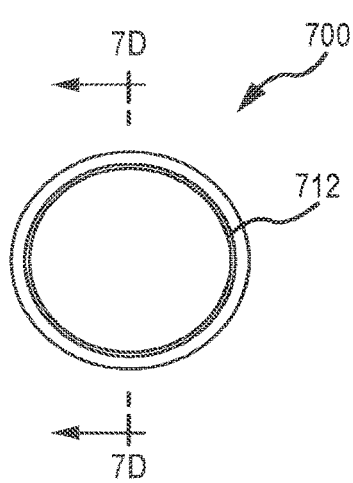
FIG. 7C is end view of the inner band member illustrated in FIG. 7A.
Figure 7D:
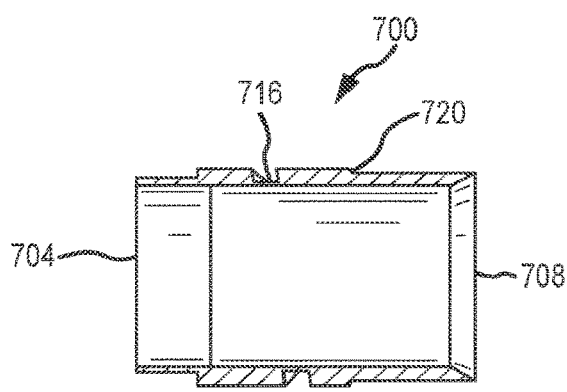
FIG. 7D is cross-sectional view of the inner band member illustrated in FIG. 7A taken along line 7D-7D in FIG. 7C.
Figure 8A:
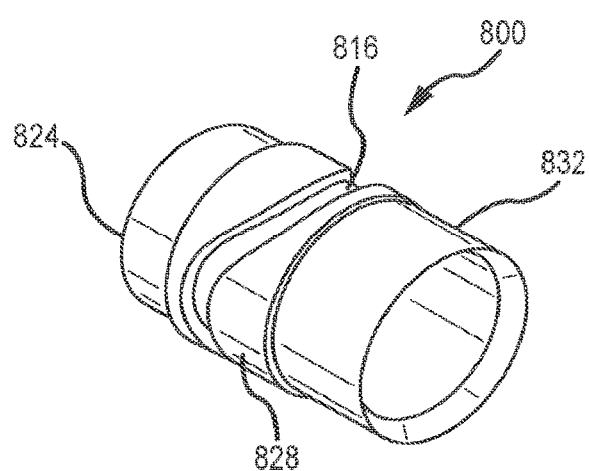
FIG. 8A is perspective view of an inner band member according to an embodiment of the disclosure.
Figure 8B:
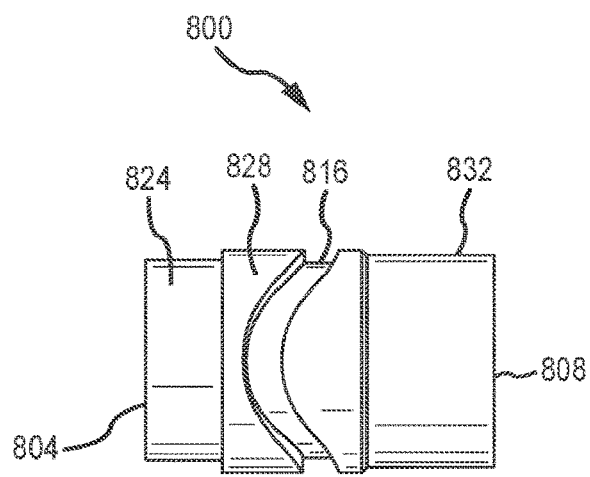
FIG. 8B is side view of the inner band member illustrated in FIG. 8A.
Figure 8C:
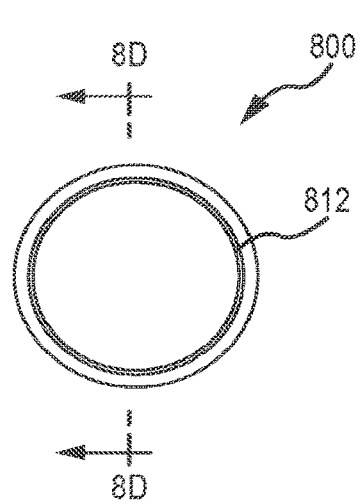
FIG. 8C is end view of the inner band member illustrated in FIG. 8A.
Figure 8D:
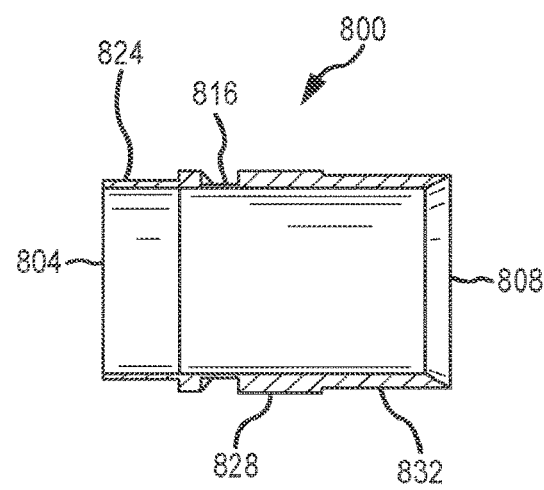
FIG. 8D is cross-sectional view of the inner band member illustrated in FIG. 8A taken along line 8D-8D in FIG. 8C.
Figure 9A:
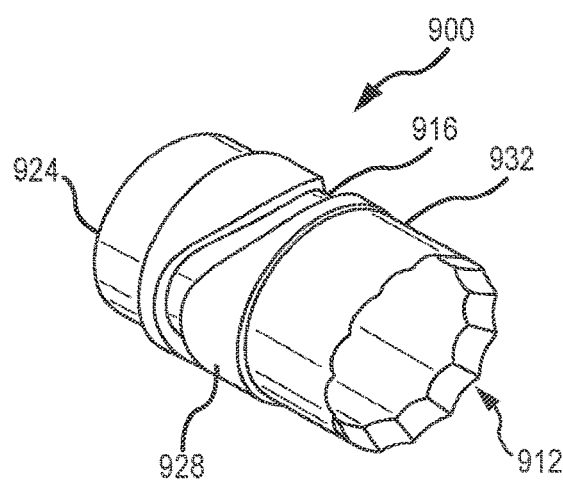
FIG. 9A is perspective view of an inner band member according to an embodiment of the disclosure.
Figure 9B:
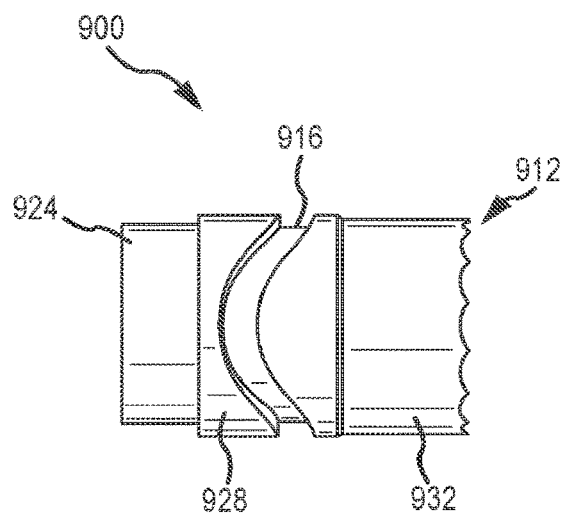
FIG. 9B is side view of the inner band member illustrated in FIG. 9A.
Figure 9C:
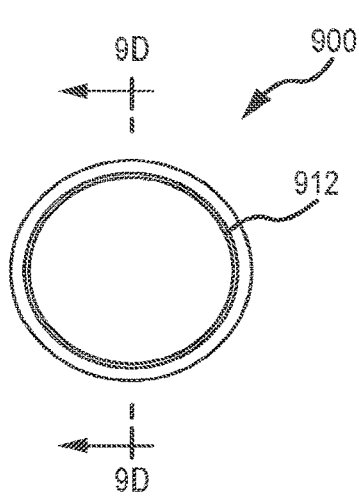
FIG. 9C is end view of the inner band member illustrated in FIG. 9A.
Figure 9D:
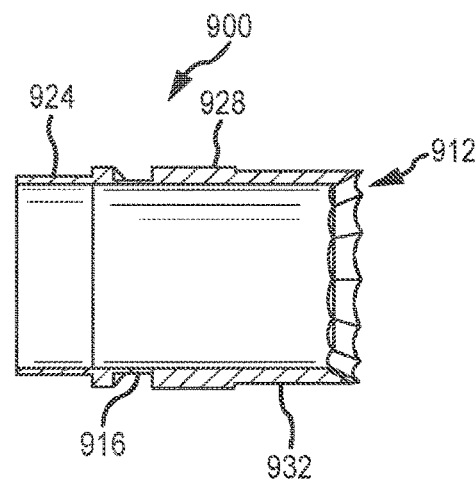
FIG. 9D is cross-sectional view of the inner band member illustrated in FIG. 9A taken along line 9D-9D in FIG. 9C.
Figure 10A:
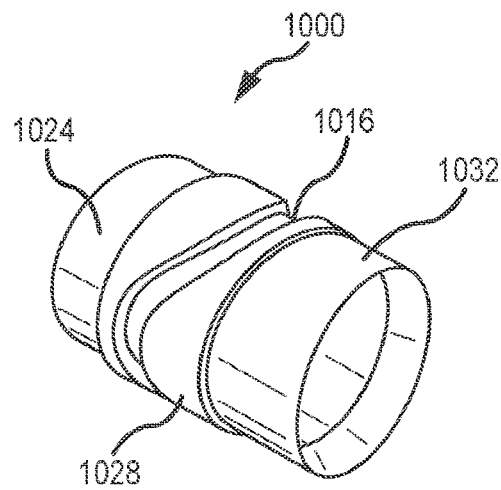
FIG. 10A is perspective view of an inner band member according to an embodiment of the disclosure.
Figure 10B:
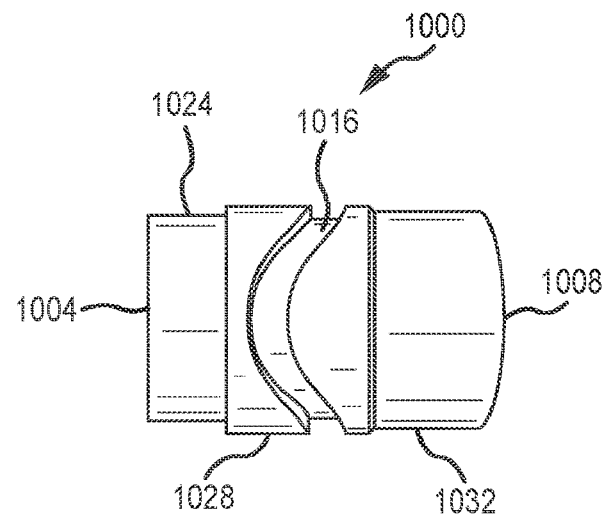
FIG. 10B is side view of the inner band member illustrated in FIG. 10A.
Figure 10C:
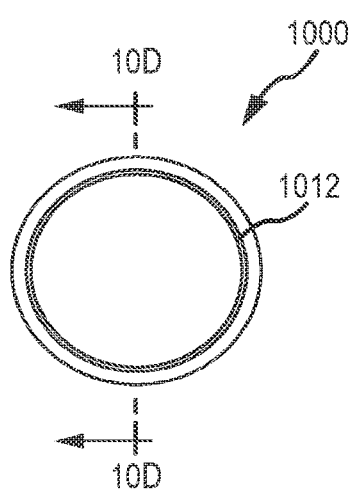
FIG. 10C is end view of the inner band member illustrated in FIG. 10A.
Figure 10D:
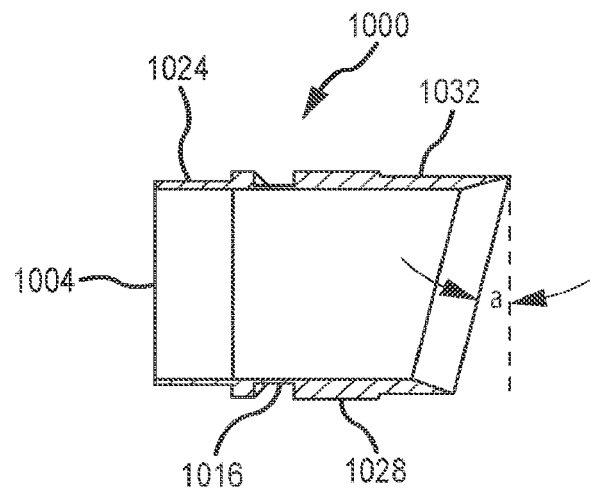
FIG. 10D is cross-sectional view of the inner band member illustrated in FIG. 10A taken along line 10D-10D in FIG. 10C.
Figure 11A:
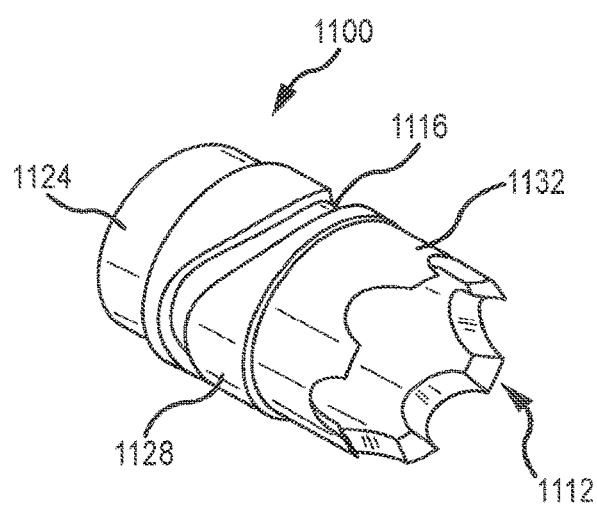
FIG. 11A is perspective view of an inner band member according to an embodiment of the disclosure.
Figure 11B:
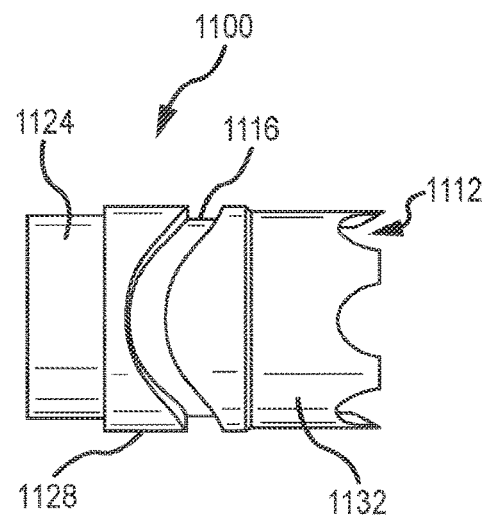
FIG. 11B is side view of the inner band member illustrated in FIG. 11A.
Figure 11C:
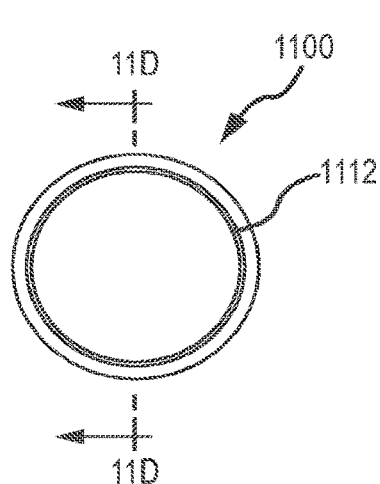
FIG. 11C is end view of the inner band member illustrated in FIG. 11A.
Figure 11D:
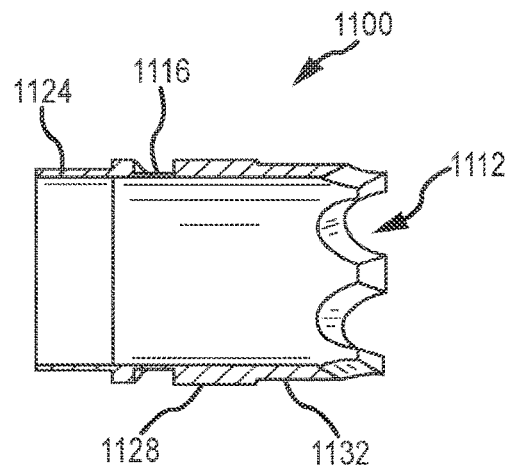
FIG. 11D is cross-sectional view of the inner band member illustrated in FIG. 11A taken along line 11D-11D in FIG. 11C.
Figure 12A:
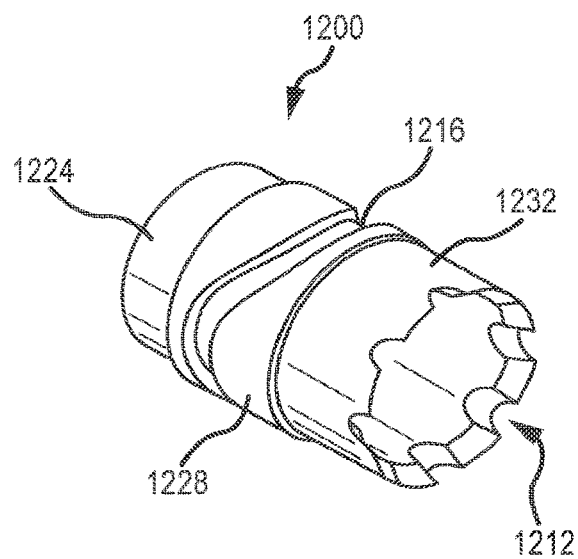
FIG. 12A is perspective view of an inner band member according to an embodiment of the disclosure.
Figure 12B:
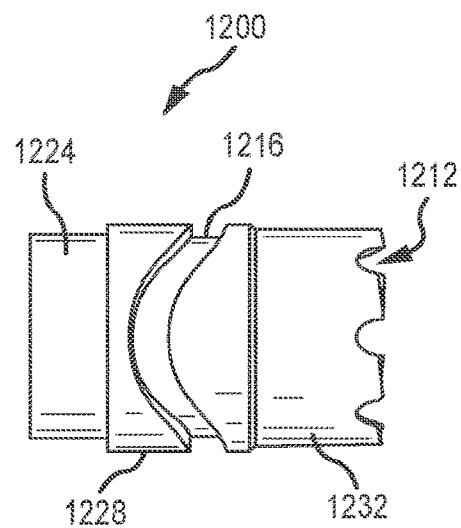
FIG. 12B is side view of the inner band member illustrated in FIG. 12A.
Figure 12C:
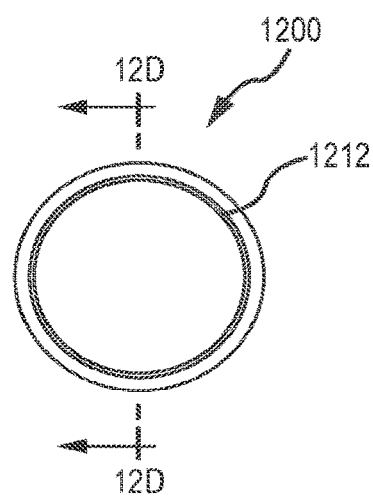
FIG. 12C is end view of the inner band member illustrated in FIG. 12A.
Figure 12D:
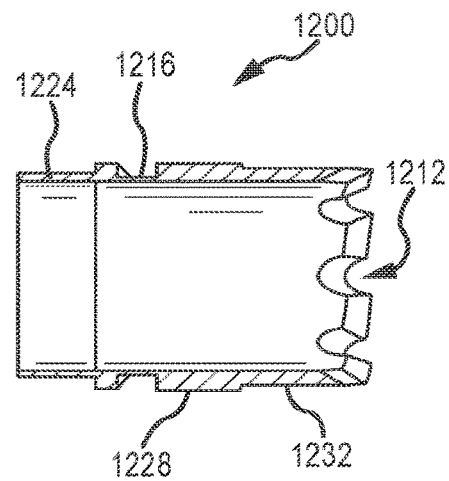
FIG. 12D is cross-sectional view of the inner band member illustrated in FIG. 12A taken along line 12D-12D in FIG. 12C.
Figure 13A:
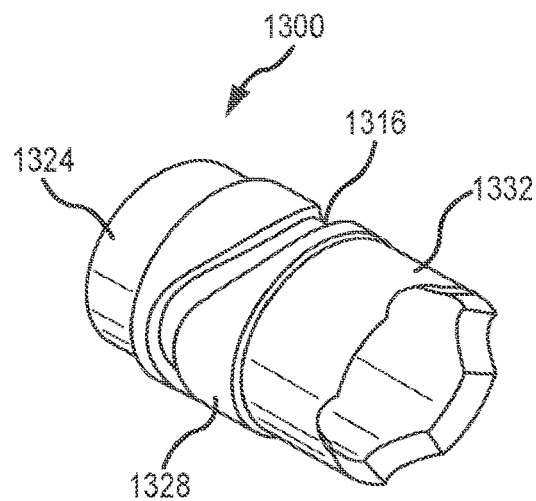
FIG. 13A is perspective view of an inner band member according to an embodiment of the disclosure.
Figure 13B:
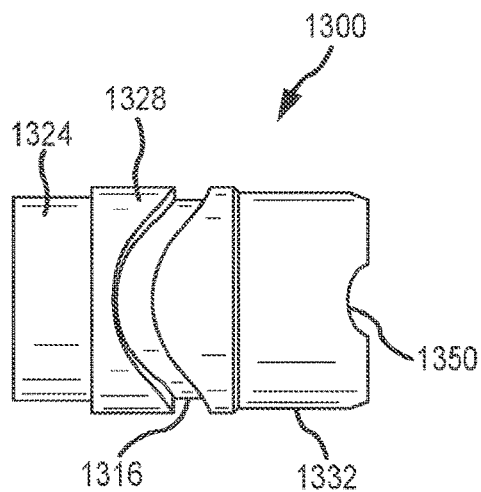
FIG. 13B is side view of the inner band member illustrated in FIG. 13A.
Figure 13C:
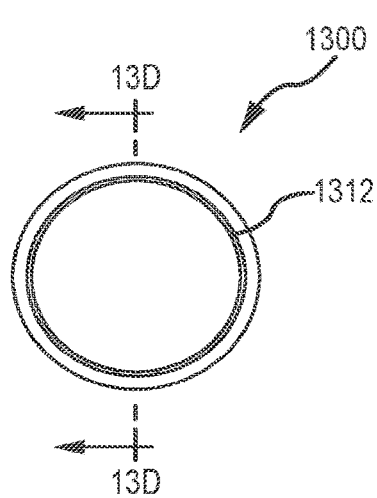
FIG. 13C is end view of the inner band member illustrated in FIG. 13A.
Figure 13D:
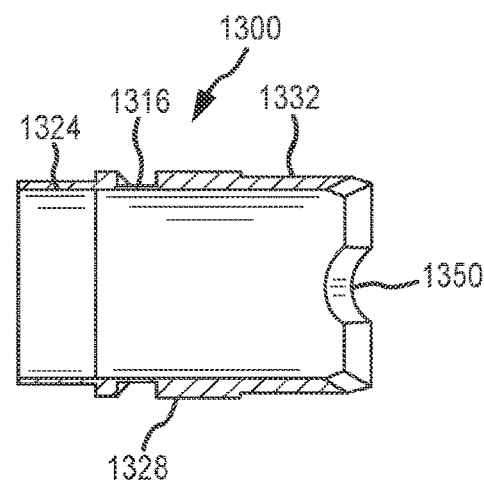
FIG. 13D is cross-sectional view of the inner band member illustrated in FIG. 13A taken along line 13D-13D in FIG. 13C.

Although the inner sheath and outer sheath are coupled to one another via the inner cam member, outer cam member, and pin, the sheaths may be coupled to one another in other ways. Stated differently, those of skill in the art will understand how to make and use the disclosed aspects, embodiments, and/or configurations after understanding the present disclosure to couple the sheaths in a manner to allow a cutting surface to extend and rotate beyond the distal end of the outer sheath. All such configurations within the knowledge of one skilled in the art are considered within the scope of this disclosure. For example, referring to FIGS. 5A and 5B, the assembly 500 may include an outer sheath 504 and an inner sheath 526 coupled to one another via pin 510 without the use of an outer cam member or inner member as in FIGS. 4B and 4C. The outer sheath 504 may have a pin 510 connected to it, and the inner sheath 526 may include cam slot 514 such that as the inner sheath 526 extends upon actuation of the actuation means discussed earlier herein, the inner sheath 526 along with its cutting surface, also rotates according to the cam slot 514 profile. While the inner sheath 526 extends and rotates, the outer sheath 504 and pin 510 remain stationary. FIG. 5A depicts the inner sheath 526 (and cutting surface 522) of assembly 500 in an initially retracted and stowed position. FIG. 5B depicts the inner sheath 526 (and cutting surface 522) of assembly 500' in an extended position. As the actuation means is actuated and unactuated, the assembly moves from a retracted position to an extended position and vice versa.

With reference to FIGS. 6A, 6B and 6C, an exemplary outer cam member 600 is depicted. The outer cam member 600 is a sleeve in the shape of a hollow cylinder. Although the exterior of the outer cam member 600 is uniform, it need not be. The interior of the outer cam member 600 is not uniform. For example, the interior of the outer cam member 600 includes an abutment 616 to prevent the inner cam member (not shown) from traveling further from the proximal end 612 to the distal end 608 within the outer cam member 600. The outer cam member 600 also includes a hole 604 for receipt and possible attachment of a pin (not shown) which protrudes radially inward. As discussed in more detail below, the pin engages the cam slot of the inner cam member. The size, shape and configuration of the outer cam member 600 may differ depending upon how it is attached to the flexible outer sheath. As discussed above, the outer sheath may be stationary. If so, the outer cam member 600 and the pin remain stationary as the inner cam member moves relatively thereto.

With reference to FIGS. 7A, 7B, 7C and 7D, an exemplary inner cam member 700 is depicted. The inner cam member 700 has a generally hollow cylindrical shape. The inner cam member 700 comprises a proximal portion 724, an intermediate portion 728, and a distal portion 732. The outside diameter of the proximal 724 is sized to allow the distal end 704 of the inner cam member 700 to be inserted to and engage (or otherwise attached to) the interior diameter of the inner flexible sheath (not shown). The distal end 708 of the inner cam member 700 comprises a cutting surface 712 having a flat, sharp blade profile. The intermediate portion 728 comprises a cam slot 716 cut within its exterior surface. As the inner flexible sheath rotates and moves within the outer sheath—from its proximal end to distal end—the outer sheath and pin may remain stationary. If so, the inner sheath, which is connected to the inner cam member, forces the inner cam member to rotate and move toward the distal end of the outer sheath. The cam slot 716 engages the pin, and the shape and profile of the cam slot 716 controls the rate and distance with which the inner cam member 700 travels. That is, the configuration of the cam slot controls how the inner cam member travels both laterally and rotationally.

Figure 14A:
FIG. 14A is side view of the outer member with the inner member of FIGS. 7A-7D positioned in a retracted position within the outer sheath.
Figure 14B:
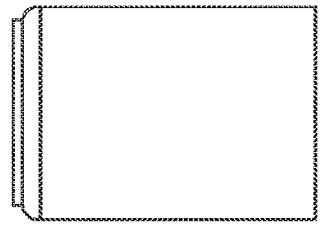
FIG. 14B is side view of the outer member with the inner member of FIGS. 7A-7D positioned in an extended position within the outer sheath.
Figure 15:
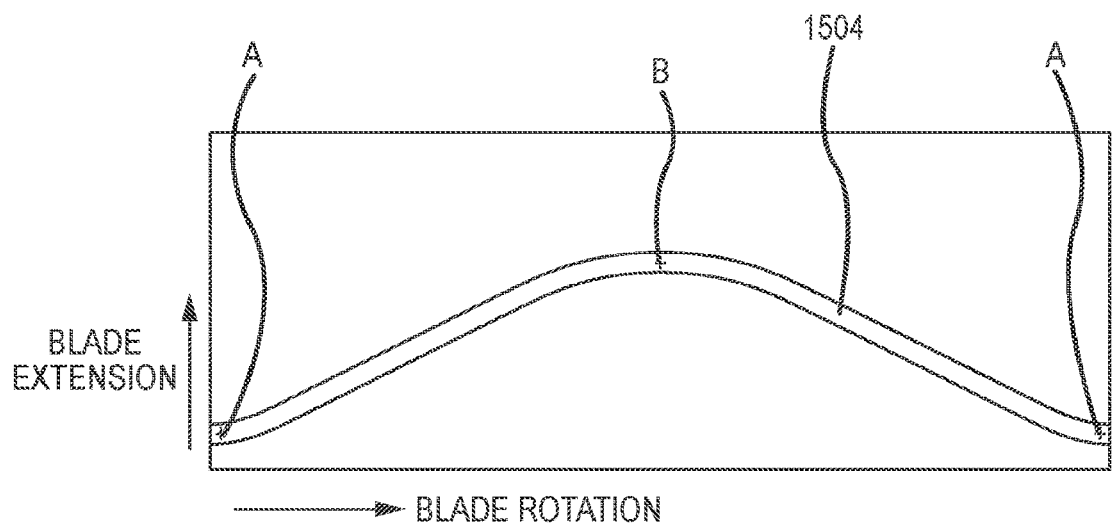
FIG. 15 is an illustration of the geometry of the cam slot of the inner member illustrated in FIGS. 7A-7D portrayed on a single plane.

The cam slot 716 in FIGS. 7A, 7B, 7C and 7D can have a linear profile (not shown). An alternative example of a two dimensional representation of the profile of the cam slot is depicted in FIG. 15. When the pin is position A on the left hand side of FIG. 15, the inner cam member (and blade) is in the retracted position, as depicted in FIG. 14A. As the inner cam member rotates about 180 degrees and extends (from left to right in FIG. 15), the cam slot 1504 travels along the pin from position A to position B at a relatively constant rate because the slope of the cam slot between these two points is relatively linear. That is, there is a substantially linear portion within the cam slot 1504 between position A and position B even though the overall shape of the cam slot 1504 is generally sinusoidal. The sinusoidal shape, particularly at the transition points, namely position A and position B, allows for a smooth transition from extension to retraction through such positions while maintaining a relatively constant rate of rotation. Upon reaching position B, the inner cam member is in its fully extended position, as depicted in FIG. 14B. As the inner cam member continues to rotate another 180 degrees, the cam slot travels along the pin from position B back to its original retraction position A at a relatively constant rate because the slope of the cam slot between these two points is relatively linear. FIG. 15 illustrates the cam slot 1504 in an open and continuous configuration. Accordingly, as the inner cam member continues to rotate beyond 360 degrees, the path of inner cam member is repeated and it continues to travel from position A to position B to position A. And due to the substantially linear configuration of the cam slot profile from position A to position B, and vice versa, the inner cam member (and blade) extends and/or rotates at a substantially constant rate between positions.

FIG. 15 also illustrates that the inner cam member (and blade) both extends and retracts for a predetermined amount of rotation. For example, assuming the blade is able to rotate 360 degrees, the blade extends from position A to position B in FIG. 15 for the first 180 degrees of rotation, and the blade retracts from position B to position A for the second 180 degrees of rotation. As discussed herein, as the trigger of the handle is linearly actuated, the inner cam member (and blade), via the coupled inner sheath, rotates a predetermined amount of degrees, and the inner cam member extends and retracts according to the inner cam member's cam slot profile. Accordingly, as the trigger of the handle is linearly actuated, the inner cam member (and blade) both extends and retracts while rotating. That is, the inner cam member (and blade) both extends and retracts according to the cam slot profile upon a single actuation of the trigger.

Referring again to FIGS. 7A, 7B, 7C and 7D, the inner cam member 700 may also comprise a step up 720 such that the diameter of the intermediate portion 728 is greater than the distal portion 732. As the inner cam member 700 rotates, and the cutting surface 712 extends beyond the distal end of the outer cam member into its extended position, the step up 720 of the inner cam member 700 contacts the abutment of the outer cam member, thereby limiting the distance that the inner cam member 700 may travel and/or may prevent the inner cam member from exiting or extending beyond the distal tip of the outer sheath (or outer cam member) in the event that the pin is sheared.

With reference to FIGS. 8A, 8B, 8C and 8D, and alternative exemplary inner cam member 800 is depicted. The inner cam member 800 depicted in FIGS. 8A-8D is similar to the inner cam member 700 depicted in FIGS. 7A-7D because the inner cam member 800 has a proximal portion 824, an intermediate portion 828, a distal portion 832 and a sharp cutting surface 712 with a flat profile at its distal end 808. Unlike the inner cam member 700, which has a linear cam slot profile, however, the inner cam member 800 has a cam slot 816, which when extended in a two-dimensional plane, has a non-linear profile. For example, an illustration of a two-dimensional, non-linear cam slot profile 1700 is depicted in FIG. 17.

Figure 16A:
FIG. 16A is a side view of the outer member with the inner member of FIGS. 8A-8D positioned in a retracted position within the outer sheath.
Figure 16B:
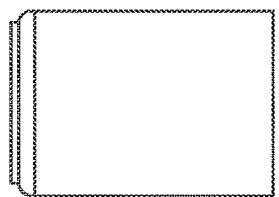
FIG. 16B is a side view of the outer member with the inner member of FIGS. 8A-8D positioned in a partially extended position within the outer sheath.
Figure 16C:
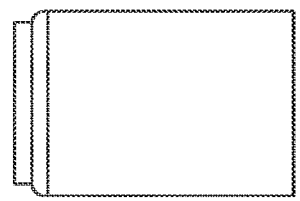
FIG. 16C is a side view of the outer member with the inner sheath of FIGS. 8A-8D positioned in a fully extended position within the outer member.
Figure 17:
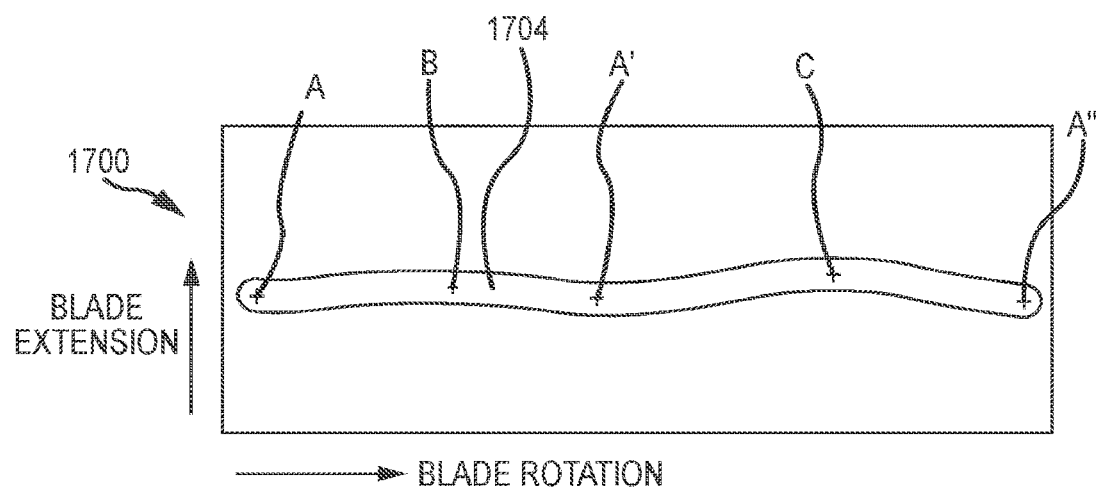
FIG. 17 is an illustration of the geometry of the cam slot of the inner member illustrated in FIGS. 8A-8D portrayed on a single plane.

Continuing to refer to FIG. 17, there is depicted cam slot 1704. As the flexible inner sheath extends distally within the outer sheath, the cooperation between the pin and the cam slot causes the inner cam member to also rotate and travel toward and beyond the distal end of the outer cam member. The rate and distance at which the inner cam member travels is dependent upon the configuration of the cam slot, particularly the slope of the cam slot. If the profile of the cam slot, such as its slope, is non-linear, then the rate and distance at which the inner cam member travels will vary as the inner cam member rotates and moves over the pin along the cam slot path. For example, when the inner cam member is in its fully retracted position (see FIG. 16A), the pin contacts the cam slot 1704 at position A identified as a first point marked+within the left hand side of FIG. 17. When the inner cam member is in its partially extended position (see FIG. 16B), the pin contacts the cam slot 1704 at a second point marked+and identified as position B within FIG. 17. When the inner cam member is in its fully extended position (see FIG. 16C), the pin contacts the cam slot 1704 at another point marked+and identified as position C within FIG. 17. This two-dimensional representation of the cam slot 1704 illustrates a non-linear profile of the cam slot because in order for the inner cam member to fully extend, it must travel at more than one rate from position A to position C. That is, the blade rotates at a first predetermined rate from position A to position B (partially extended position), and the blade rotates at a second predetermined rate from position A' to position C (fully extended position).

For example, as the inner cam member rotates and the pin contacts the cam slot 1704, the cutting surface travels at a rate according to the profile of the cam slot 1704 from its fully retracted position (see FIG. 16A) to a position that is slightly beyond the distal end of the outer cam member (see FIG. 16B) over about 90 degrees of rotation by the inner cam member. The profile of the cam slot from position A to position B is generally linear, thereby causing the inner cam member to travel at a generally constant rate between those two positions. As depicted in FIG. 17, the blade extends a predetermined distance for the about of rotation (90 degrees) from position A to position B. Once the blade travels to its partially extended position B, the blade continues to rotate and the blade returns to its retracted position A' over about 90 degrees of rotation by the inner cam member. The profile of the cam slot from position B to position A' is generally linear; therefore, the blade extends at a generally constant rate between those two positions. As the as the inner cam member continues to rotate and the pin contacts the cam slot 1704 beyond position A' and toward position C over about another 90 degrees of rotation, the blade extends a second predetermined distance. That is, the cutting surface travels beyond its partially extended position and to its fully extended position (see FIG. 16C). The profile of the cam slot from position A' to position C is difference than the profile of the cam slot from position A to position B. Although the profile of the cam slot from position A to position B is generally linear, the first predetermined amount of extension (from position A to position B) is less than the second predetermined amount of extension (from position A' to position C). Thus, the profile of the cam slot from position A to position B is such that the blade extends a shorter distance in comparison to extending from position A' to position C for a predetermined amount of rotation (90 degrees), thereby providing more precise and finer control of the blade as it rotates and extends. Moving an extending the inner cam member at a generally constant rate for a short distance provides the clinician precise control of the blade as it initially extends beyond the outer sheath. Stated differently, the profile of the cam slot from position A' to position C is such that the blade extends further and more quickly for a predetermined amount of rotation (90 degrees) after it is initially extended, thereby providing relatively less precision and coarser control of the blade in comparison to extending from position A to position B. Accordingly, the inner cam member and blade travel at a faster rate from position to A' to position C (and from position C to position A") in comparison to traveling from position A to position B. In order for the blade to fully extend to position C, the blade travels at more than one rate—one rate from position A to position B (and from position B to position A') and another rate from position A' to position C. Thus, even though the rates of travel from the position A to position B (and from position B to position A') and from position A' to position C may both be relatively constant for each individual portion of travel, the overall rate of travel is variable.

The discussion above discusses that the inner cam member travels at certain rates (e.g., constant, variable). However, the rates are also dependent upon the speed at which the inner sheath extends, and in turn, upon the speed of the means for actuating. For example, if the means for actuation includes a handle and one or more gears connecting the handle to the elongated inner sheath, then the rate at which the inner cam member rotates and extends is dependent upon how quickly the clinician operating the surgical device compresses the handle. Accordingly, the discussion and/or comparison of the rates at which the blade extends travels assumes that the means for actuating extends the inner sheath at a relatively constant speed. Regardless of whether this assumption is correct, the greater amount of blade extension per predetermined amount of rotation, the blade will extend at a greater rate and speed, thereby providing the surgical device with the ability to cut more tissue per rotation.

FIG. 17 also illustrates that the inner cam member (and blade) both extends and retracts a plurality of times for a predetermined amount of rotation. As discussed above with respect to FIG. 15, the inner cam member extends and retracts once over predetermined amount of rotation. FIG. 17, however, illustrates that the inner cam member, extends and retracts twice for a predetermined amount of rotation. Accordingly, as the trigger of the handle is linearly actuated, the inner cam member may both extends and retracts while rotating. That is, the inner cam member may extend and retract a plurality of times, according to the cam slot profile of the inner cam, when the inner sheath rotates a predetermined amount upon a single actuation of the trigger.

Although the discussion above with respect to FIGS. 8 and 17 only discuss a certain number of linear and non-linear profile portions of the cam slot, that discussion is not intended to limit the scope of this disclosure to only a fixed number of linear and non-linear profile portions. Depending upon the desired rate(s) at which the blade may rotate and extend, the cam slot may have additional multiple linear and non-linear profile portions of the cam slot. Those of skill in the art will understand how to make and use the disclosed aspects, embodiments, and/or configurations after understanding the present disclosure to adjust the distance, rate and rotational aspects at which the inner cam member (or other cam members) travels. All such configurations within the knowledge of one skilled in the art are considered within the scope of this disclosure.

As mentioned above, the cam slot profile of FIG. 15 is an open and continuous configuration, thereby allowing the inner cam member to continuously rotate. The cam slot profile of FIG. 17, however is a closed configuration such that when the inner cam member reaches its fully extended position (i.e., position C) or returns to position A", the actuation means must be releases or reversed so that the inner cam may return to initial retracted position A. Although certain figures in this disclosure only illustrated either the open or closed cam slot configuration, either configuration may be used with any of the inner cam embodiments disclosed and/or discussed herein and are considered within the scope of this disclosure. Additionally, the angular degree(s) to which the cam slots surround the circumference of the inner cam member, particularly its intermediate section, is not limited. For example, although the open cam slot typically surrounds 360 degrees of the circumference of the inner cam member, the scope of this disclosure includes an open cam slot profile surrounding more than 360 degrees of the circumference of the inner cam member. Also, the closed cam slot profile may surround the circumference of the inner cam member any number of times (i.e., 0.5, 0.75, 1.0, 1.25, 1.5, 1.75, 2.0, 2.25, 2.5, 2.75, 3.0, 3.25, 3.5, 3.75, 4.0, etc.)—either wholly or partially. Stated differently, the closed cam slot may surround the circumference of the inner cam member to produce any degree of actuation (e.g., between 0-1440 degrees) and any increment (e.g. 1.degree., 2.degree., 3.degree., 4.degree., 5.degree., 10.degree., 15.degree., 20.degree., 25.degree., etc.) thereof.

With reference to FIGS. 9A, 9B, 9C and 9D, an alternative exemplary inner cam member 900 is depicted. The inner cam member 900 depicted in FIGS. 9A-9D is similar to the inner cam member 900 depicted in FIGS. 8A-8D because the inner cam member 900 has a proximal portion 924, an intermediate portion 928, a distal portion 932, and a cam slot 916 that is similar to cam slot 816. Unlike the inner cam member 800, which has a smooth cutting surface, inner cam member 900 has a serrated cutting surface 912. The cutting surface 912 depicts fourteen (14) serrations. However, it may be preferable to have between twelve (12) and sixteen (16) serrations.

Although the cutting surface 912 illustrates a certain number of serrations, FIGS. 9A-9D are not intended to represent the only number and type of serrations that may be included in a serrated cutting surface. Depending upon the size of the surgical device, including the sheaths, and cam members, those of skill in the art will understand how to make and use the disclosed aspects, embodiments, and/or configurations after understanding the present disclosure to adjust the number, size and configurations of the serrations. All such configurations within the knowledge of one skilled in the art are considered within the scope of this disclosure. For example, referring to FIGS. 11A, 11B, 11C and 11D, an alternative exemplary inner cam member 1100 is depicted having a cutting surface 1112 comprising multiple serrations in the form of a crown. Also, referring to FIGS. 12A, 12B, 12C and 12D, an alternative exemplary inner cam member 1200 is depicted having a cutting surface 1212 comprising multiple serrations in the form of a hook crown. The cutting surface also need not be serrated, but merely include a plurality of notches formed therein. For example, with reference to FIGS. 13A, 13B, 13C and 13D, a further alternative exemplary inner cam member 1300 is depicted having a cutting surface with four notches 1350 included therein. Furthermore, the notches may comprise a myriad of different shapes and configurations, including but not limited to any variation of a square, rectangle, rhombus, parallelogram, trapezoid, triangle, circle, ellipse, kite, etc.

The cutting surface discussed hereinbefore with respect to FIGS. 7, 8, 9, 11, 12 and 13 are substantially parallel to the proximal edge of the inner cam members. In other words, the plane of the proximal end of the inner cam member and the plane of the distal end (e.g., cutting surface) of the inner cam member in these figures are substantially parallel. The proximal and distal ends of the inner cam member, however, need not be parallel or co-planer. Rather, any of the cutting surfaced depicted in FIGS. 7, 8, 9, 11, 12 and 13 may be offset from the plane of the proximal end of the inner cam member. With reference to FIGS. 10A, 10B, 10C and 10D, an alternative exemplary inner cam member 1000 is depicted. The plane of the cutting surface 1008 of the inner cam member 1000 is offset from a plane parallel to the plane of the proximal end 1004 of the inner cam member at an angle .alpha. It may be preferable for angle .alpha. to be at an angle between zero degrees and ninety degrees. The outer cam member may also have a distal end having a plane between zero degrees and ninety degrees, and the plane of the distal end of the outer cam may be the same or offset from the plane of the cutting surface of the inner cam.

The cam slots included within the inner cam members depicted FIGS. 7-13 surround the circumference of the inner cam member one time. It may advantageous, however, for the cam slot to surround the inner cam member's circumference more than once. For example, with reference to FIG. 18, there is depicted an inner cam member 1800 having a cam slot 1816 that travels more than 360 degrees around its circumference. The portion 1848 of the cam slot 1816 that is closest to the distal end 1808 of the inner cam member 1800 and that extends beyond the other end of the cam slot 1816 is substantially parallel to the planes of the proximal end 1804 and distal end 1808. The profile of cam slot 1816 depicted in one dimension is illustrated in FIG. 20 as the inner cam member 1800 moves from a retracted position (see FIG. 19A) to partially extended position (see FIG. 19B) and eventually to a fully extended position (see FIG. 19C).

The configuration and profile of portion 1848 of the cam slot 1816 prevents the inner cam member 1800 from moving from its retracted position, even if the inner cam member 1800 begins to rotate. That is, the inner cam member 1800 remains stowed in its retracted position as long as the pin engages only portion 1848 of cam slot 1816, thereby insuring that the blade is completely retracted as the clinician maneuvers the surgical device within the patient's vascular system. Referring to FIG. 20, there is depicted a two-dimensional cam slot profile of the configuration of the cam slot 1816 of FIG. 18. The cam slot profile depicted in FIG. 20 is similar to the configuration of the cam slot profile depicted in FIG. 17, with the exception that the cam slot profile depicted in FIG. 20 further includes a portion that surrounds the circumference of the inner cam member more than once. That is, the cam slot is included in about another 90 degrees of travel around the circumference of the inner cam member over and above the 360 degrees of travel. This additional portion—the portion that extends around the circumference of the inner cam member more than 360 degrees—is depicted as the substantially flat profile portion to the bottom right hand side of FIG. 20 that begins with a point marked+and identified as position A. This substantially flat profile portion insures that the blade remains stowed within the outer cam member as the inner cam member begins to rotate, thereby increasing the safety of the device and minimizing the likelihood of the blade being exposed beyond the distal end of the outer cam prior to actuation. Although FIG. 20 illustrates the flat portion of the cam slot as an extended in an embodiment with a cam slot greater than 360 degrees around the circumference of the inner cam member, the flat portion, which creates the stowed position, can be included within a cam slot that is equal to or less than 360 degrees around the circumference of the inner cam member.

With reference to FIG. 21, there is depicted an inner cam member 2100 having a cam slot 2116 that travels about 720 degrees around its circumference. The profile of cam slot 2116 depicted in two dimensions is illustrated in FIG. 23 as the inner cam member 2100 moves from a retracted position (see FIG. 22A) to a partially extended position (see FIG. 22B) and eventually to a fully extended position (see FIG. 22C). Referring to FIG. 23, the blade extends from position A, which corresponds to the retracted position of FIG. 22A, to position B, which corresponds to the partially extended position of FIG. 22B over about 180 degrees of rotation by the inner cam member 2100. The blade then retracts from position B to position A' over about 180 degrees of rotation by the inner cam member 2100. The blade can then extends from position A', which corresponds to the retracted position of FIG. 22A, to position C, which corresponds to the fully extended position of FIG. 22C over about 180 degrees of rotation by the inner cam member 2100. Lastly, the blade retracts from position C to position A" over about 180 degrees of rotation by the inner cam member 2100. The benefit of increasing the length of the cam slot 2116 to a length greater than the circumference of the inner cam member to twice as long as the circumference of the inner cam member (i.e., 720 degrees) in comparison to the cam slot of FIG. 17, which is only passes over the circumference one time (i.e., 360 degrees), is that the blade and inner cam member can rotate about twice as much for the same amount of extension.

Accordingly, the blade has the ability to rotate and potentially create a greater amount of cutting action against the tissue for a predetermined amount of extension.

The discussion above with respect to FIG. 23 explains how the blade travels according to the cam slot profile for a full 720 degrees of rotation because the inner cam member includes a double lobe cam profile. During actuation, however, the inner cam member does not need to travel the entire 720 degrees of rotation. For example, the clinician operating the surgical device can actuate the means for actuation such that the inner cam member repeats the travel from position A to position B rather than continuing onward to position C. Allowing the clinician to repeat the inner cam member's path of travel from position A to position B allows the clinician to operate the surgical device in precision cutting mode for a longer period of time. Alternatively, the clinician operating the surgical device can actuate the means for actuation such that the inner cam member repeats the travel from position A' to position C rather than restarting from position A and moving to position C. Allowing the clinician to repeat the inner cam member's path of travel from position A' to position C allows the clinician to operate the surgical device in a coarser cutting mode for a longer period of time. This allows the clinician to alternate the use of the surgical device in either a precision cutting mode or a coarse cutting mode, (2) by alternating between the precision cutting mode and the coarse cutting mode, and/or (3) using a variable mode, which includes the combination of both the precision cutting mode and coarse cutting mode.

As discussed above, although certain figures in this disclosure only illustrate either the open or closed cam slot configuration that provide for certain degrees of rotation of the inner cam, either the open or the closed cam slot configurations for any amount of rotation. Accordingly, any of the discussed open or closed cam slot configurations may be used with any of the inner cam embodiments disclosed and/or discussed herein and are considered within the scope of this disclosure. Additionally, although certain figures in this disclosure only illustrate certain cutting surfaces, any cutting surface may be used with any of the inner cam embodiments disclosed and/or discussed herein and are considered within the scope of this disclosure. For example, FIGS. 33-38 illustrate an inner cam member comprising a serrated blade, but any type of cutting surface may be used with the embodiments for the inner cams depicted in these figures.

Figure 33:
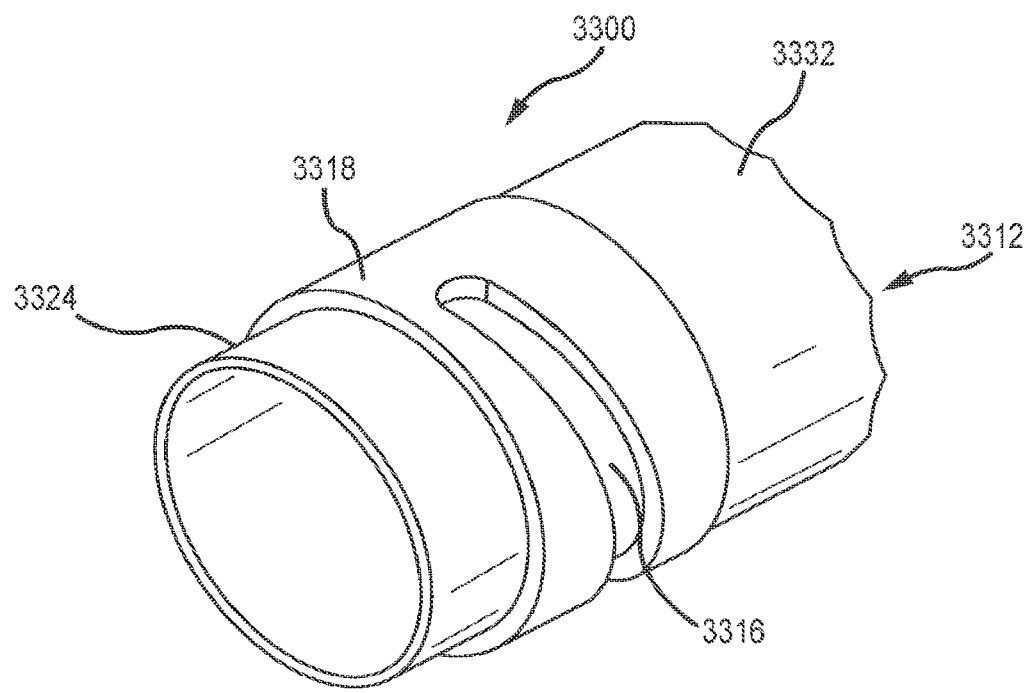
FIG. 33 is perspective view of an inner band member according to an embodiment of the disclosure.

Referring to FIG. 33, the inner cam member 3300 has a proximal portion 3324, an intermediate portion 3318, and a distal portion 3332. The distal portion 3332 of the inner cam member 3300 has a serrated cutting surface 3312. The inner cam member 3300 also has a cam slot 3316 having closed configuration with a generally linear profile. The cam slot 3316 surrounds about half the circumference of the intermediate portion 3318 of the inner cam member 3300. Accordingly, the closed cam slot profile allows the inner cam member 3300 to extend distally at a constant rate while rotating about 180 degrees.

Figure 34:
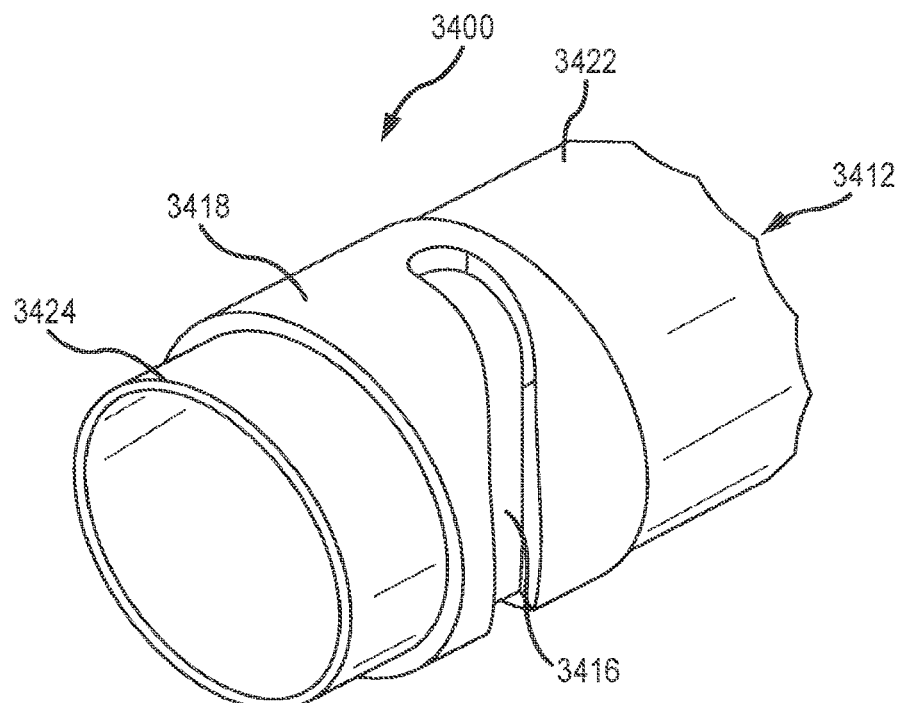
FIG. 34 is perspective view of an inner band member according to an embodiment of the disclosure.

Referring to FIG. 34, the inner cam member 3400 has a proximal portion 3424, an intermediate portion 3418, and a distal portion 3432. The distal portion 3432 of the inner cam member 3400 has a serrated cutting surface 3412. The inner cam member 3400 also has a cam slot 3416 having closed configuration with a generally sinusoidal profile. The cam slot 3416 surrounds about half the circumference of the intermediate portion 3418 of the inner cam member 3400. Accordingly, the closed cam slot profile allows the inner cam member 3300 to extend distally at a generally constant rate and retract proximally at a generally constant rate while rotating about 180 degrees. Unlike the inner cam member 3300 of FIG. 33, which has a generally linear profile and only allows for extension during 180 degrees of rotation, the sinusoidal profile of the cam slot 3414 of the inner cam member 3400 of FIG. 34 allows for both extension and retraction over 180 degrees of rotation while providing for a smooth transition between the extension and retraction. That is, the inner cam member 3400 extends while rotating about 90 degrees, and then retracts for the next 90 degrees of rotation in the same direction.

Figure 35:
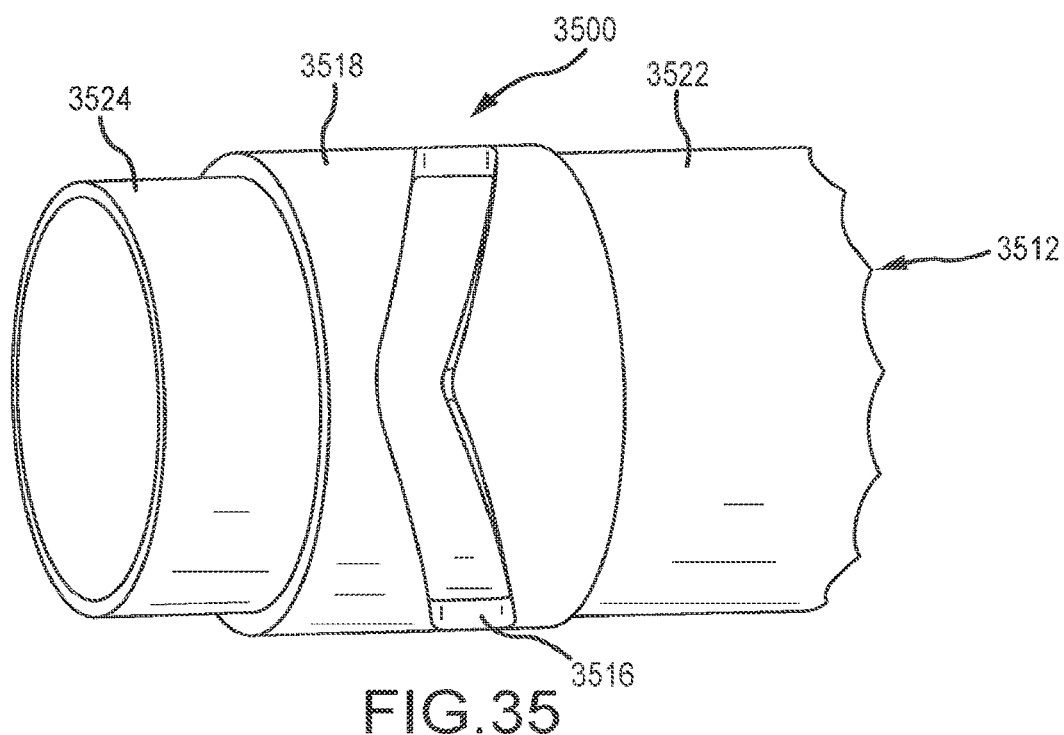
FIG. 35 is perspective view of an inner band member according to an embodiment of the disclosure.

Referring to FIG. 35, the inner cam member 3500 has a proximal portion 3524, an intermediate portion 3518, and a distal portion 3532. The distal portion 3532 of the inner cam member 3500 has a serrated cutting surface 3512. The inner cam member 3500 also has a cam slot 3516 having closed configuration with a generally "V" shaped profile. The cam slot 3516 surrounds about half the circumference of the intermediate portion 3518 of the inner cam member 3400. Accordingly, the closed cam slot profile allows the inner cam member 3500 to extend distally at a generally constant rate and retract proximally at a generally constant rate while rotating about 180 degrees. Similar to the inner cam member 3400 of FIG. 34, which has a generally sinusoidal profile, the "V" shaped profile of the cam slot 3514 of the inner cam member 3500 of FIG. 35 allows for both extension and retraction over 180 degrees of rotation. However, the "V" shaped profile of the cam slot 3514 has a sharper profile, and thereby creating a faster transition from extension to retraction at about the 90 degree transition point.

Figure 36:
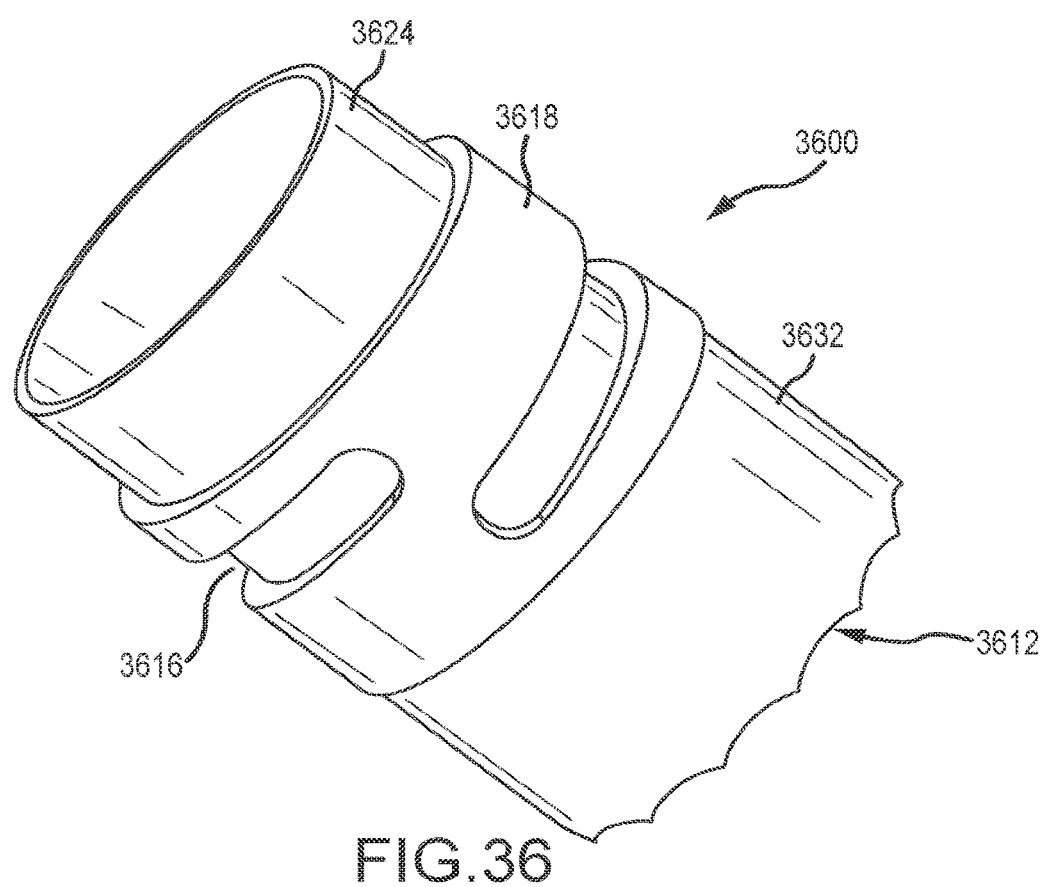
FIG. 36 is perspective view of an inner band member according to an embodiment of the disclosure.

Referring to FIG. 36, the inner cam member 3600 has a proximal portion 3624, an intermediate portion 3618, and a distal portion 3632. The distal portion 3632 of the inner cam member 3600 has a serrated cutting surface 3612. The inner cam member 3600 also has a cam slot 3616 having a closed configuration with a generally linear profile. The cam slot 3616 surrounds almost the entire circumference of the intermediate portion 3618 of the inner cam member 3600. That is, the cam slot 3616 is included in about 360 degrees of the circumference of the intermediate portion 3618 of the inner cam member 3600. In comparison to FIG. 33, which includes an inner cam member 3300 having a generally linearly shaped cam slot 3316 with a closed configuration surrounding about half the circumference of the intermediate portion 3318 of the inner cam member 3300, the inner cam member 3600 of FIG. 36 has a generally linearly shaped cam slot 3616 with closed configuration surrounding almost the entire circumference of the intermediate portion 3618 of the inner cam member 3600. Accordingly, the cutting surface 3612 of the inner cam member 3600 may extend (and/or retract) a greater distance and/or extend (and/or retract) at a slower rate in comparison to the cutting surface 3312 of the inner cam member 3300 because the cam slot 3616 of the inner cam member 3600 of FIG. 36 is longer than the cam slot 3316 of the inner cam member 3300 of FIG. 33.

Figure 37:
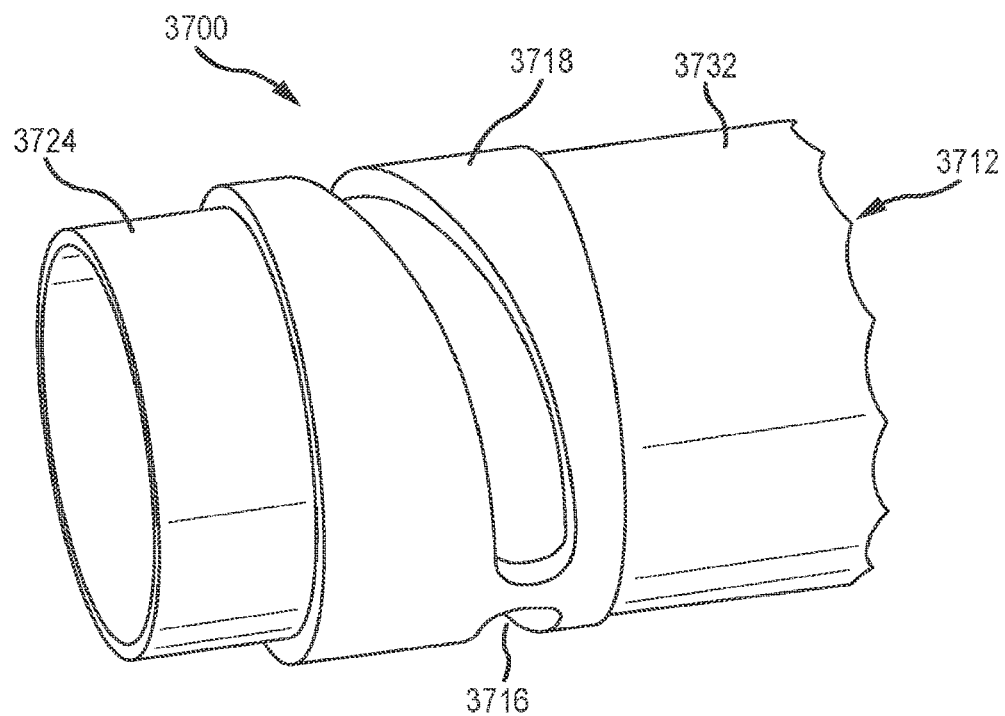
FIG. 37 is perspective view of an inner band member according to an embodiment of the disclosure.

Referring to FIG. 37, the inner cam member 3700 has a proximal portion 3724, an intermediate portion 3718, and a distal portion 3732. The distal portion 3732 of the inner cam member 3700 has a serrated cutting surface 3712. The inner cam member 3700 also has a cam slot 3716 having closed configuration with a generally sinusoidal profile. The cam slot 3716 surrounds almost the entire circumference of the intermediate portion 3718 of the inner cam member 3700. That is, the cam slot 3716 is included slightly less than 360 degrees around the circumference of the intermediate portion 3718 of the inner cam member 3700. In comparison to FIG. 34, which includes an inner cam member 3400 having a generally sinusoidal shaped cam slot 3416 with a closed configuration surrounding about half the circumference of the intermediate portion 3418 of the inner cam member 3400, the inner cam member 3700 of FIG. 37 has a generally sinusoidal shaped cam slot 3716 with closed configuration surrounding almost the entire circumference of the intermediate portion 3718 of the inner cam member 3700. Accordingly, the cutting surface 3712 of the inner cam member 3700 may extend and retract a greater distance and/or extend and retract a slower rate in comparison to the cutting surface 3412 of the inner cam member 3400 because the cam slot 3716 of the inner cam member 3700 of FIG. 37 is longer than the cam slot 3416 of the inner cam member 3400 of FIG. 34.

Figure 38:
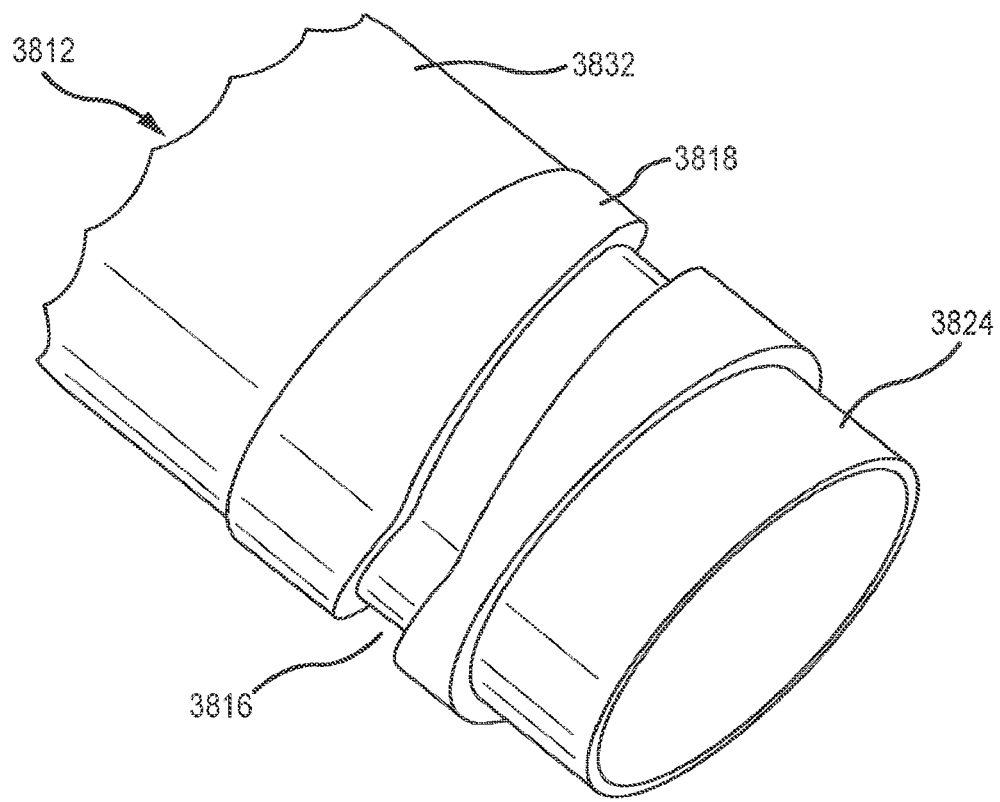
FIG. 38 is perspective view of an inner band member according to an embodiment of the disclosure.

Referring to FIG. 38, the inner cam member 3800 has a proximal portion 3824, an intermediate portion 3818, and a distal portion 3832. The distal portion 3832 of the inner cam member 3800 has a serrated cutting surface 3812. The inner cam member 3800 also has a cam slot 3816 having closed configuration with a generally "V" shaped profile. The cam slot 3816 surrounds almost the entire circumference of the intermediate portion 3818 of the inner cam member 3800. That is, the cam slot 3816 is included slightly less than 360 degrees around the circumference of the intermediate portion 3818 of the inner cam member 3800. In comparison to FIG. 35, which includes an inner cam member 3500 having a generally "V" shaped cam slot 3516 with a closed configuration surrounding about half the circumference of the intermediate portion 3518 of the inner cam member 3500, the inner cam member 3800 of FIG. 38 has a generally "V" shaped cam slot 3816 with closed configuration surrounding almost the entire circumference of the intermediate portion 3818 of the inner cam member 3800. Accordingly, the cutting surface 3812 of the inner cam member 3800 may extend and retract a greater distance and/or extend and retract a slower rate in comparison to the cutting surface 3512 of the inner cam member 3500 because the cam slot 3816 of the inner cam member 3800 of FIG. 38 is longer than the cam slot 3516 of the inner cam member 3500 of FIG. 35.

As previously discussed with respect to FIG. 4, the distal end of the flexible outer sheath 404 may be smooth and evenly rounded at its most distal point. Alternatively, the distal end of the outer sheath may not be smooth. Rather, the distal end of the outer sheath may be uneven in order to increase the outer sheath's ability to engage tissue. By engaging tissue, the outer sheath may increase its ability to remain stationary within the subject's vascular system as the inner cam member and blade rotate and extend into such tissue, thereby potentially minimizing undesirable rotation and/or movement of the outer sheath or surgical device.

FIGS. 29A, 29B, 29C and 29D depict a distal tip 2900 of the outer sheath according to an embodiment of the disclosure. The distal tip 2900 illustrated in these figures is depicted as a separate component. Those of skill in the art will understand how to make and use the disclosed aspects, embodiments, and/or configurations of the distal tip after understanding the present disclosure to adjust the location, size, configuration and/or type of indicator. For example, the distal tip, particularly its uneven configuration, may be created in the distal portion of the outer sheath, the outer cam member and/or combination of the outer sheath and outer cam member. All such configurations within the knowledge of one skilled in the art are considered within the scope of this disclosure. For the purposes of this disclosure, the "distal tip," particularly the distal tip of the outer sheath, shall mean and include a separate component attached to the outer sheath, the distal portion of the outer sheath, the outer cam member located at the distal end of the sheath, a combination of any of the preceding, and/or any other distal portion or component of the surgical device intended to contact tissue.

Continuing to refer to FIGS. 29A-29D, distal tip 2900 has a proximal end 2908 and a distal end 2912. The proximal end 2908 of the distal tip 2900 extends from or is attached to the outer sheath, the outer cam member, etc., and/or a combination thereof. The distal tip 2900 also includes a plurality of notches 2904 extending proximally from its distal end 2912. The notches 2904 create an uneven profile at the distal end 2912 of the distal tip, and this uneven profile facilitates the distal tip's engagement with the tissue or other material within the subject's vasculature, thereby holding the outer sheath stationary while the blade rotates and extends into the tissue.

FIGS. 29A-29D depicts six notches 2904 that have a generally rectangular shape that taper upwardly from the distal end 2904 toward the proximal end 2908 until the notches intersect and become flush with the exterior surface of the distal tip 2900. The notches 2904 are formed by removing material from the distal end 2904 of the distal tip. Notches may also be formed by adding material at predetermined intervals along the perimeter of the distal tip, such that the notches are created and located between the additional materials. Depending upon the size and configuration of the surgical device, particularly its distal tip, those of skill in the art will understand how to make and use the disclosed aspects, embodiments, and/or configurations after understanding the present disclosure to adjust the number, location, size, configuration and/or type of notches. All such notch configurations within the knowledge of one skilled in the art are considered within the scope of this disclosure.

With reference to FIGS. 30A-30D there is depicted an alternative exemplary distal tip 3000 has a proximal end 3008 and a distal end 3012. The notches 3104 included within this distal tip 3000 have a generally narrower rectangular shape in comparison to the notches 2904 of distal tip 2900 depicted in FIGS. 29A-29D. Due to the narrower configuration of the notches 3014 illustrated in FIGS. 30A-30D, the distal tip 3000 includes three times as many notches, for a total of eighteen, in comparison to the number of notches 2904 in distal tip 2900. Although FIGS. 29A-D and FIGS. 30A-D depict rectangular shaped notches 2904, 3004, the distal tip may include notches of any desirable shape that will engage tissue, including but not limited to any variation of a square, rhombus, parallelogram, trapezoid, triangle, circle, ellipse, kite, etc. For example, FIGS. 31A-31D depict a further alternative exemplary distal tip 3100 having V-shaped notches 3104 extending from distal end 3112 toward proximal end 3108.

The notches 2904, 3004, and 3104 included in distal tips 2900, 3000, and 3100, respectively, are configured to engage tissue and to prevent the outer sheath from rotating as the blade rotates and extends into such tissue. Inclusion of the notches in the outer sheath may also enhance the surgical devices ability to cut tissue because the combination of notches within the distal tip and notches within the cutting surface of the inner cam member may create a shearing force, thereby increasing the overall amount of cutting force applied to the tissue. Accordingly, the notches of the distal tip may also be configured to include a sharp blade profile, such as the serrated and notched blades depicted in FIGS. 9, 11, 12 and 13 and any equivalents thereof.

Figure 32A:
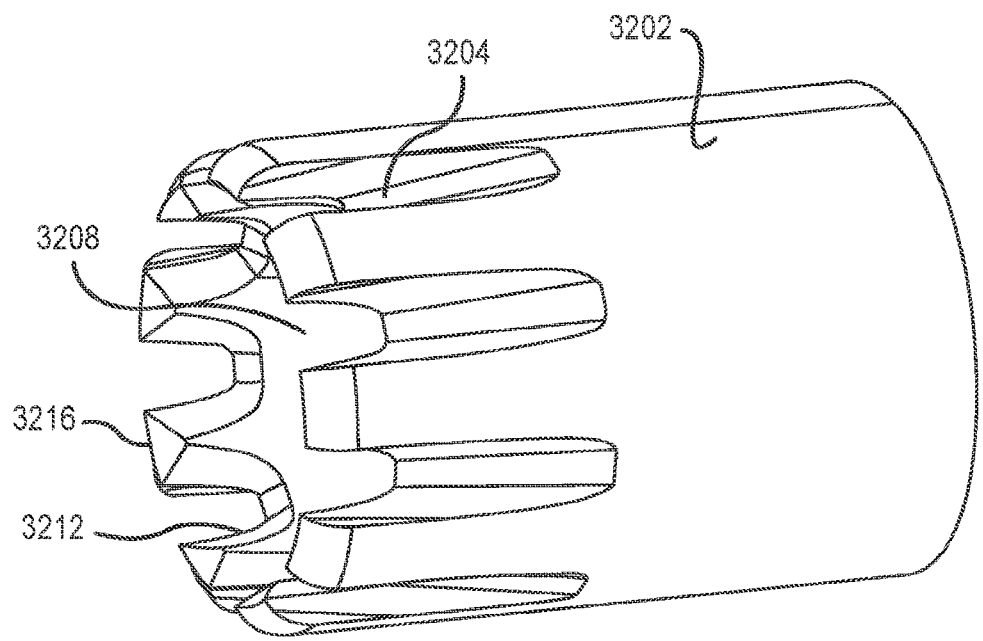
FIG. 32A is a perspective view of an inner member in a retracted position within a distal tip of an outer according to an embodiment of the disclosure.
Figure 32B:
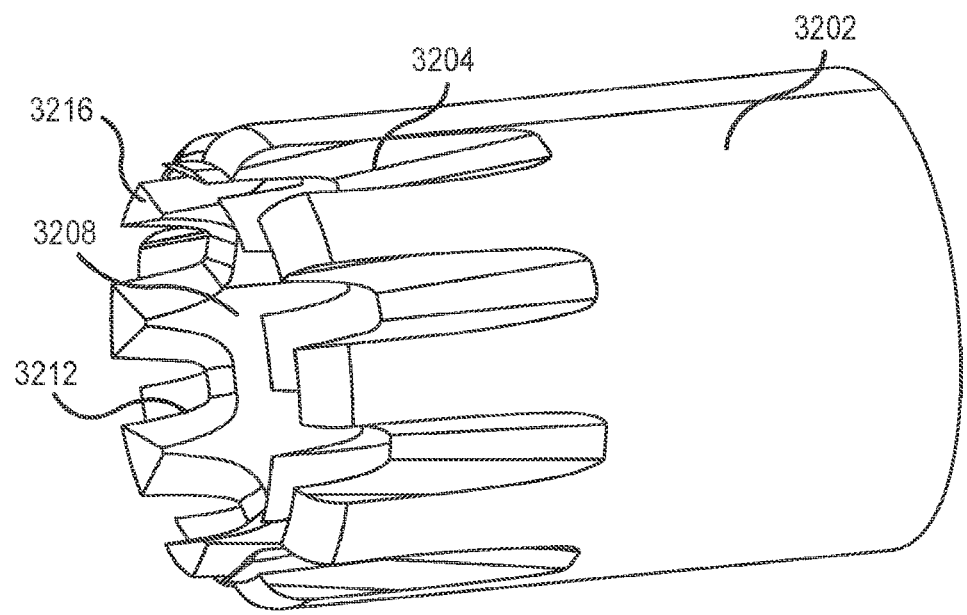
FIG. 32B is a perspective view of the inner member of FIG. 32A in an extended or partially extended position with respect to the distal tip.

With reference to FIGS. 32A and 32B, there is depicted a distal tip 3202 and an inner cam member 3208. The inner cam member 3208 has a plurality of notches 3212 creating a serrated-type blade, and distal tip 3202 has a plurality of notches 3204 that have a substantially similar size and shape as the notches 3212 within the inner cam member 3208. FIG. 32A depicts the inner cam member 3208 in a retracted position because the cutting surface does not extend beyond the distal end of the distal tip. When the inner cam member 3208 is in its distal portion, it may be preferable that the notches 3204, 3212 of the inner cam member 3208 and the distal tip 3202 substantially align in order to improve the surgical device's ability, particularly the distal tip's ability, to engage tissue. Referring to FIG. 32B, as the inner cam member 3208 begins to rotate and extend outwardly from its retracted position, the serrations 3216 begin to pass over the notches 3204 in the distal tip 3202, thereby creating a shearing force against the tissue and potentially increasing the device's cutting ability.

Figure 24:
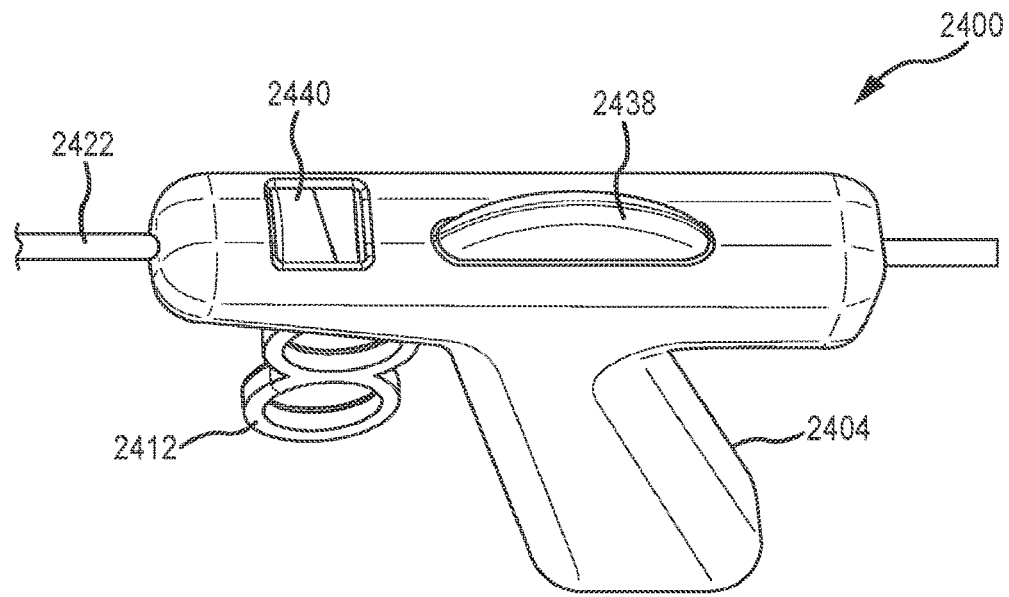
FIG. 24 is a perspective view of an embodiment of a handle portion, including an indicator, of the surgical device.

With reference to FIG. 24, there is a depicted an alternative embodiment of surgical device 2400 that comprises and indicator 2440 indicative of how far the blade of the inner cam member has traveled and/or has traveled beyond the distal end of the outer sheath. The indicator 2440 in FIG. 24 is located on the top of the distal portion of the handle 2404. Specifically, the indicator 2440 is located between the distal end of the handle 2404 and a vertically extending portion 2438 of the handle that encases components, such as gears, within the handle 2404. Indicator 2440 may include indicia, such as numbers or dimension indicative of the length that the blade has traveled and/or has traveled beyond the distal end of the outer sheath. In addition and/or in lieu of the indicia, the indicator 2440 may include color coded regions (e.g., green, yellow, orange, red, etc.), such that differently colored regions convey to the clinician whether it is more or less safe to move the entire surgical device, including the sheaths, within the patient's vasculature depending upon whether the cutting blade is exposed and/or how much of it is exposed. The indicator 2440 may also be directly and/or indirectly connected to the actuating means of the surgical device.

Figure 25:
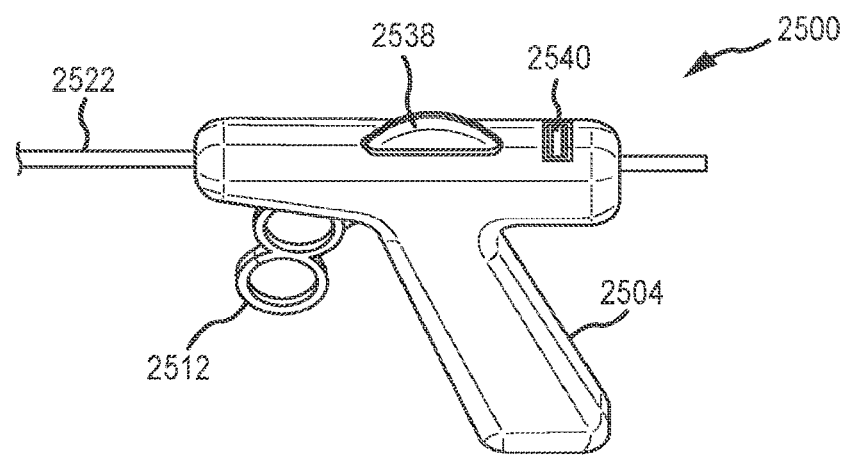
FIG. 25 is a perspective view of an alternate embodiment of a handle portion, including an alternate indicator, of the surgical device.
Figure 26:
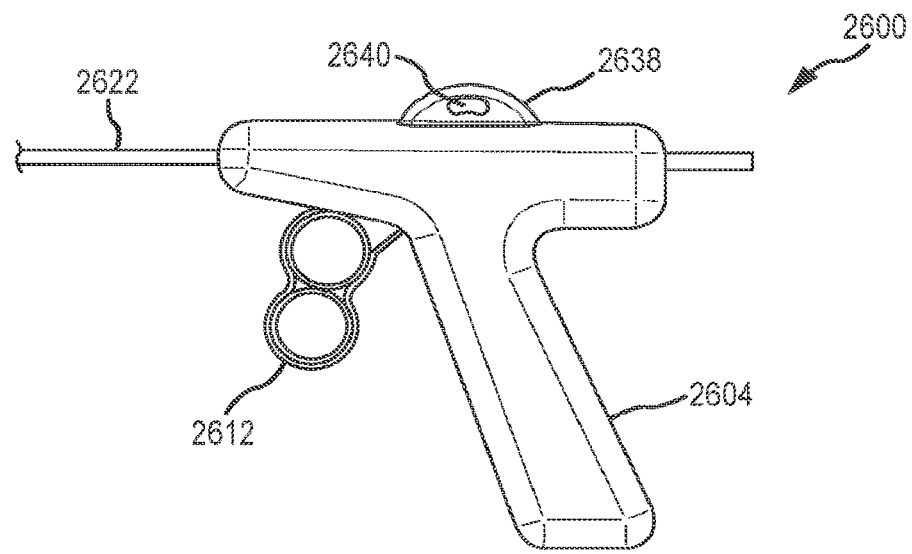
FIG. 26 is a side view of an alternate embodiment of a handle portion, including an alternate indicator, of the surgical device.
Figure 27:
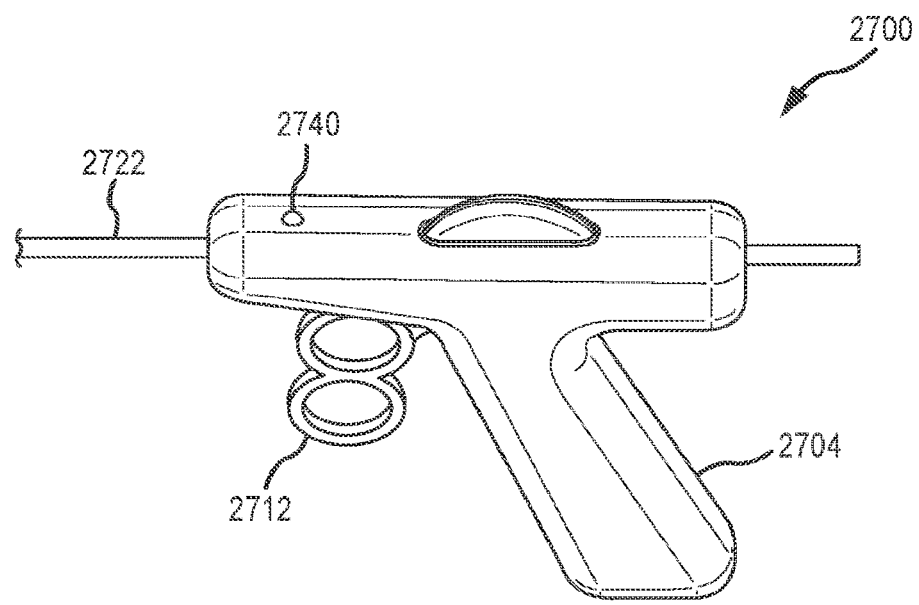
FIG. 27 is a perspective view of an alternate embodiment of a handle portion, including an alternate indicator, of the surgical device.

Although the indicator 2440 in FIG. 24 is located on the top of the distal portion of the handle 2404, FIG. 24 is not intended to represent the only location and type of indicator that may be included in a serrated cutting surface. Depending upon the size and configuration of the surgical device, particularly its handle and actuating mechanism(s), those of skill in the art will understand how to make and use the disclosed aspects, embodiments, and/or configurations after understanding the present disclosure to adjust the location, size, configuration and/or type of indicator. All such configurations within the knowledge of one skilled in the art are considered within the scope of this disclosure. For example, referring to FIG. 25, an alternative exemplary surgical device 2500 comprising an indicator 2540 depicted on the proximal, top portion of handle 2504. Also, referring to FIG. 26, an alternative exemplary surgical device 2600 comprising an indicator 2640 depicted on the side of the handle 2640, particularly, the indicator 2640 is located on a vertically extending portion 2638 of the handle 2604 that encases components, such as gears. The indicator also does not need to be mechanically actuated indicator. For example, if a motor is used to actuate the sheath, the indicator can be color-coded light, or other type of electrically based indicators, located on the top of the handle as depicted with reference to FIG. 27. Additionally, the color (e.g., green, yellow, orange, red, etc.) of the light, the brightness of the light and/or whether light remains constant or blinks (including the frequency of blinking) may change as the blade travels from its retracted position to its extended position.

Additionally, the indicator need not be located on the surgical device or any portion thereof, such as the handle. Rather, the indicator can be located external to the surgical device. That is, the surgical device may include a communication port that transmits the indictor signal(s) to a remote display and/or a remote device. For example, the surgical device may be connected to a remote fluoroscopy monitor, either via a cable or wirelessly, thereby allowing the monitor to display the position of the cutting surface (i.e., blade), inner cam, inner sheath and/or any other component of the surgical device. Transmitting the device's positional information to the monitor potentially allows the clinician to view the position of the blade on the same monitor that the clinician is using to perform the surgical procedure while navigating the patient's vasculature.

Figure 40A:
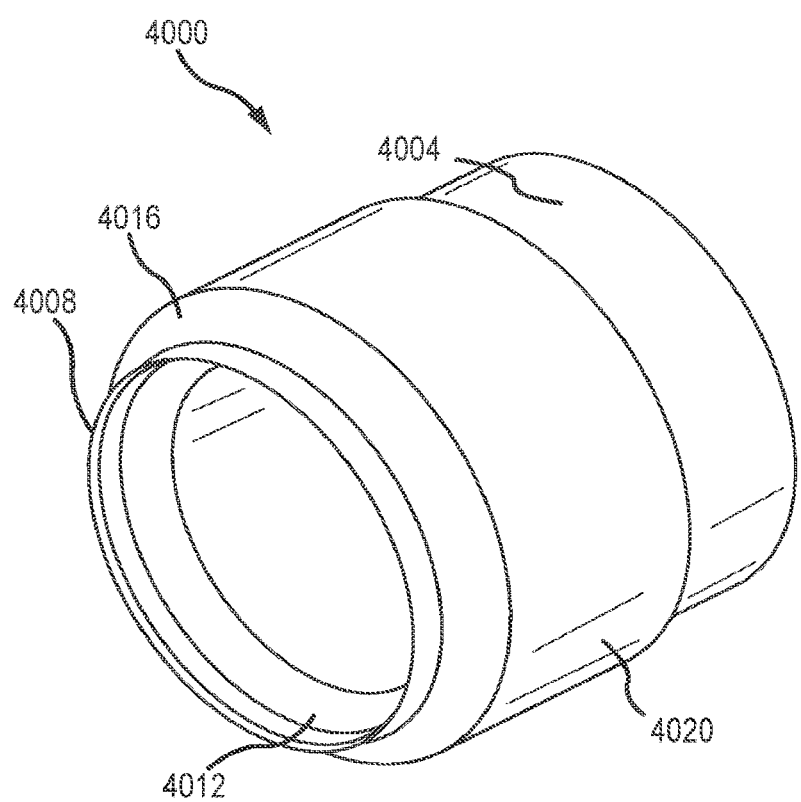
FIG. 40A is perspective view of an outer cam member, an inner cam member, a tubular inner member with a cutting blade therebetween according to an embodiment of the disclosure.
Figure 40B:
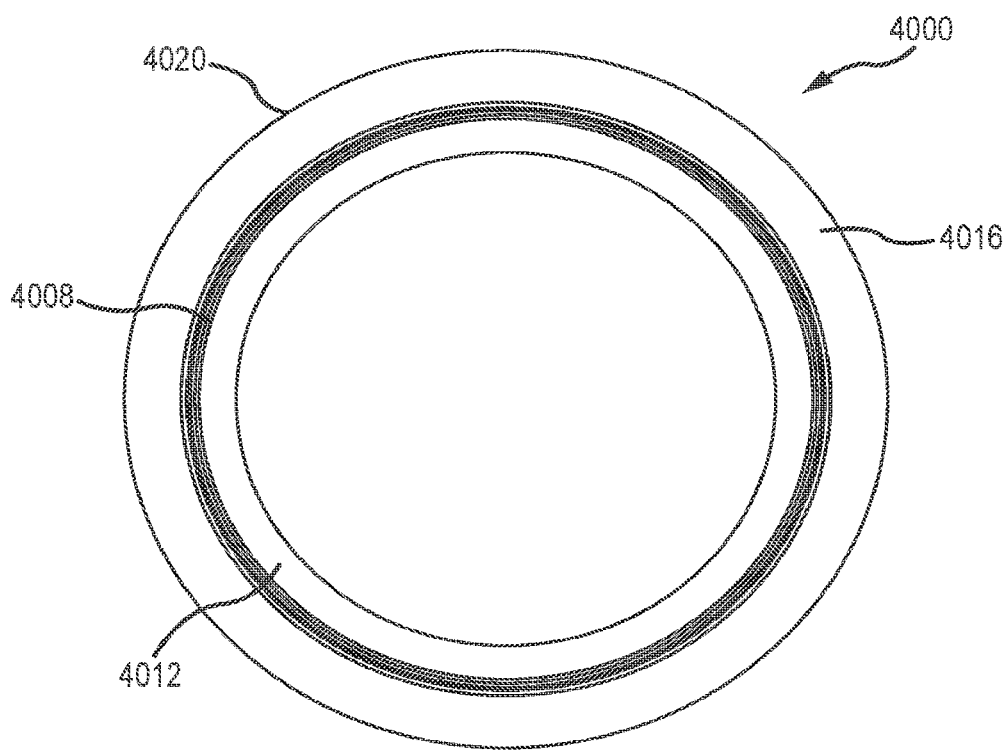
FIG. 40B is a distal end view of the outer sheath depicted in FIG. 40A.

Referring to FIGS. 40A and 40B, there is depicted an illustration of an embodiment of the distal end 4000 of the inner sheath and the outer sheath. The component of the inner sheath depicted in these figures is the inner cam member. The inner cam member, as depicted, has a cutting surface 4008 as well as an optional circular hollow inner member 4012 located within the lumen of the cutting blade. The component of the outer sheath depicted in these figures is the outer cam member 4004. As discussed hereinbefore, the outer cam member 4004 has a distal portion 4020. The circular hollow inner member may be integral with the inner cam or it may be a separate component. If the circular hollow inner member is a separate component it may be affixed or coupled to the inner cam member at a location proximal of the distal end. The most distal region of the distal portion 4020 of the outer cam member 4004 may be referred to as a distal end region 4016. The distal end region 4016 is tapered, and the taper may be linearly, curved and/or radially shaped.

The outer cam member 4004 has a wall thickness, and the wall thickness depicted in FIGS. 40A and 40B is consistent around the entire circumference of the outer cam member 4004 for a given cross section. That is, even though the wall thickness is thinner and decreases at the distal end region 4016 of the outer cam member in comparison to the wall thickness for a more proximal portion of the distal portion 4020, the wall thickness is the same or substantially the same at any point around the cross-section of the outer cam member 4004. As discussed herein, the outer cam member 4004 shields the blade, particularly the cutting surface 4008, from the vasculature when the blade is retracted. The outer cam member 4004 also creates a distance between the cutting surface 4008 and the vasculature when the blade is extended. And as the wall thickness of the outer cam member 4004 increases, so does the distance between the blade and the vasculature.

The circular hollow inner member 4012 has a wall thickness, and the wall thickness depicted in FIGS. 40A and 40B is consistent around the entire circumference of the circular hollow inner member 4012 for a given cross section. That is, if the wall thickness is thinner and decreases at the distal end of the circular hollow inner member 4012 in comparison to the wall thickness for the more proximal portion of the circular hollow inner member 4012, the wall thickness is the same or substantially the same at any point around the cross-section of the circular hollow inner member 4012. The circular hollow inner member 4012 acts to guide the lead during introduction into the lumen(s) of the inner and outer sheaths. The circular hollow inner member 4012 also acts to direct the lead toward the center of the lumen of the inner cam member and away from the cutting surface 4008. And as the wall thickness of the circular hollow inner member 4012 increases, the lead is more likely to be located at the center of the lumen of the inner cam member and further away from the blade. This may be helpful during extension (or retraction) of the blade and cutting surface 4008, thereby potentially reducing the likelihood of the cutting surface 4008 cutting the lead during extension.

Figure 41A:
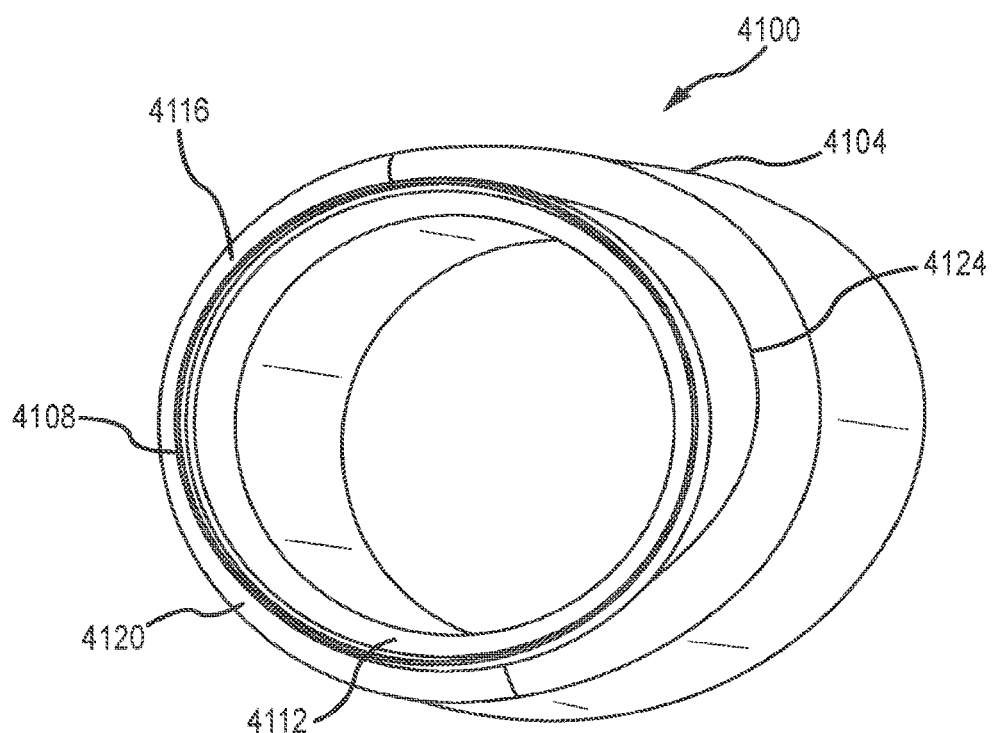
FIG. 41A is perspective view of an outer cam member, an inner cam member, a tubular inner member with a cutting blade therebetween according to an embodiment of the disclosure.
Figure 41B:
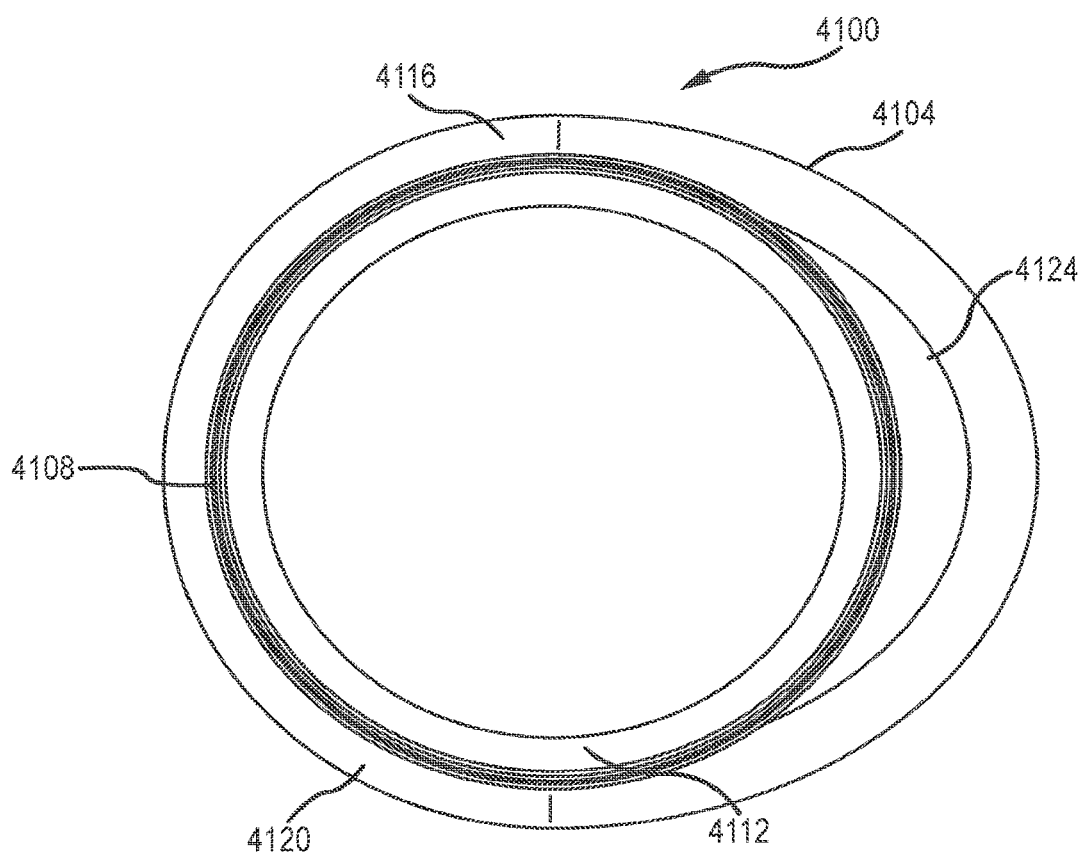
FIG. 41B is a distal end view of the outer sheath depicted in FIG. 41A.

Referring to FIGS. 41A and 41B, there is depicted an illustration of an embodiment of the distal end 4100 of the inner sheath and the outer sheath. The component of the inner sheath depicted in these figures is the inner cam member. The inner cam member, as depicted, has a cutting surface 4108 as well as an optional circular hollow inner member 4112 located within the lumen of the cutting blade. The component of the outer sheath depicted in these figures is the outer cam member 4104. The outer cam member 4104 has a distal portion, and the most distal region of the distal portion of the outer cam member 4004 may be referred to as a distal end region 4116. The distal end region 4116 is tapered, and the taper may be linearly, curved and/or radially shaped.

Unlike the wall thickness of the outer cam member 4014 in FIGS. 40A and 40B, the outer wall thickness of the outer cam 4104 in FIGS. 41A and 41B is not uniform around the circumference for a given cross section of the outer cam member 4104. That is, the wall thickness is less or thinner at a portion 4120 of the cross section of the outer cam member 4104 in comparison to another portion 4124 for the same cross section. In other words, the wall thickness is greater or thicker at a portion 4124 of the cross section of the outer cam member 4104 in comparison to another portion 4120 for the same cross section.

It may be desirable for the outer cam member 4104 and/or other portions of the outer sheath to have a non-uniform wall thickness for a given cross section such that the distance between the blade 4108 and the exterior of the outer cam member 4104 is greater at one or more portions along the circumference at a particular cross section in comparison to the other portion(s) of the cross section. Increasing the cross-sectional wall thickness for one or more portions of the outer sheath, particularly at the distal portion and the distal end region 4116 of the outer cam member 4104, assists in shielding the vasculature from the blade 4108 during extension because the increased wall thickness creates a greater distance between the vasculature and the blade in comparison to the remainder of the cross section. And increasing the wall thickness of a portion of the circumference of the cross section of the outer cam member 4104 may allow the clinician to orient the sheaths in particular radial direction in a safer manner while navigating the patient's vasculature. For example, it may be beneficial for the increased wall thickness of the outer cam 4104 to be adjacent the exterior of a curved section of vasculature in comparison to the interior curved section of the vasculature to further minimize the likelihood of inadvertent contact from the blade.

Continuing to refer to FIGS. 41A and 41B, thicker and thinner portions (or segments) of the outer cam member 4104 may be adjacent and/or opposite one another along a cross section of a circumference of the outer cam member 4104. As illustrated in these figures, the exterior of the outer cam member 4104 is designed such that the thicker and thinner cross-sectional portions transitions to and from one another without interruption along the exterior surface of the outer cam member, thereby creating a smooth and unpronounced transition between a thicker wall portion and thinner wall portion. Unlike the cross section of the outer cam member 4104, the circular hollow inner member 4112 illustrated in FIGS. 41A and 41B has a wall thickness that is consistent around the entire circumference of the circular hollow inner member 4112 for a given cross section and is, therefor, similar to the circular hollow inner member 4012 discussed hereinbefore with respect to FIGS. 40A and 40B.

Figure 42A:
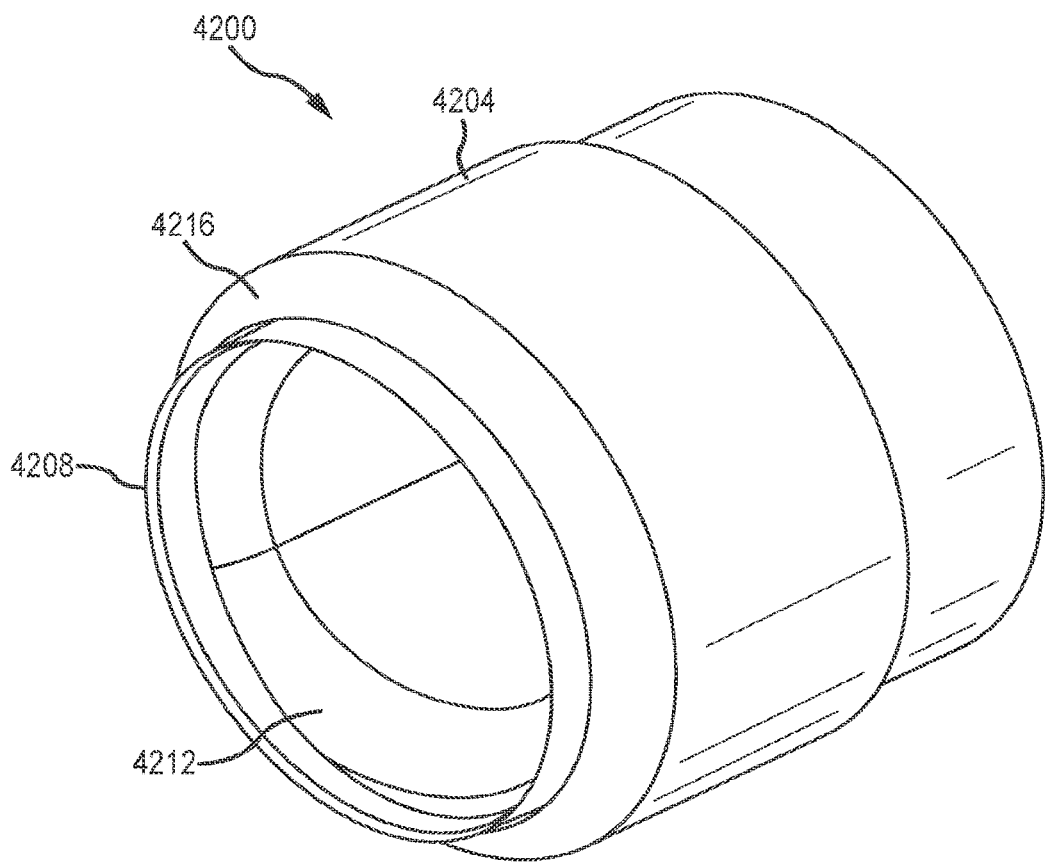
FIG. 42A is perspective view of an outer cam member, an inner cam member, a tubular inner member with a cutting blade therebetween according to an embodiment of the disclosure.
Figure 42B:
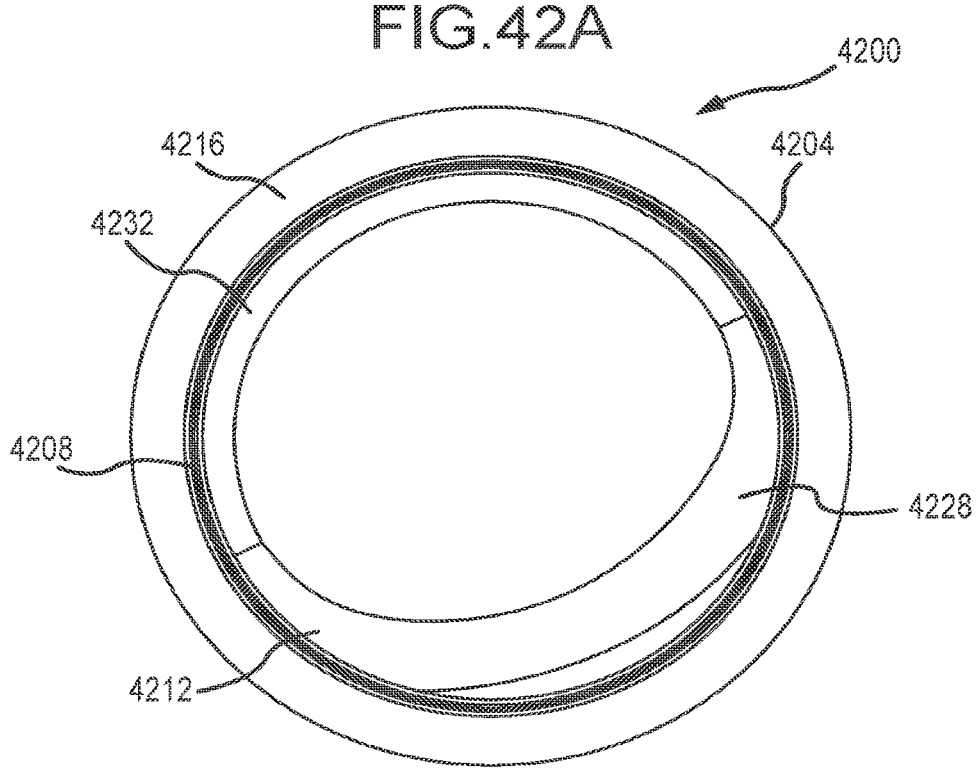
FIG. 42B is a distal end view of the outer sheath depicted in FIG. 42A.

Referring to FIGS. 42A and 42B, there is depicted an illustration of an embodiment of the distal end 4200 of the inner sheath and the outer sheath. The component of the inner sheath depicted in these figures is the inner cam member. The inner cam member, as depicted, has a cutting surface 4208 and a circular hollow inner member 4212 located within the lumen of the cutting blade. The component of the outer sheath depicted in these figures is the outer cam member 4204. The outer cam member 4204 has a distal portion 4020, which has a distal end region 4216. The distal end region 4216 is tapered, and the taper may be linearly, curved and/or radially shaped. The outer cam member 4204 illustrated in FIGS. 42A and 42B has a wall thickness that is consistent around the entire circumference of the outer cam member 4204 for a given cross section and is, therefore, similar to the outer cam member 4204 discussed hereinbefore with respect to FIGS. 40A and 40B.

The circular hollow inner member 4212 has a wall thickness. Unlike wall thickness of the circular hollow inner member 4012 in FIGS. 40A and 40B, the thickness of the circular hollow inner member 4212 in FIGS. 42A and 42B is not uniform around the circumference for a given cross section. That is, the wall thickness is thinner at a portion 4232 of the cross section of the circular hollow inner member 4212 in comparison to another portion 4228 for the same cross section. In other words, the wall thickness is greater at a portion 4228 of the cross section of the circular hollow inner member 4212 in comparison to another portion 4232 for the same cross section. State differently, the wall thickness if the circular hollow inner member 4212 is non-uniform between its exterior surface, which is adjacent the cutting blade, and its interior surface, which creates the lumen therethrough. Increasing the wall thickness for a portion of the circular hollow inner member 4212 guides the lead away from that portion of the inner cam member 4204 and towards the center of the lumen, thereby decreasing the likelihood that the cutting surface 4208 will cut the lead upon lead entry and/or upon extension of the cutting blade.

As illustrated in these figures, the interior surface and exterior surface of the circular hollow inner member is designed such that the thicker and thinner cross-sectional portions transitions to and from one another without the interruption along either the interior or the exterior surface of the circular hollow inner member, thereby creating a smooth and unpronounced transition between a thicker wall portion and thinner wall portion.

Figure 43A:
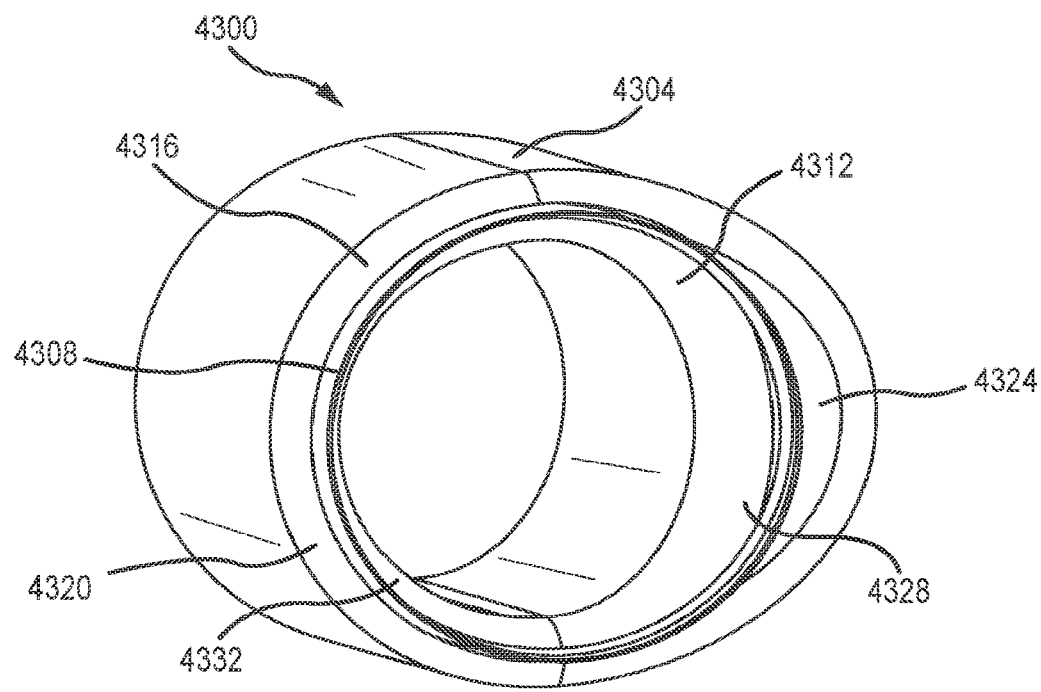
FIG. 43A is perspective view of an outer cam member, an inner cam member, a tubular inner member with a cutting blade therebetween according to an embodiment of the disclosure.
Figure 43B:
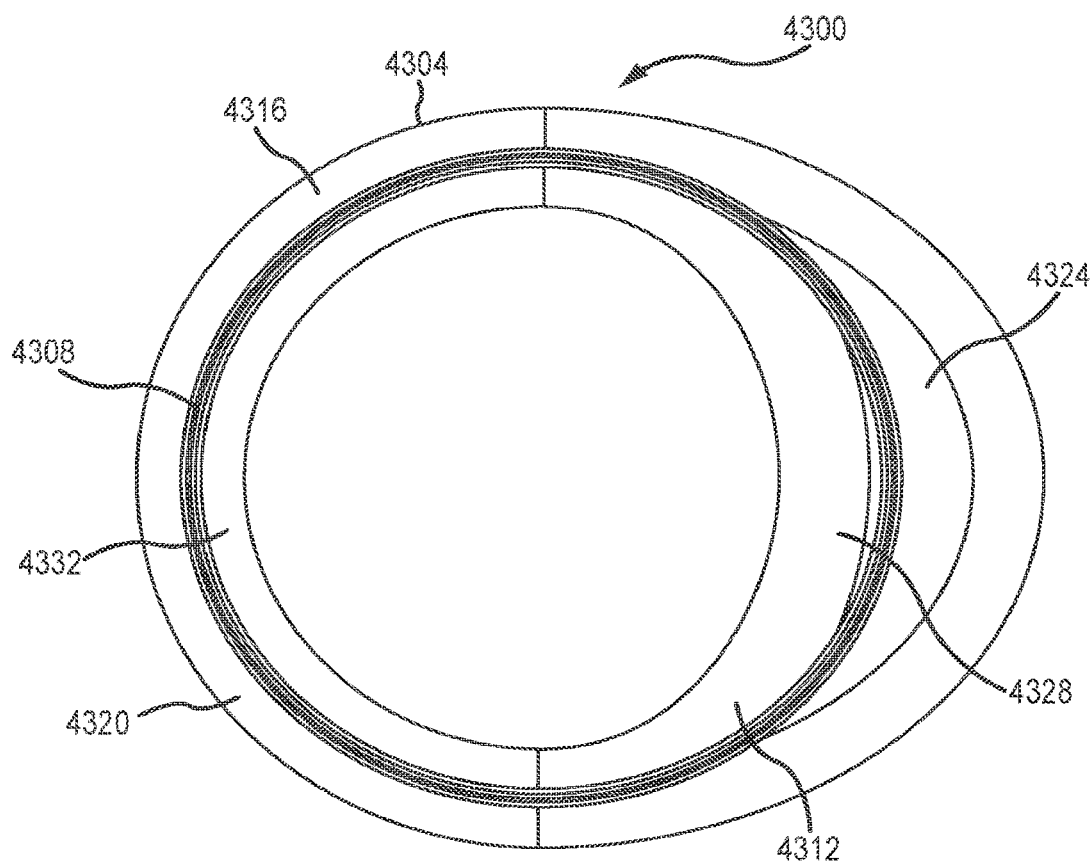
FIG. 43B is a distal end view of the outer sheath depicted in FIG. 43A.

The increased wall thickness for a portion of the circular hollow inner member 4212 may be in conjunction with an outer cam member 4204 having a wall thickness that is consistent around the entire circumference for a given cross section as illustrated in FIGS. 42A and 42B. And the increased wall thickness for a portion of the circular hollow inner member 4312 may be in conjunction with an outer cam member 4304 having a wall thickness that is non uniform for a given cross section as illustrated in FIGS. 43A and 43B. Continuing to refer to FIGS. 43A and 43B, there is depicted an illustration of an embodiment of the distal end 4300 of the inner sheath and the outer sheath. The inner sheath includes the inner cam member. The inner cam member, as depicted, has a cutting surface 4308 as well as a circular hollow inner member 4312 located within the lumen of the cutting blade. The outer sheath includes the outer cam member 4304. The outer cam member 4304 has a distal portion, and the most distal region of the distal portion of the outer cam member 4304 may be referred to as a distal end region 4316.

The outer wall thickness of the outer cam 4304 in FIGS. 43A and 43B is not uniform around the circumference for a given cross section of the outer cam member 4304. That is, the wall thickness is thinner at a portion 4320 of the cross section of the outer cam member 4304 in comparison to another portion 4324 for the same cross section. In other words, the wall thickness is greater at a portion 4324 of the cross section of the outer cam member 4304 in comparison to another portion 4320 for the same cross section.

The thickness of the circular hollow inner member 4312 is not uniform around the circumference for a given cross section. That is, the wall thickness is thinner at a portion 4332 of the cross section of the circular hollow inner member 4312 in comparison to another portion 4228 for the same cross section. In other words, the wall thickness is greater at a portion 4324 of the cross section of the circular hollow inner member 4312 in comparison to another portion 4332 for the same cross section. Increasing both the wall thickness of the outer cam member 4304 and the wall thickness for a portion of the circular hollow inner member 4312 assists in both shielding the vasculature from the blade 4308 during extension and guides the lead away from that portion of the inner cam member and towards the center of the lumen, thereby decreasing the likelihood that the cutting surface 4308 will either cut the lead upon lead entry (and/or upon extension of the cutting blade) or upon contact the tissue upon blade extension.

FIGS. 43A and 43B depict the increased portion 4328 of circular hollow inner member 4312 and the increased portion 4324 of the outer cam member 4304 as being radially aligned. However, the increased portions of the circular hollow inner member 4312 and the outer cam member 4304 need not be radially aligned and may be radially offset from one another. For example, the increased portions of the circular hollow inner member 4312 and the outer cam member 4304 may be radially offset from one another between 1 degree and 359 degrees.

Both the circular hollow inner member 4312 and the outer cam member 4304 may have a plurality of increased portions that are evenly or unevenly offset from one another. For example, referring to FIG. 44B, there is a depicted an outer cam member 4404 having a non-uniform thickness that includes two increased portions 4424, 4426 that are 180 degrees offset from one another, thereby creating an oval shaped cross-sectional profile of the distal end of the outer cam member 4404 viewed from the distal end thereof. Although it is not illustrated in the figures, the outer cam member may include three increased portions separated about 120 degrees from one another. Additionally, the outer cam member may include four increased portions separated about 90 degrees from one another. Again, the increased portions, however, do not have to be radially opposed from one another and may be offset from one another at any angle.

Figure 44A:
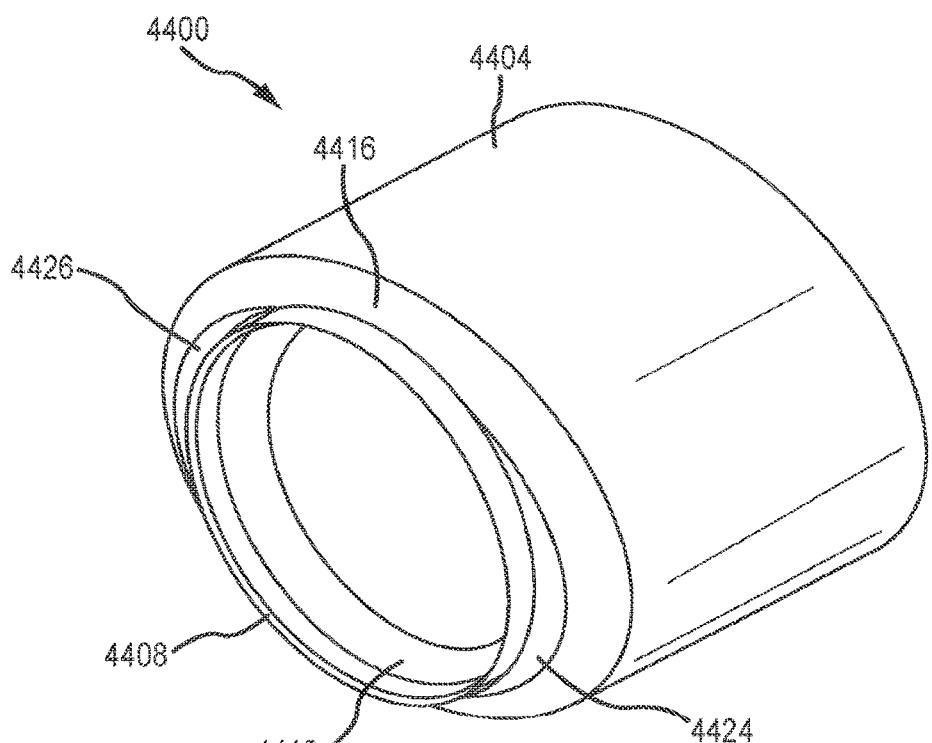
FIG. 44A is perspective view of an outer cam member, an inner cam member, a tubular inner member with a cutting blade therebetween according to an embodiment of the disclosure.
Figure 44B:
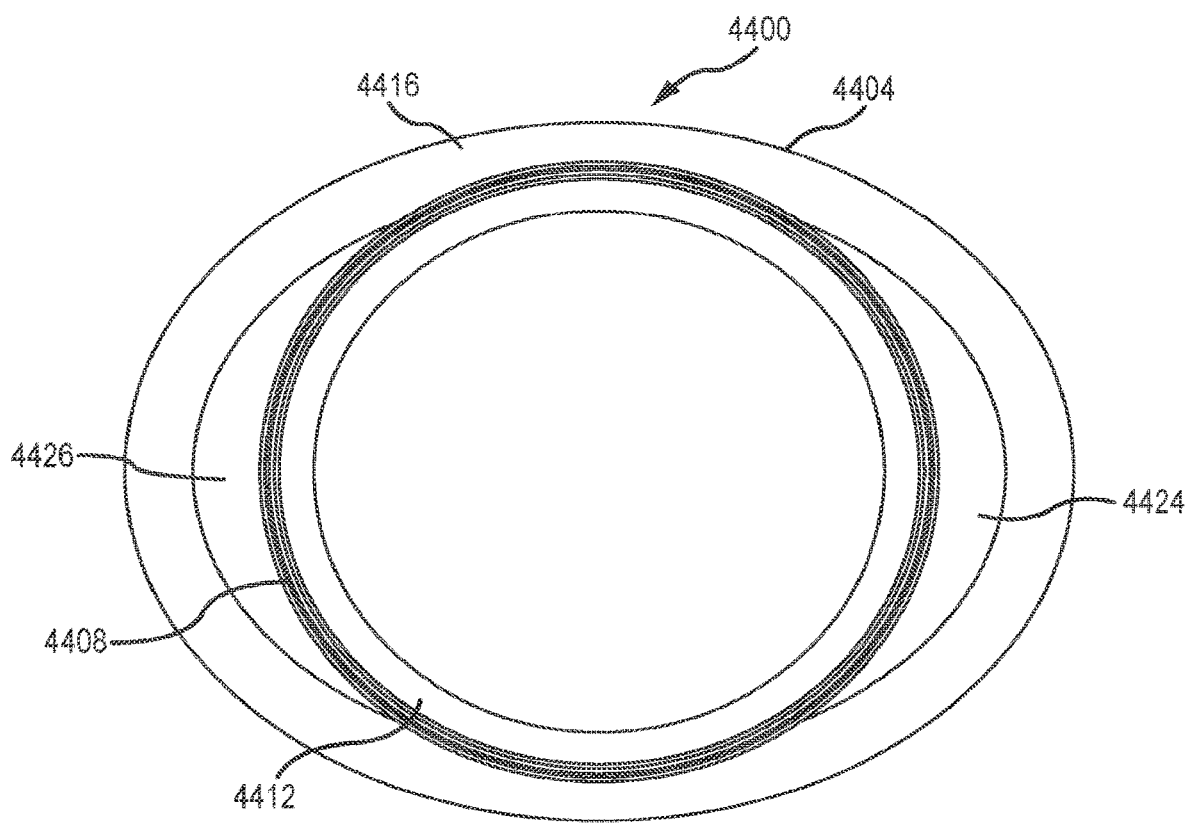
FIG. 44B is a distal end view of the outer sheath depicted in FIG. 44A.

Although FIGS. 44A and 44B illustrate the circular hollow inner member 4412 as having a uniform wall thickness, the circular hollow member 4412 may have a non-uniform wall thickness that includes one or more increased portions. For instance, the circular hollow inner member 4412 may have two increased portions that radially align with the two increased portions 4424, 4426 of the outer cam member. Alternatively, the circular hollow inner member 4412 may have two increased portions that are offset from the two increased portions 4424, 4426 of the outer cam member by 90 degrees or any other angle.

In order to assist the clinician using the surgical device to know where the one or more increased portions of the outer cam member and/or the circular hollow inner member, the surgical device may include indicators on the handle and/or the proximal end of the outer sheath that correspond to the radial position of the increased portions. For example, the indicators may include those described in commonly owned U.S. patent application Ser. No. 14/195,692 filed Mar. 3, 2014, entitled "Dilator Sheath Set", which is hereby incorporated herein by reference in its entirety for all that it teaches and for all purposes.

Figure 45A:
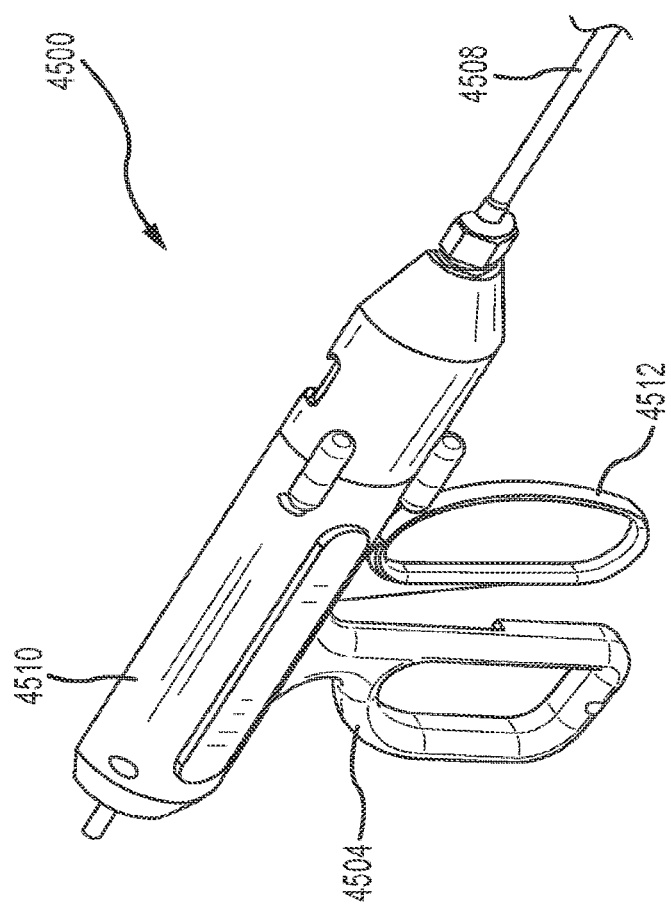
FIG. 45A is a perspective view of a surgical device according to an alternate embodiment of the disclosure, wherein the surgical device includes a housing, handle, trigger and elongated shaft.
Figure 45B:
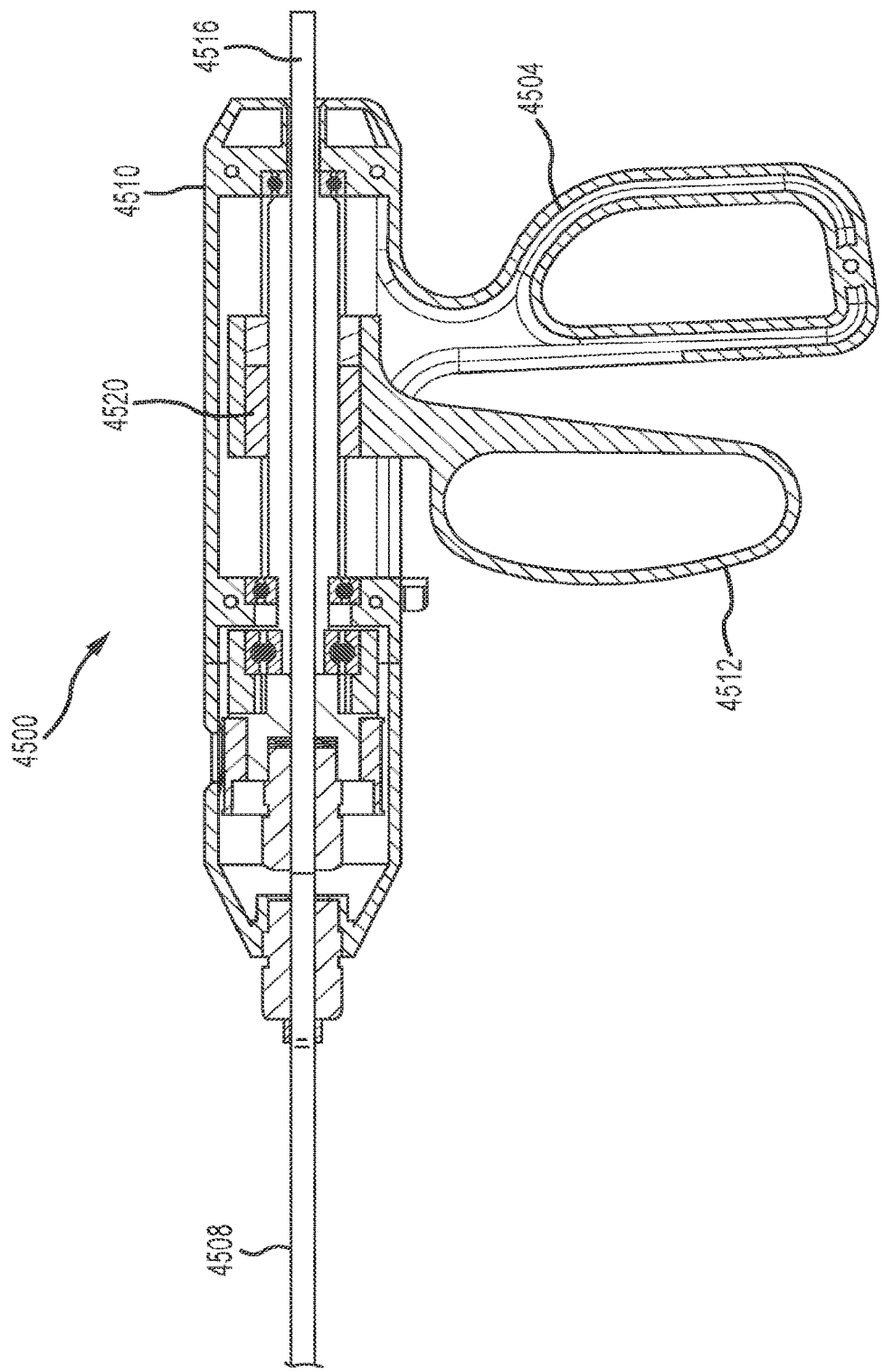
FIG. 45B is an enlarged cross-sectional view of the surgical device depicted in FIG. 45A.
Figure 45C:
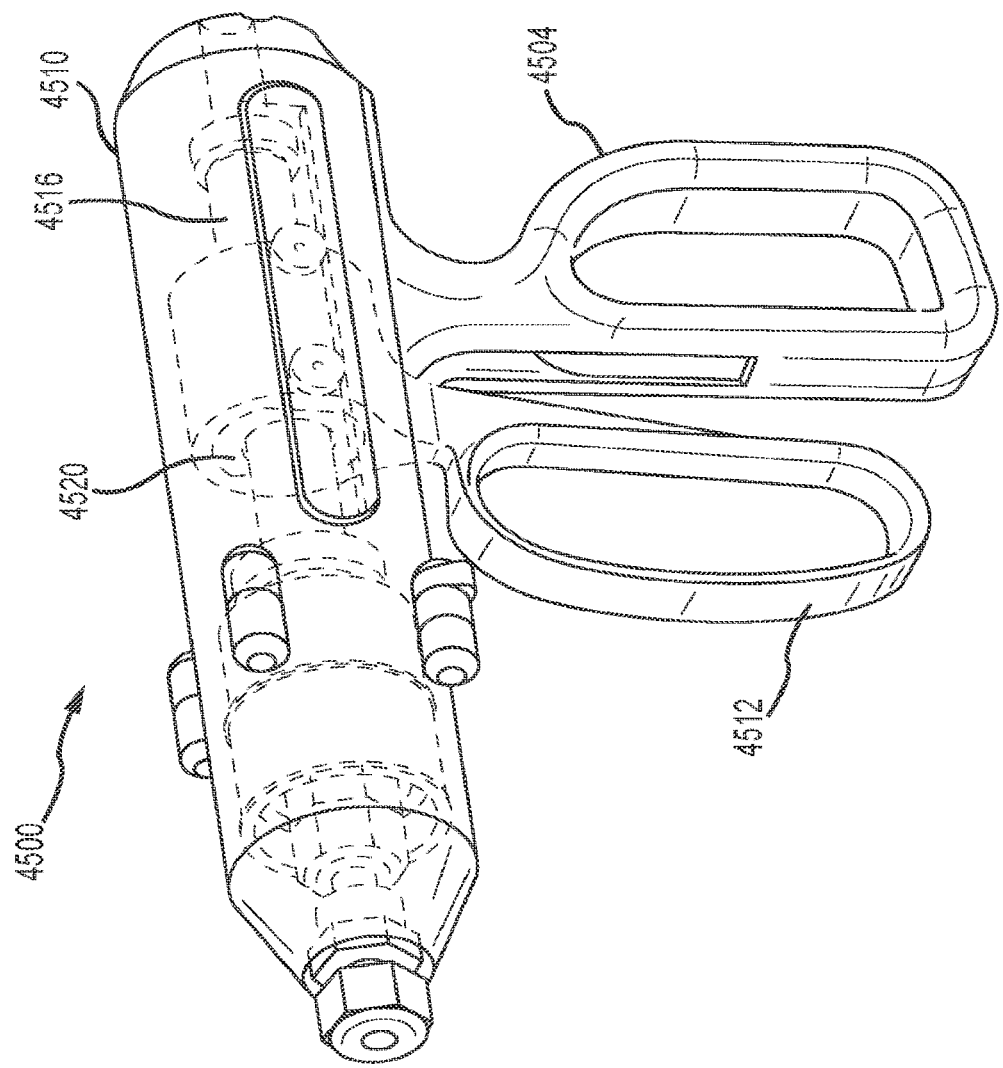
FIG. 45C is a transparent perspective view of the surgical device depicted in FIG. 45A.

Referring to FIG. 45, there is depicted an alternate embodiment of a surgical device 4500 having a housing 4510, an inner and outer sheath 4508 extending therefrom, a handle 4508, wherein the handle includes a trigger 4512 that is manually moveable in a linear (e.g., proximally and distally) direction. Referring to FIGS. 45A and 45B, a rotary actuator comprising a linear slide is included within the housing 4510. A linear slide may also be referred to as a linear-motion bearing. A linear slide is a bearing designed to provide motion in a particular direction or dimension. For the purposes of this disclosure, the rotary actuator converts linear motion to rotary motion. Accordingly, the linear slide is used to convert rotary motion from linear motion. There are various types of rotary actuators other than that discussed with respect to FIGS. 45A and 45B, and this disclosure is not intended to be limited to the rotary actuator described in these two figures. The rotary actuator described in these two figures includes a drive nut and leadscrew assembly. For example, the assembly includes a threaded nut 4520, which is disposed within the trigger 4512, and a rotatable threaded shaft 4516. At least a portion of the rotatable shaft 4516 is also threaded to matingly engage with the threaded nut 4512 when the rotatable shaft 4516 is disposed within the threaded lumen of the nut 4512. Upon linear actuation of the trigger 4512 in a proximal direction, the threaded nut 4520 also moves proximally. Because the threads of the rotatable shaft 4516 engage the threaded nut 4512, the shaft 4516 rotates as the threaded nut 4520 and trigger 4512 translate proximally. The shaft 4516 is coupled to the inner sheath, which in turn is coupled to the inner cam member. Accordingly, upon linear actuation of the trigger 4512, the inner cam member rotates and extends distally and/or retracts proximally, as discussed hereinbefore.

As mentioned above, this disclosure is not limited to the embodiment of the rotary actuator and/or the linear slide discussed with respect to FIGS. 45A and 45B. For example, other rotary actuators may include a linear slide embodiment having a nut or other object having a threaded inner lumen and a shaft having one or more series of mating keys (or pins) on its exterior that act as a follower, thereby imparting rotation to the shaft upon linear movement by the nut or other object. Alternatively, the exterior of the shaft may be threaded and the nut may have either a one or more series of mating keys (or pins) on or in its lumen that follow the thread on the shaft and impart rotation to the shaft. Furthermore, the rotary actuator may include a linear slide comprising a rolling ring bearing (or an assembly of a plurality of rolling ring bearings) and an unthreaded shaft.

A tension spring and/or a compression spring are also included within the housing and connected to the trigger 4512 and/or shaft 4516. Upon the clinician's release of the trigger 4512, the tension spring and/or compression spring force the trigger 4512 and nut 4520 to move distally and return to their original position. As the trigger 4512 and nut 4520 translate distally, the shaft 4516 rotates in the opposite direction, and the inner cam member rotates and extends distally and/or retracts proximally. The rotary actuator and/or linear slide, as described herein, provides a smooth actuation and cooperation between the trigger and inner sheath.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

Presented herein are embodiments of a tissue separating device, system, and method. As described herein, the device(s) may be electrical, mechanical, electro-mechanical, and/or combination thereof.

A number of variations and modifications of the disclosure may be used. It would be possible to provide for some features of the disclosure without providing others.

In some embodiments, the systems and methods of this disclosure may be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein may be used to implement the various aspects of this disclosure. Exemplary hardware that may be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing may also be constructed to implement the methods described herein.

The present disclosure, in various aspects, embodiments, and/or configurations, includes components, methods, processes, systems and/or apparatus substantially as depicted and described herein, including various aspects, embodiments, configurations embodiments, sub combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

Figure 28:
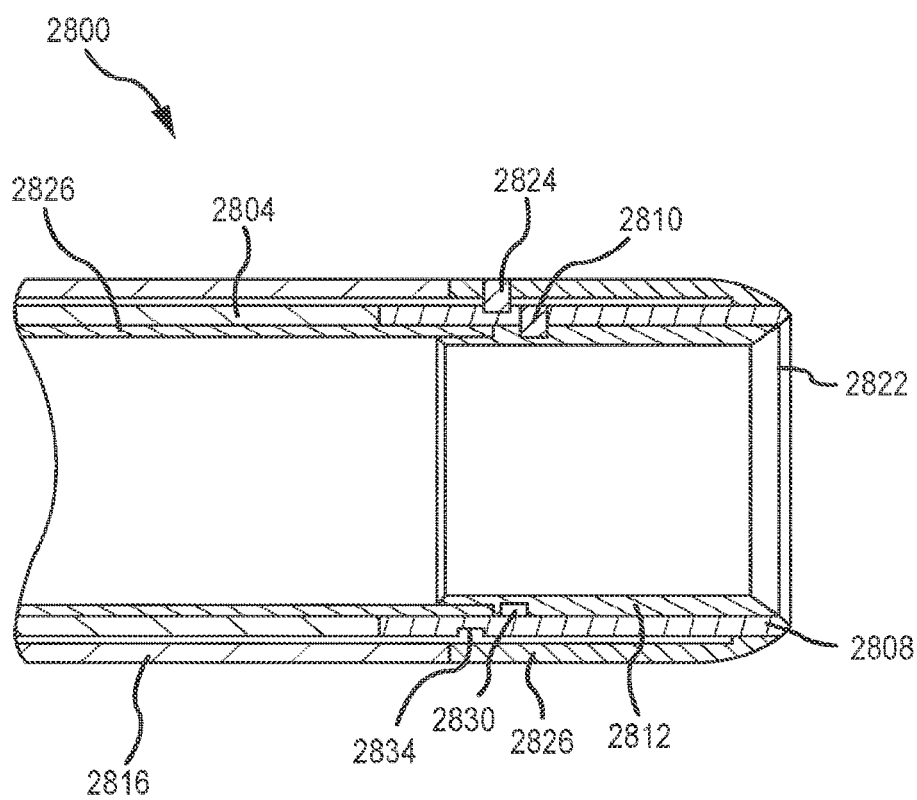
FIG. 28 is a cross-sectional view of the distal portion of the cutting sheath assembly according to an alternate embodiment of the disclosure, wherein a cutting blade in a retracted position.
Figure 29A:
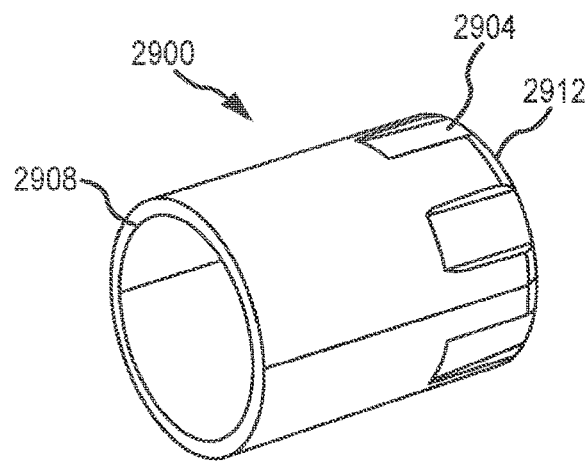
FIG. 29A is perspective view of a distal tip of the outer sheath according to an embodiment of the disclosure.
Figure 29B:
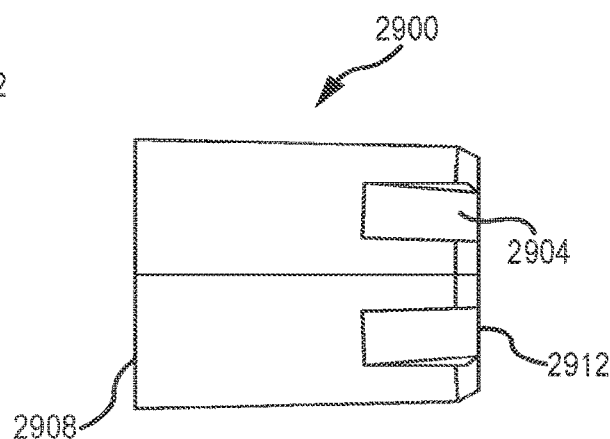
FIG. 29B is side view of the distal tip illustrated in FIG. 29A.
Figure 29C:
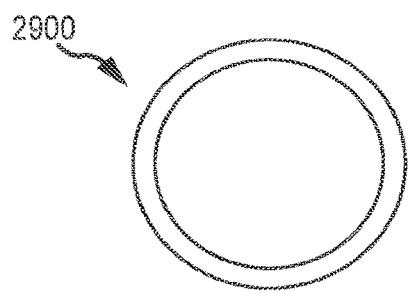
FIG. 29C is proximal end view of the distal tip illustrated in FIG. 29A.
Figure 29D:
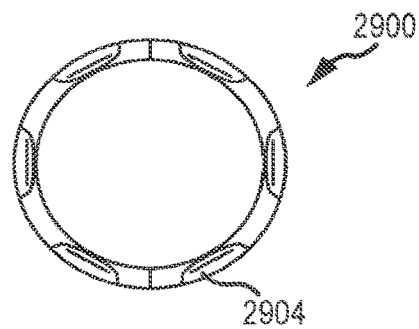
FIG. 29D is distal end view of the distal tip illustrated in FIG. 29A.
Figure 30A:
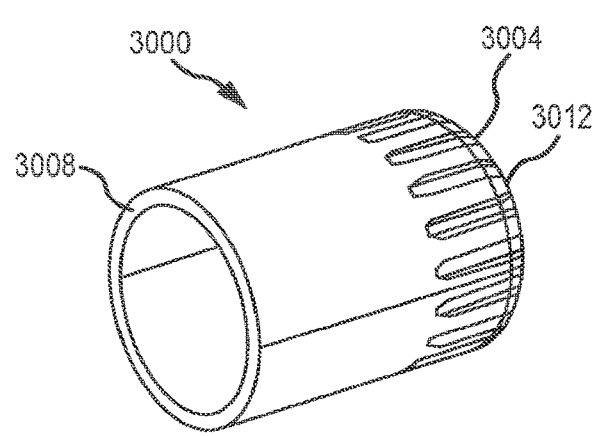
FIG. 30A is perspective view of a distal tip of the outer sheath according to an embodiment of the disclosure.
Figure 30B:
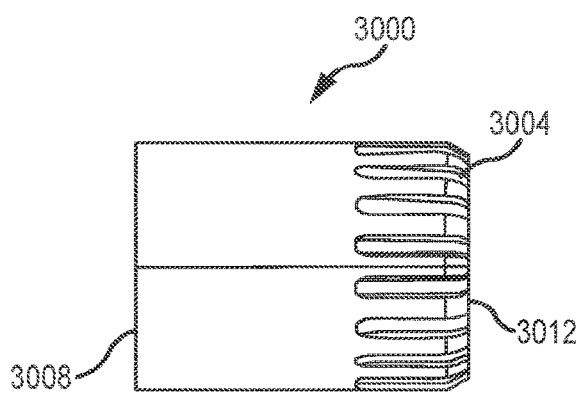
FIG. 30B is side view of the distal tip illustrated in FIG. 30A.
Figure 30C:
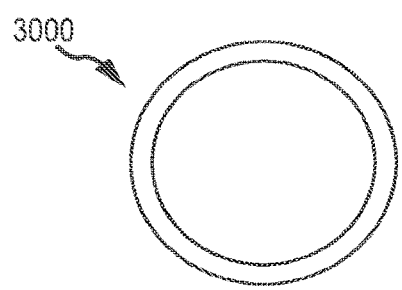
FIG. 30C is proximal end view of the distal tip illustrated in FIG. 30A.
Figure 30D:
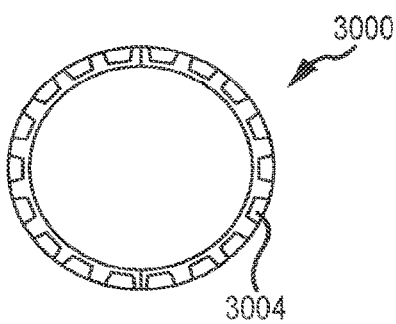
FIG. 30D is distal end view of the distal tip illustrated in FIG. 30A.
Figure 31A:
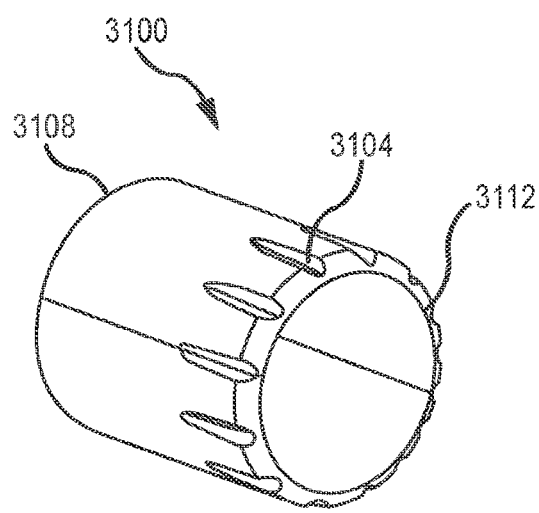
FIG. 31A is perspective view of a distal tip of the outer sheath according to an embodiment of the disclosure.
Figure 31B:
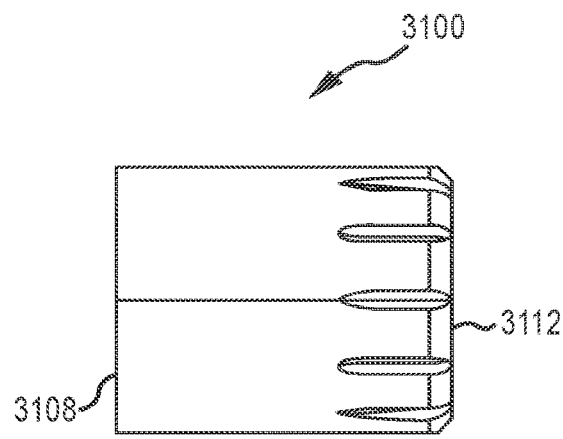
FIG. 31B is side view of the distal tip illustrated in FIG. 31A.
Figure 31C:
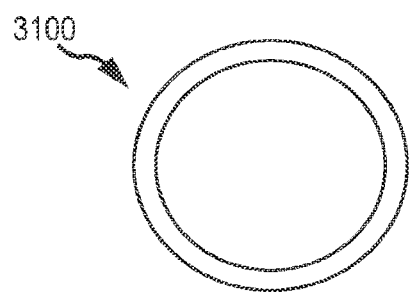
FIG. 31C is proximal end view of the distal tip illustrated in FIG. 31A.
Figure 31D:
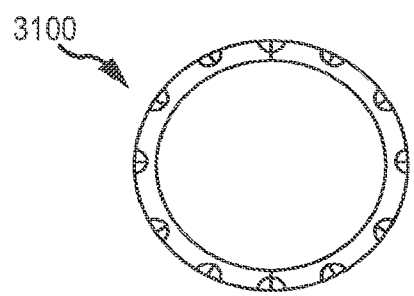
FIG. 31D is distal end view of the distal tip illustrated in FIG. 31A.

For example, the disclosure discusses two sheaths—and inner sheath and an outer sheath. Additionally, the disclosure discusses using two cam members—an outer stationary cam member and an inner telescopically, rotatable cam member. With preference to FIG. 28, it may be beneficial to use additional rotatable sheaths, stationary sheaths, stationary cam members and/or rotatable cam members. FIG. 28 depicts an alternate exemplary embodiment of the distal portion of the sheaths. This figure illustrates a flexible stationary outer sheath 2816, a flexible extendable intermediate sheath 2804, and a flexible extendable inner sheath 2826. Coupled to the outer sheath 2816 is a rotatable outer cam member 2826. Coupled to the intermediate sheath 2804 is a rotatable intermediate cam member 2808. Coupled to the inner sheath 2826 is a rotatable inner cam member 2812. The inner cam member 2812 is connected to the intermediate cam member 2808 by pin 2810. The intermediate cam member 2808 is connected to the outer cam member by pin 2824. As the inner sheath 2826 extends distally, the inner cam member rotates and travels according to the profile of cam slot 2830 in which the pin 2810 sits. Similarly, as the intermediate sheath 2804 extends distally, the intermediate cam member rotates and travels according to the profile of the cam slot 2834 in which the pin 2824 sits. Utilizing multiple rotatable and extendable sheaths, as well as rotatable cam members, allows the device to increase the extension and rotation of the cutting surface. This is only one example of an alternative embodiment, and depending upon the amount of blade extension and/or desired rotation and/or movement of the cutting blade, those of skill in the art will understand how to make and use the disclosed aspects, embodiments, and/or configurations after understanding the present disclosure to adjust the location, size, configuration and/or type of indicator. All such configurations within the knowledge of one skilled in the art are considered within the scope of this disclosure.

Additionally, various types of cams, such as single lobe cams and double lobe cams are discussed within this disclosure. Other lobe cam configurations, such as triple lobe cams, may be used. Similar, the increment of the additional length of cam slot need not be 90 degrees beyond 360 degrees. For example, the additional length of cam slot can be in increments of 5, 10, 15, 30, 45, 60 degrees, etc. Furthermore, although the slope of the cam slot between two positions and/or points has been described as generally linear, the slope between two points need not be linear. Rather, the cam slot and/or slope of the cam slot can be non-linear, such as a sinusoidal shape, which may or may not have a generally linear portion. The sinusoidal shape, particularly at the transition points allows for a smooth transition of the inner cam member, inner sheath, and/or cutting surface from an extended direction to retracted direction through such positions while maintaining a relatively constant rate of rotation, thereby allowing the cutting surface to continue to rotate and cut the tissue through such transition.

Moreover, although a pin and slot cam configuration is discussed within this disclosure, other possible cam configurations may be used. For example, a captured ring cam configuration may be used. A captured ring cam configuration may include a ring that is attached to at least one of the inner sheath (or inner member attached to the inner sheath) or the outer sheath (or outer member attached to the outer sheath) and that is captured by two angled lobes on the other sheath (or member). Although the ring may be captured by one lobe, it may be preferred for the ring to be captured by two lobes—one on each side of the ring—such that cutting surface may be forced in both a proximal direction (toward a retraction position) and distal direction (toward an extended direction). The benefit of being able to force the cutting surface in both directions with the aid of the captured cam configuration potentially negates the need for a spring or other retraction mechanism to force the inner sheath (or inner member) and cutting surface back within the outer sheath (or outer member).

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device for removing an implanted object from a body vessel, the device comprising:
   a handle;
   a trigger movably coupled to the handle;
   an elongated sheath extending from the handle, the elongated sheath comprising a proximal end, a distal end, and a lumen extending from the distal end toward the proximal end, wherein the lumen is configured to receive an implanted object, the elongated sheath further comprising a proximal portion and a distal portion;
   a tubular outer member attached to the distal portion of the elongated sheath, wherein at least one portion of the tubular outer member has a non-uniform circumferential wall thickness that is thicker at a distal end of the tubular outer member than at a proximal end of the tubular outer member;
   a tubular inner member located within the tubular outer member, the tubular inner member comprising a proximal end, a distal end and an exterior surface therebetween, the distal end comprising a cutting surface; and
   an actuator disposed within the handle, the actuator comprising a linear slide coupled to the trigger, such that upon movement of the trigger relative to the handle, the tubular inner member rotates and the distal end of the tubular inner member moves axially and extends distally beyond the tubular outer member.

2. The device of claim 1 wherein the linear slide comprises a rolling ring bearing and an unthreaded shaft, wherein the unthreaded shaft is coupled to the tubular inner member.

3. The device of claim 1, wherein the non-uniform circumferential wall thickness comprises a first segment and a second segment, wherein the first segment has a thickness greater than the second segment.

4. The device of claim 3, wherein the first segment is disposed opposite the second segment along a cross section of a circumference of the tubular outer member.

5. The device of claim 3, wherein the tubular outer member comprises an outer surface, and wherein the first segment transitions to the second segment without interruption on the outer surface.

6. The device of claim 3, wherein at least one of the handle and the elongated sheath comprise an indicator indicative of a location of at least one of the first segment and the second segment.

7. The device of claim 1, wherein the non-uniform circumferential wall thickness comprises a first segment, a second segment, and a third segment, wherein the first segment and the second segment have a thickness greater than the third segment.

8. The device of claim 7, wherein the first segment and the second segment have a substantially similar thickness profile.

9. The device of claim 1, wherein the tubular outer member has a proximal end portion and a distal end portion, wherein the at least one portion of the tubular outer member having the non-uniform circumferential wall thickness is located at least at the distal end portion.

10. The device of claim 9, wherein the at least one portion of the tubular outer member having the non-uniform circumferential wall thickness comprises a first segment having a thickness greater than a second segment.

11. The device of claim 9, wherein the at least one portion of the tubular outer member having the non-uniform circumferential wall thickness comprises a first segment, a second segment, and a third segment, wherein the first segment and the second segment have a thickness greater than the third segment.

12. The device of claim 1, wherein the tubular inner member is a first tubular inner member, and further comprising a second tubular inner member, wherein at least one portion of the second tubular inner member has a non-uniform circumferential wall thickness.

13. The device of claim 12, further comprising a third tubular member located within the tubular inner member, wherein at least one portion of the third tubular member has a non-uniform circumferential wall thickness.

14. The device of claim 12, wherein the non-uniform circumferential wall thickness of the third tubular member comprises a first segment and a second segment, wherein the first segment has a thickness greater than the second segment.

15. The device of claim 14, wherein the non-uniform circumferential wall thickness comprises a first segment and a second segment, wherein the first segment has a thickness greater than the second segment.

16. The device of claim 15, wherein the first segment is disposed opposite the second segment along a cross section of a circumference of the second tubular inner member.

17. The device of claim 1 further comprising a pin attached to the tubular outer-member and extending inwardly thereof.

18. The device of claim 11 wherein the exterior surface of the tubular inner member comprises a cam slot for receipt of and cooperation with the pin upon actuation of the trigger.

* * * * *